United States Patent
Alon

(10) Patent No.: US 10,206,776 B2
(45) Date of Patent: Feb. 19, 2019

(54) HEART VALVE REPAIR AND REPLACEMENT

(71) Applicant: David Alon, Zichron Yaacov (IL)

(72) Inventor: David Alon, Zichron Yaacov (IL)

(73) Assignee: Cardiac Implants, LLC, Tarrytown, NY (US)

( * ) Notice: Subject to any disclaimer, the term of this patent is extended or adjusted under 35 U.S.C. 154(b) by 81 days.

(21) Appl. No.: 14/895,711

(22) PCT Filed: Jun. 3, 2014

(86) PCT No.: PCT/IB2014/000949
§ 371 (c)(1),
(2) Date: Dec. 3, 2015

(87) PCT Pub. No.: WO2014/195786
PCT Pub. Date: Dec. 11, 2014

(65) Prior Publication Data
US 2016/0120645 A1    May 5, 2016

Related U.S. Application Data

(60) Provisional application No. 61/831,632, filed on Jun. 6, 2013.

(51) Int. Cl.
*A61F 2/24* (2006.01)
*A61B 17/04* (2006.01)
(Continued)

(52) U.S. Cl.
CPC ........ *A61F 2/2442* (2013.01); *A61B 17/0487* (2013.01); *A61F 2/2445* (2013.01);
(Continued)

(58) Field of Classification Search
CPC ............ A61F 2220/0016; A61F 2/2409; A61F 2220/0008; A61F 2/2445;
(Continued)

(56) References Cited

U.S. PATENT DOCUMENTS 688,592 A   12/1901 Chadwick
4,042,979 A   8/1977 Angell
(Continued)

FOREIGN PATENT DOCUMENTS

CN   1684644 A   10/2005
CN   2782049      5/2006
(Continued)

OTHER PUBLICATIONS

Cohn, et al., "The Evolution of Mitral Valve Surgery," Am heart Hosp. J. 2003:1 pp. 40-46 (2003).
(Continued)

*Primary Examiner* — Ann Schillinger
(74) *Attorney, Agent, or Firm* — Potomac Law Group, PLLC

(57) ABSTRACT

Apparatuses and methods are disclosed for performing a procedure on a heart valve in which a loop of material (160) is configured to contact at least a portion of the annulus or the leaflets of a valve. A plurality of anchors (16) are distributed about the loop and configured for implantation into the annulus or the leaflets in a forward direction. The anchors are configured to resist extraction in a backwards direction. A plurality of linking members (150) are affixed to the loop of material and at least a portion of each linking member passes through a slot (17) in a respective anchor so that the linking members can slide with respect to the slots. The anchors are then implanted into the annulus or the leaflets. The loop can then be used to retain a replacement valve or to cinch the annulus. A number of particularly advantageous anchor configurations are also disclosed.

12 Claims, 51 Drawing Sheets

(51) Int. Cl.
- *A61B 17/068* (2006.01)
- *A61B 17/00* (2006.01)
- *A61B 17/064* (2006.01)

(52) U.S. Cl.
CPC .......... *A61F 2/2466* (2013.01); *A61B 17/068* (2013.01); *A61B 2017/00867* (2013.01); *A61B 2017/0409* (2013.01); *A61B 2017/0414* (2013.01); *A61B 2017/0427* (2013.01); *A61B 2017/0437* (2013.01); *A61B 2017/0464* (2013.01); *A61B 2017/0647* (2013.01); *A61F 2220/0008* (2013.01); *A61F 2220/0016* (2013.01)

(58) Field of Classification Search
CPC ............ A61F 2220/0075; A61F 2/2412; A61F 2250/0069; A61F 2/2457; A61F 2/24; A61F 2/2442
See application file for complete search history.

(56) References Cited

U.S. PATENT DOCUMENTS

| | | | |
|---|---|---|---|
| 5,860,951 | A | 1/1999 | Eggers et al. |
| 6,283,961 | B1 | 9/2001 | Underwood et al. |
| 6,306,163 | B1 | 10/2001 | Fitz |
| 6,575,971 | B2 | 6/2003 | Hauck et al. |
| 6,626,930 | B1 | 9/2003 | Allen et al. |
| 6,656,221 | B2 | 12/2003 | Taylor et al. |
| 6,716,243 | B1 | 4/2004 | Colvin et al. |
| 6,718,985 | B2 | 4/2004 | Hlavka et al. |
| 6,723,038 | B1 | 4/2004 | Schroeder et al. |
| 7,314,485 | B2 | 1/2008 | Mathis |
| 7,588,582 | B2 | 9/2009 | Starksen et al. |
| 13,430,926 | | 4/2013 | Kirson |
| 2002/0095175 | A1* | 7/2002 | Brock .................... A61B 34/30 606/205 |
| 2004/0073302 | A1 | 4/2004 | Rourke et al. |
| 2004/0102839 | A1 | 5/2004 | Cohn et al. |
| 2004/0102840 | A1 | 5/2004 | Solem et al. |
| 2004/0220610 | A1 | 11/2004 | Kreidler et al. |
| 2004/0243227 | A1 | 12/2004 | Starksen et al. |
| 2005/0070924 | A1 | 3/2005 | Schaller et al. |
| 2005/0107812 | A1 | 5/2005 | Starksen et al. |
| 2005/0119523 | A1 | 6/2005 | Starksen et al. |
| 2005/0216078 | A1 | 9/2005 | Starksen et al. |
| 2005/0273138 | A1 | 12/2005 | To et al. |
| 2006/0025750 | A1 | 2/2006 | Starksen et al. |
| 2006/0025784 | A1 | 2/2006 | Starksen et al. |
| 2006/0025787 | A1 | 2/2006 | Morales et al. |
| 2006/0058817 | A1 | 3/2006 | Starksen et al. |
| 2006/0069429 | A1 | 3/2006 | Spence et al. |
| 2006/0129188 | A1 | 6/2006 | Starksen et al. |
| 2007/0016286 | A1 | 1/2007 | Herrmann et al. |
| 2007/0244554 | A1 | 10/2007 | Rafiee et al. |
| 2008/0051823 | A1 | 2/2008 | Makower et al. |
| 2008/0177380 | A1 | 7/2008 | Starksen et al. |
| 2008/0177382 | A1 | 7/2008 | Hyde et al. |
| 2008/0243150 | A1 | 10/2008 | Starksen et al. |
| 2008/0262609 | A1 | 10/2008 | Gross et al. |
| 2009/0076597 | A1 | 3/2009 | Dahlgren et al. |
| 2009/0093890 | A1 | 4/2009 | Gelbart |
| 2009/0177277 | A1 | 7/2009 | Milo |
| 2009/0287304 | A1 | 11/2009 | Dahlgren et al. |
| 2010/0249920 | A1* | 9/2010 | Bolling .............. A61B 17/0644 623/2.11 |
| 2011/0106247 | A1 | 5/2011 | Miller et al. |
| 2011/0230961 | A1 | 9/2011 | Langer et al. |
| 2011/0301701 | A1 | 12/2011 | Padala et al. |
| 2012/0010700 | A1 | 1/2012 | Spenser |
| 2013/0331930 | A1 | 12/2013 | Rowe et al. |
| 2014/0309730 | A1 | 10/2014 | Alon et al. |
| 2016/0120645 | A1 | 5/2016 | Alon |

FOREIGN PATENT DOCUMENTS

| | | |
|---|---|---|
| CN | 102215784 A | 10/2011 |
| JP | 2007514455 A | 6/2007 |
| JP | 2009507532 A | 2/2009 |
| JP | 2010511469 A | 4/2010 |
| WO | 2005025644 A2 | 3/2005 |
| WO | 2006052687 A1 | 5/2006 |
| WO | 2008068756 A2 | 6/2008 |
| WO | 2009120764 A2 | 10/2009 |
| WO | 2010091383 A2 | 8/2010 |
| WO | 2010108079 A1 | 9/2010 |
| WO | 2012084714 A2 | 6/2012 |
| WO | 2013088327 A1 | 6/2013 |

OTHER PUBLICATIONS

Daimon, et al., "Percutaneous Mitral Valve Repair for Chronic Ischemic Mitral Regurgitation." Journal of the American Heart Association, publ. Apr. 25, 2005.
Desimone, et al., "Adjustable Tricuspid Valve Annuloplasty Assisted by Intraoperative Transesophageal." The American Journal of Cardiology vol. 71 pp. 926-931 Apr. 15, 1993.
Felger, M.D., et al., "Robot-assisted Sutureless Minimally Invasive Mitral Valve Repair", Cardiovascular Surgery, Surgical Technology International XII, p. 185-187 (undated).
Folliguet, et al., "Mitral valve repair robotic versus stemotomy" European Journal of Cardio-Thoracic Surgery 29 (2006) pp. 362-366.
Greelish et al., "Minimally invasive mitral valve repair suggests earlier operations for mitral valve," The Journal of thoracic & Cardiovascular Surgery vol. 126, No. 2 (2003).
International Search Report and Written Opinion for International Application No. PCT/IB2014/000949 dated Jan. 20, 2015.
International Search Report and Written Opinion in corresponding application PCT/IB2012/057138, 14 pages, dated Feb. 28, 2013.
Maniu, MD, et al. :Acute & Chronic Reduction of Functional Mitral Regurgitation Journal of Merican College of Cardiology, vol. 44, No. 8, pp. 1652-1661 (2004).
Office Action for Japanese Patent Application No. 2014-545447 dated Oct. 31, 2016 (includes English language translation).
Office Action for U.S. Appl. No. 14/364,060 dated Nov. 23, 2016.
Office Action dated Aug. 18, 2017, in Chinese Patent Application 201610004737.X (with translation).
International Search Report and Written Opinion for application No. PCT/US2016/014397 dated May 9, 2016.
Office Action issued in Japanese application No. JP 2016-517696 dated Feb. 19, 2018.
Notice of Allowance dated Oct. 16, 2018 (Heisei 30) in counterpart Japanese application No. JP 2016-517696 citing JP 2009-507532.

* cited by examiner

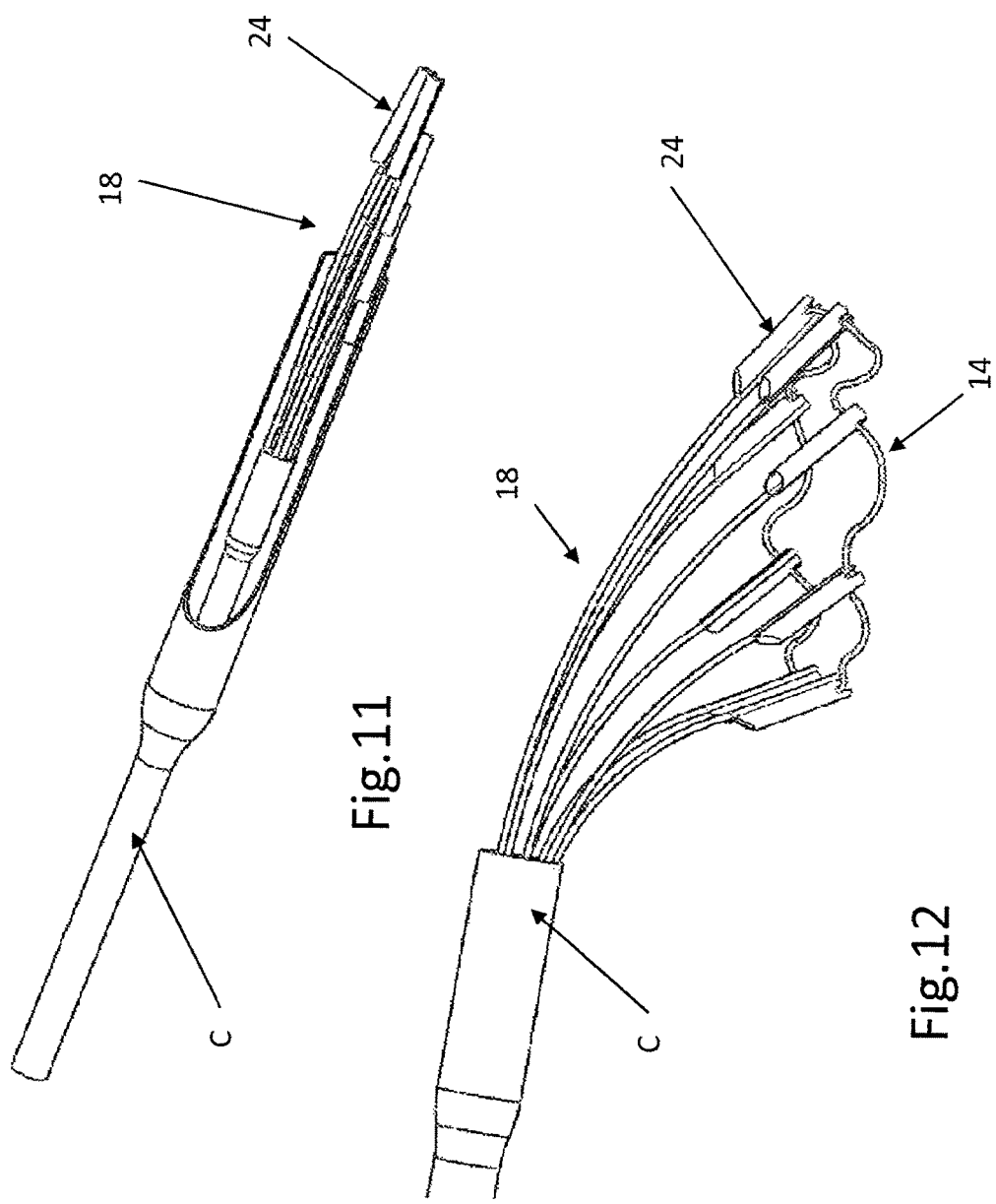

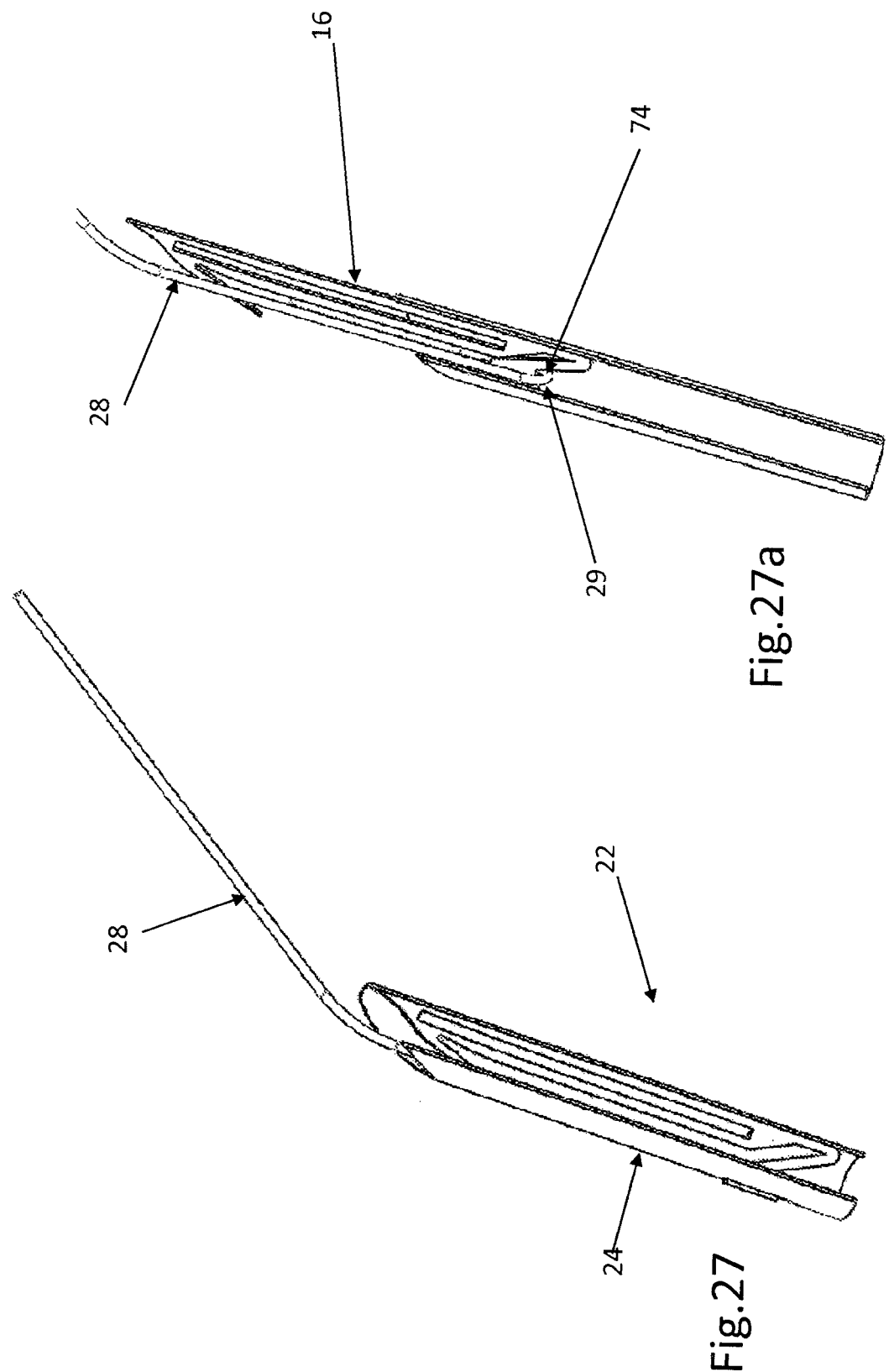

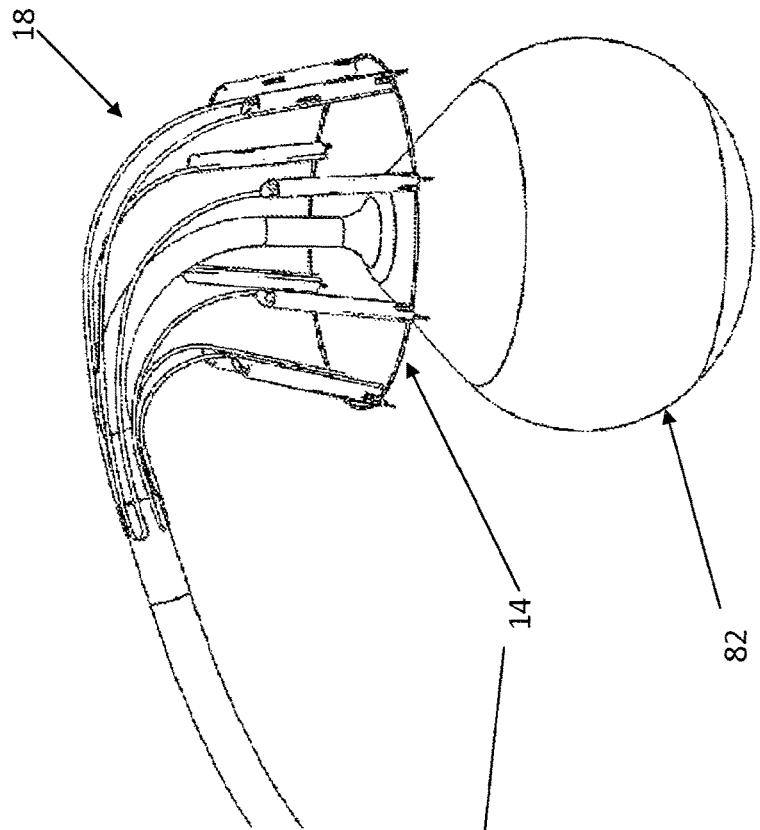
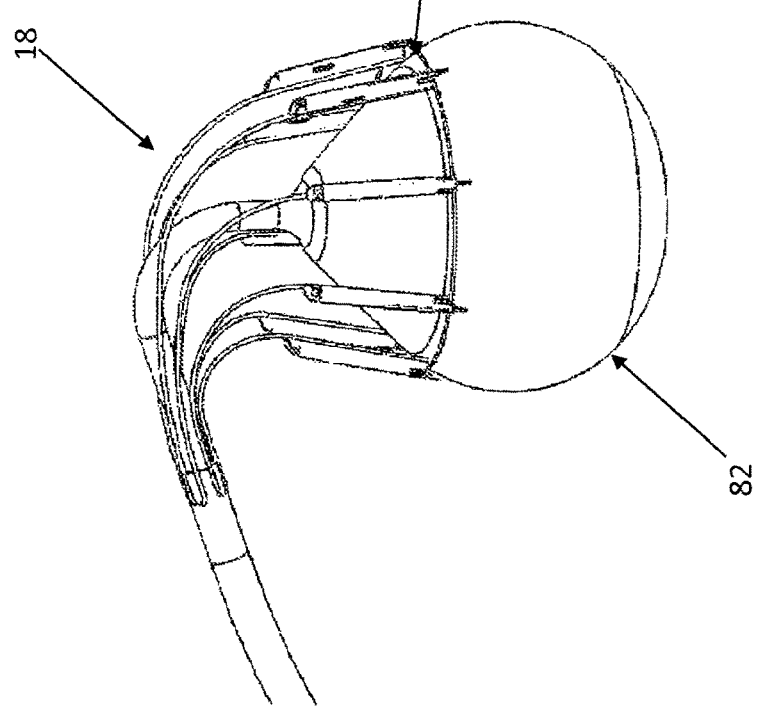

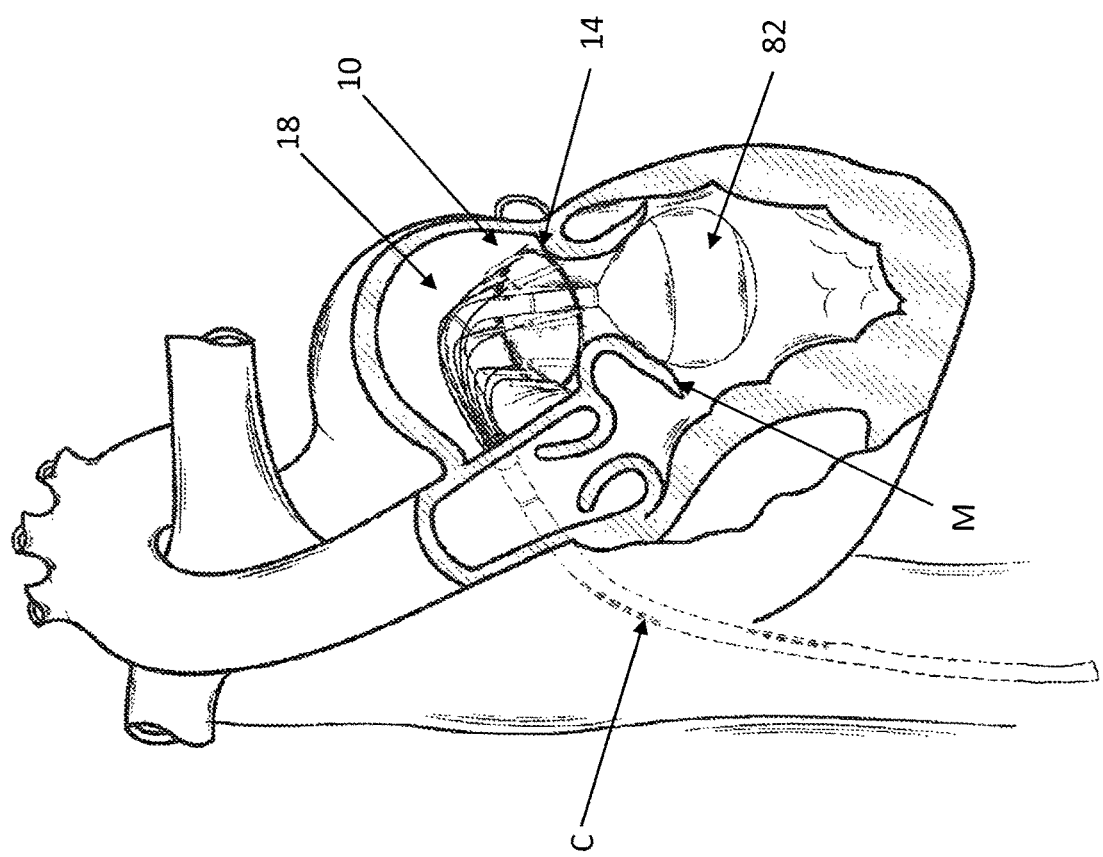

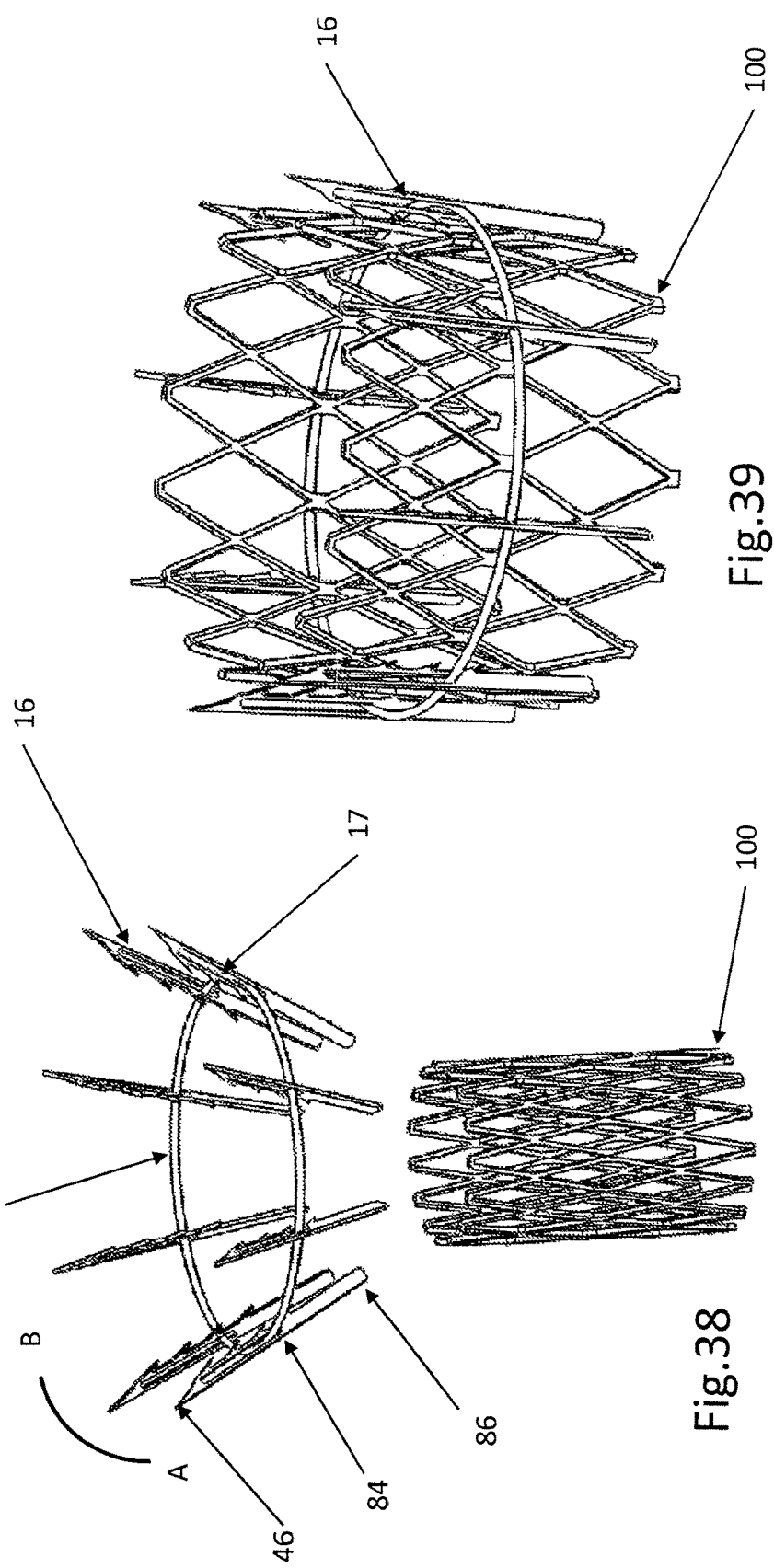

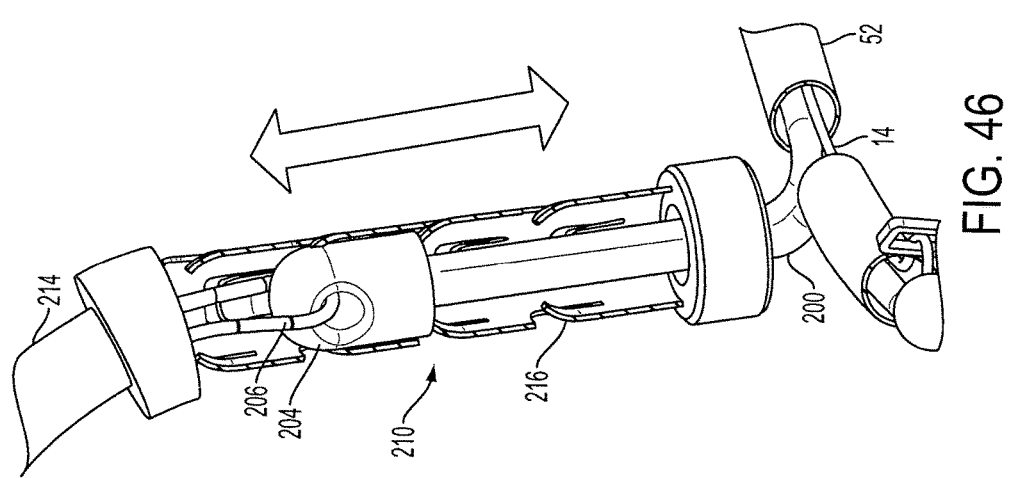

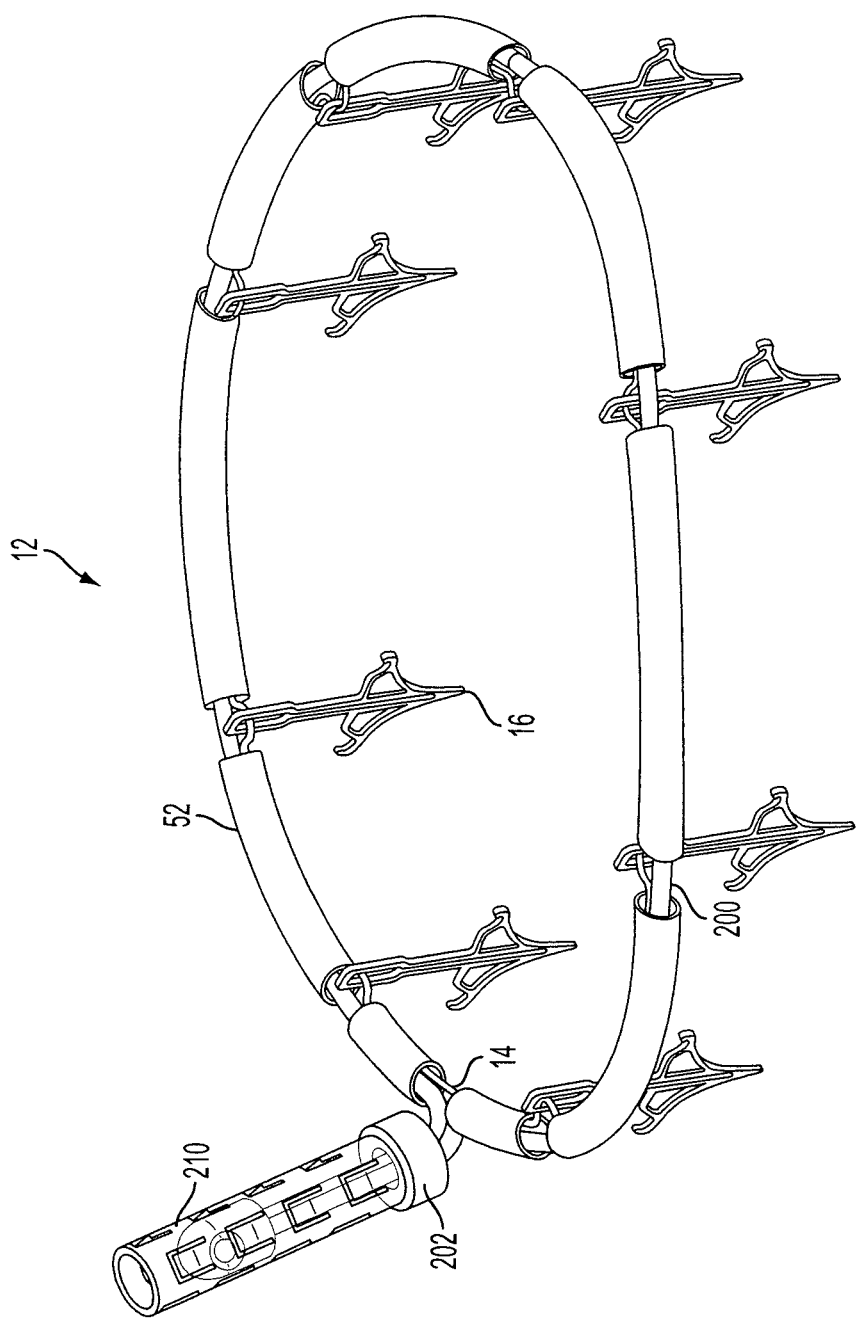

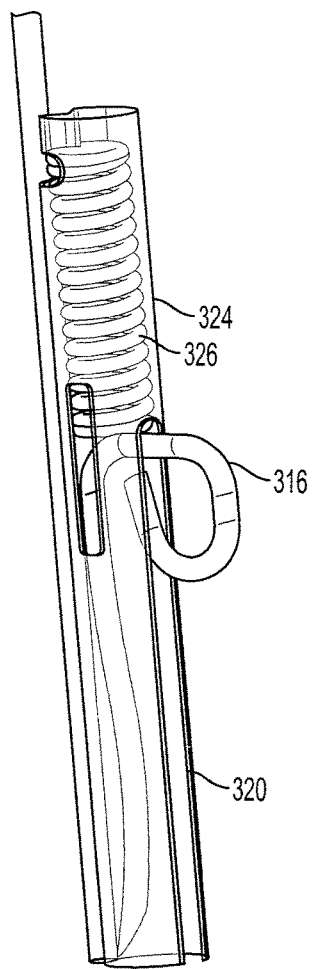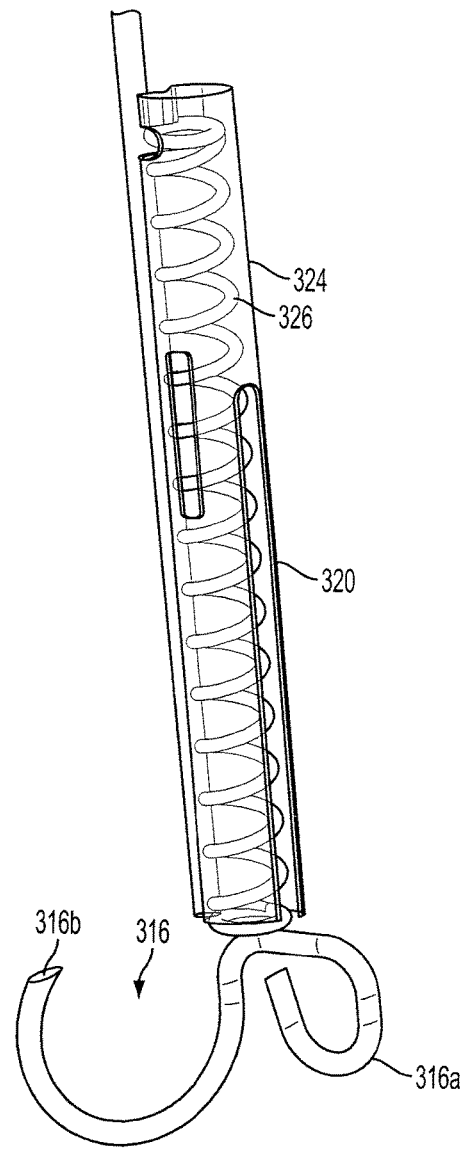
FIG. 57A
FIG. 57B

HEART VALVE REPAIR AND REPLACEMENT

CROSS REFERENCE TO RELATED APPLICATIONS

This Application is a national stage application under 35 U.S.C. § 371 of PCT/IB2014/000949 filed Jun. 3, 2013, which published as WO 2014/195786 and claims the benefit of U.S. Provisional Application 61/831,632, filed Jun. 6, 2013. Each of the above-identified applications is incorporated herein by reference.

BACKGROUND

The mitral valve is positioned in the heart left side, between the left atrium and the left ventricle. The most typical disease of the mitral valve is insufficiency or regurgitation which occurs when the valve leaflets do not coapt properly. Mitral valve repair by suturing a ring to reduce the annulus diameter is the procedure of choice to correct mitral regurgitation. With the use of current surgical techniques, most regurgitant mitral valves can be repaired or replaced with artificial valve prosthesis.

In the past, mitral valve repair required an extremely invasive surgical approach that includes a sternotomy, cardio-pulmonary bypass, cardiac arrest, and an incision in the heart itself to expose the mitral valve. Such procedure is associated with high morbidity and mortality. A percutaneous device that can effectively treat the disease without the need for open heart surgery could greatly improve patient benefit and may include other patients that previously could not be treated with surgery being too old or frail for such invasive procedure.

Most current surgical practices for mitral valve repair involve mitral valve annuloplasty and/or mitral valve valvuloplasty.

Surgical annuloplasty is a technique aimed to reduce the size of the fibrous tissue at the base of the mitral valve, called the annulus. Sometimes the annulus becomes enlarged, enabling blood to back flow up into the left atrium, through the gap between the two separated valve leaflets. The repair is done with sutures to make the opening smaller, helping the two leaflets meet and co-apt again when the valve closes.

Surgical valvuloplasty is a technique aimed to ensure proper closure of the valve leaflets. Leaflet function can be impaired as the result of prolapse of a leaflet due to ruptured chordae. The leaflet reconstruction is done by leaflet resection and reshaped with sutures. In most cases both annuloplasty and valvuloplasty is needed in order to regain optimal mitral valve function.

Due to the invasive nature of the mitral valve surgery, and the high risks involved in the procedure, many heart failure patients are poor surgical candidates. Thus, less invasive methods and devices to reduce mitral valve regurgitation would make this therapy available to many more patients.

US2004/102839, US2004/1022840, U.S. Pat. Nos. 6,656, 221, 6,718,985, 6,723,038, and US2004/073302 describe minimal invasive approaches to mitral valve annuloplasty, using percutaneous insertion of device into the left ventricle or into the coronary sinus, in order to decrease the annulus size.

U.S. Pat. Nos. 6,626,930 and 6,575,971 disclose a device and method of fastening two pieces of the valve leaflets together, improving competence of the valve.

US2004/243227, US2007/244554, US2008/262609, and US2009/0287304 describe percutaneous devices which attach to the valve annulus via anchoring mechanisms and contract, thereby reducing annulus diameter in a single step.

US2007/016286 discloses a transluminal collapsible heart valve designed to attach to the native annulus of the native regurgitating mitral valve and replace all in a single step. US2012/010700 provides a method for implanting a prosthetic valve apparatus that includes a one way valve and an expandable valve seating. The apparatus is anchored and secured in a newly created orifice near or at the center of the anterior valve leaflet.

Today it is possible to replace an aortic valve (the valve positioned between the left ventricle and aorta) with no surgery through newly developed percutaneous procedures. In these procedures an artificial collapsed valve is delivered through the arteries and positioned inside the diseased native valve, and then expanded to replace it. Following the success of percutaneous replacement of the aortic valve, many attempts have been made to develop similar devices intended for percutaneous treatment of the mitral valve but due to the fact that this valve annulus is much bigger and amorphously shaped, and there are no lumen walls or calcific leaflets that may function as retaining surfaces like in the aortic valve, make it very difficult to prevent dislodgment of a valve expanded into place in the mitral position. Devices that are attached to the mitral annulus and then collapsed to reduce its diameter need to be secured very tightly and accurately to the tissue in order to withhold the high forces that are required to reduce the annulus diameter.

One very promising approach for reinforcing the mitral annulus and replacing the mitral valve is disclosed in WO2013/088327, which is incorporated herein by reference. The present application discloses and claims a number of inventions that build on the disclosure of WO2013/088327 and provides a number of improvements thereon.

SUMMARY OF THE INVENTION

The present invention relates to apparatuses and methods for helping repair or replace biological valves and is particularly suited for cardiac valves, such as the mitral and tricuspid valves.

One aspect of the invention is directed to an apparatus for performing a procedure on a heart valve that has an annulus and leaflets. This apparatus includes a tissue engaging member that has a loop of material configured to contact at least a portion of the annulus or the leaflets when the loop of material is deployed, a plurality of anchors, and a plurality of linking members. Each of the plurality of anchors has a pointy front end and a back end. Each of the plurality of anchors has a slot that runs in a front-to-back direction, wherein the front ends of the plurality of anchors are configured for implantation into the annulus or the leaflets in a forward direction. The plurality of anchors are configured so that subsequent to implantation, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets. The plurality of linking members are affixed to the loop of material, and at least a portion of each of the linking members passes through the slot in a respective anchor. Each of the linking members is configured to slide with respect to the slot in the respective anchor in the front-to-back direction. The apparatus also includes means for implanting the plurality of anchors into the annulus or the leaflets so that the tissue engaging member becomes affixed to the annulus or the leaflets.

In some embodiments, each of the linking members includes a strip of material that passes, through the slot in the respective anchor. Optionally, the strip of material is connected to the loop of material through at least one intermediate member.

In some embodiments, the linking members are disposed inside the loop, and in some embodiments, the linking members are disposed outside the loop.

In some embodiments, the loop of material comprises a closed loop.

Another aspect of the invention is directed to a method for performing a procedure on a heart valve that has an annulus and leaflets. This method includes the steps of delivering a loop of material to the vicinity of the annulus or the leaflets, delivering a plurality of anchors to the vicinity of the annulus or the leaflets, delivering a plurality of linking members that are affixed to the loop of material to the vicinity of the annulus or the leaflets, and implanting the plurality of anchors into the annulus or the leaflets. Each of the plurality of anchors has a pointy front end and a back end. Each of the plurality of anchors has a slot that runs in a front-to-back direction. The front ends of the plurality of anchors are configured for implantation into the annulus or the leaflets in a forward direction. The plurality of anchors are configured so that subsequent to implantation, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets. Each of the linking members passes through the slot in a respective anchor, and each of the linking members is configured to slide with respect to the slot in the respective anchor in the front-to-back direction.

In some embodiments, the linking members are disposed inside the loop. In some embodiments, the linking members are disposed outside the loop.

Another aspect of the invention is directed to an apparatus for performing a procedure on a heart valve that has an annulus and leaflets. This apparatus includes a tissue engaging member that includes a loop of material configured to contact at least a portion of the annulus or the leaflets when the loop of material is deployed, and a plurality of anchors. Each of the plurality of anchors has a pointy front end and a back end. Each of the plurality of anchors has a slot that runs in a front-to-back direction and at least one projection configured to automatically spring outward after being implanted. The front ends of the plurality of anchors are configured for implantation into the annulus or the leaflets in a forward direction. The plurality of anchors are configured so that after the at least one projection in each of the plurality of anchors has sprung outward, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets. The apparatus also includes means for implanting the plurality of anchors into the annulus or the leaflets so that the tissue engaging member becomes affixed to the annulus or the leaflets.

In some embodiments, the at least one projection comprises at least one spring-loaded tab. In some embodiments, the at least one projection comprises at least one arm formed from a shape-memory alloy material.

In some embodiments, the loop of material comprises a loop of wire that passes through the slots in the plurality of anchors, and the slots are configured so that the wire can slide with respect to the slots in the front-to-back direction.

In some embodiments, the apparatus further includes a plurality of linking members that are affixed to the loop of material. Each of the linking members passes through the slot in a respective anchor, and each of the linking members is configured to slide with respect to the slot in the respective anchor in the front-to-back direction.

In some embodiments, the loop of material comprises a closed loop.

Another aspect of the invention is directed to a method for performing a procedure on a heart valve that has an annulus and leaflets. This method includes the steps of delivering a loop of material to the vicinity of the annulus or the leaflets; delivering a plurality of anchors to the vicinity of the annulus or the leaflets; and implanting the plurality of anchors into the annulus or the leaflets. Each of the plurality of anchors has a pointy front end and a back end. Each of the plurality of anchors has a slot that runs in a front-to-back direction and at least one projection configured to automatically spring outward after being implanted. The front ends of the plurality of anchors are configured for implantation into the annulus or the leaflets in a forward direction. The plurality of anchors are configured so that after the at least one projection in each of the plurality of anchors has sprung outward, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets.

Another aspect of the invention is directed to an apparatus for performing a procedure on a heart valve that has an annulus and leaflets. This apparatus includes a tissue engaging member includes a loop of material configured to contact at least a portion of the annulus or the leaflets when the loop of material is deployed, and a plurality of anchors. Each of the plurality of anchors has a pointy front end and a back end. Each of the plurality of anchors includes a first panel of material that has a cylindrically curved outer surface and a second panel of material that has a cylindrically curved outer surface, with a slot that runs in a front-to-back direction disposed between the first panel of material and the second panel of material. The front ends of the plurality of anchors are configured for implantation into the annulus or the leaflets in a forward direction. The plurality of anchors are configured so that subsequent to implantation, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets. The apparatus also includes means for implanting the plurality of anchors into the annulus or the leaflets so that the tissue engaging member becomes affixed to the annulus or the leaflets.

In some embodiments, each of the plurality of anchors further comprises a ring-shaped portion disposed at a back end of the anchor that connects the first panel of material to the second panel of material.

In some embodiments, a front surface of the ring-shaped portion has a notch, and the slot and the notch are disposed on opposite sides of the ring-shaped portion.

In some embodiments, the first panel of material includes at least one barb with an outer surface that follows the cylindrical curve of the outer surface of the first panel of material, and the second panel of material includes at least one barb with an outer surface that follows the cylindrical curve of the outer surface of the second panel of material.

In some embodiments, the first panel of material includes at least one tab with an outer surface that, prior to implantation, follows the cylindrical curve of the outer surface of the first panel of material, and the second panel of material includes at least one tab with an outer surface that, prior to implantation, follows the cylindrical curve of the outer surface of the second panel of material. The tabs automatically spring outward after implantation.

In some embodiments, the loop of material comprises a loop of wire that passes through the slots in the plurality of anchors, and the slots are configured so that the wire can slide with respect to the slots in the front-to-back direction.

In some embodiments, the apparatus also includes a plurality of linking members that are affixed to the loop of material. Each of the linking members passes through the slot in a respective anchor, and each of the linking members is configured to slide with respect to the slot in the respective anchor in the front-to-back direction.

In some embodiments, the loop of material comprises a closed loop.

Another aspect of the invention is directed to a method for performing a procedure on a heart valve that has an annulus and leaflets. This method includes the steps of delivering a loop of material to the vicinity of the annulus or the leaflets; delivering a plurality of anchors to the vicinity of the annulus or the leaflets, and implanting the plurality of anchors into the annulus or the leaflets. Each of the plurality of anchors has a pointy front end and a back end. Each of the plurality of anchors includes a first panel of material that has a cylindrically curved outer surface and a second panel of material that has a cylindrically curved outer surface, with a slot that runs in a front-to-back direction disposed between the first panel of material and the second panel of material. The front ends of the plurality of anchors are configured for implantation into the annulus or the leaflets in a forward direction. The plurality of anchors are configured so that subsequent to implantation, the plurality of anchors resist extraction from the annulus or the leaflets in a backwards direction. The plurality of anchors are arranged with respect to the loop of material so that when the loop of material is deployed the plurality of anchors are distributed about the loop of material with the front ends of the plurality of anchors facing the annulus or the leaflets.

Another aspect of the invention is directed to an apparatus for affixing a loop of material to tissue in a heart. This apparatus includes a housing that has an open front end. The housing has a cylindrical interior void that includes a first section and a second section, and the first section is located in front of the second section. This apparatus also includes an anchor disposed in the first section of the void. The anchor has a pointy front end and a back end, a first panel of material that has a cylindrically curved outer surface, a second panel of material that has a cylindrically curved outer surface, and a slot disposed between the first panel of material and the second panel of material that runs in a front-to-back direction. The front end of the anchor is configured for implantation into the tissue in a forward direction and the anchor is configured so that subsequent to implantation, the anchor resists extraction from the tissue in a backwards direction. This apparatus also includes a spring disposed in the second portion of the void in a compressed state, and an actuator configured to (a) prevent the spring from expanding from the compressed state prior to being actuated and (b) permit the spring to expand from the compressed state upon being actuated. The housing, the spring, the anchor, and the actuator are configured so that when the actuator is actuated, the spring expands into the first section and pushes the anchor forward such that at least a portion of the anchor exits the front end of housing, wherein the spring pushes the anchor with sufficient force to implant the anchor into the tissue.

In some embodiments, the housing has an opening in a sidewall and the actuator comprises a member that has a distal portion. The actuator is configured so that (a) prior to being actuated the distal portion of the member extends into the opening and prevents the spring from expanding from the compressed state and (b) upon being actuated the distal portion of the member is withdrawn from the opening, which permits the spring to expand from the compressed state.

In some embodiments, actuation of the actuator is implemented by pulling the member in a backward direction such that the distal portion of the member is withdrawn from the opening.

In some embodiments, the anchor has a ring-shaped portion disposed at a back end of the anchor that connects the first panel of material to the second panel of material. A front surface of the ring-shaped portion has a notch, and the slot and the notch in the ring are disposed on radially opposite sides of the ring-shaped portion. The anchor is oriented with respect to the housing so that prior to being actuated the distal portion of the member passes through the notch in the ring.

In some embodiments, the housing has an elongated recess at the front end of the housing, and the elongated recess in the housing is aligned with the opening.

In some embodiments, the spring has a back end and the back end of the spring is affixed to the housing.

In some embodiments, the loop of material comprises a closed loop.

Another aspect of the invention is directed to a method for affixing a loop of material to tissue in a heart. This method includes the step of providing a housing that has an open front end. The housing has a cylindrical interior void that includes a first section and a second section. The first section is located in front of the second section. This method also includes the step of disposing an anchor in the first section of the void. The anchor has a pointy front end and a back end, a first panel of material that has a cylindrically curved outer surface, a second panel of material that has a cylindrically curved outer surface, and a slot disposed between the first panel of material and the second panel of material that runs in a front-to-back direction. The front end of the anchor is configured for implantation into the tissue in a forward direction and the anchor is configured so that subsequent to implantation, the anchor resists extraction from the tissue in a backwards direction. This method also includes the steps of disposing a spring in the second portion of the void in a compressed state, and preventing the spring from expanding from the compressed state prior to actuation of an actuator. Then, in response to actuation of the actuator, the spring expands into the first section so that the spring pushes the anchor forward and at least a portion of the anchor exits the front end of housing, wherein the expansion of the spring pushes the anchor with sufficient force to implant the anchor into the tissue.

In some embodiments, actuation of the actuator is implemented by pulling at least a portion of the actuator in a backward direction.

Another aspect of the invention is directed to an apparatus for triggering a plurality of anchor launchers. This apparatus includes a plurality of actuators housed in a housing. Each of the actuators has (a) a channel that runs through the housing in a proximal-to-distal direction, (b) a shoulder disposed adjacent to the channel, (c) a compressed spring disposed in a distal portion of the channel, the spring having a fixed distal end and a movable proximal end, wherein the channel is configured to permit expansion of the spring in a proximal direction, and (d) a tab that is affixed to the proximal end of the spring, wherein the tab is configured to be movable between (i) a first position in which movement of the tab in a proximal direction is blocked by the shoulder, and (ii) a second position in which movement of the tab in a proximal direction is not blocked by the shoulder. The channel, the shoulder, the spring, and the tab are configured so that that when the tab is moved from the first position to the second position, the spring will expand within the channel, with the proximal end of the spring moving in a proximal direction. Each of the actuators also has a pull wire that has a proximal end that is attached to the spring or the tab and a distal portion that extends to the anchor launcher, wherein when the proximal end of the spring moves in the proximal direction, the pull wire is pulled in the proximal direction.

In some embodiments, the housing is cylindrical, the channels are distributed within the cylindrical housing, and the tabs extend outside a circumference of the cylindrical housing.

In some embodiments, the apparatus further includes a rotatable cap, wherein an interior surface of the cap defines a cylindrical void configured to surround the cylindrical housing, and the interior surface has a single protrusion configured to sequentially push each of the tabs from the first position to the second position when the cap is rotated.

In some embodiments, the apparatus further includes a rotatable cap, wherein an interior surface of the cap defines a cylindrical void configured to surround the cylindrical housing, and the interior surface has a plurality of protrusions configured to simultaneously push a plurality of the tabs from the first position to the second position when the cap is rotated.

In some embodiments, the proximal end of the pull wire is affixed directly to the spring or the tab.

Another aspect of the invention is directed to a method for triggering a plurality of anchor launchers. This method includes the step of providing a plurality of actuators housed in a cylindrical housing. Each of the actuators has (a) a channel that runs through the housing in a proximal-to-distal direction, (b) a shoulder disposed adjacent to the channel, (c) a compressed spring disposed in a distal portion of the channel, the spring having a fixed distal end and a movable proximal end, wherein the channel is configured to permit expansion of the spring in a proximal direction, and (d) a tab that is affixed to the proximal end of the spring, wherein the tab is configured to be movable between (i) a first position in which movement of the tab in a proximal direction is blocked by the shoulder, and (ii) a second position in which movement of the tab in a proximal direction is not blocked by the shoulder. The channel, the shoulder, the spring, and the tab are configured so that that when the tab is moved from the first position to the second position, the spring will expand within the channel, with the proximal end of the spring moving in a proximal direction. Each of the actuators also has a pull wire that has a proximal end that is attached to the spring or the tab and a distal portion that extends to the anchor launcher, wherein when the proximal end of the spring moves in the proximal direction, the pull wire is pulled in the proximal direction. The channels are distributed within the cylindrical housing, and the tabs extend outside a circumference of the cylindrical housing. This method also includes the step of providing a rotatable cap configured so that an interior surface of the cap defines a cylindrical void configured to surround the cylindrical housing. The interior surface has at least one protrusion configured to push each of the tabs from the first position to the second position when the cap is rotated.

In some embodiments, the at least one protrusion is configured to sequentially push each of the tabs from the first position to the second position when the cap is rotated.

In some embodiments, the at least one protrusion comprises a plurality of protrusions configured to simultaneously push a plurality of the tabs from the first position to the second position when the cap is rotated.

BRIEF DESCRIPTION OF THE DRAWINGS

FIGS. 11 and 12 are perspective views of an exemplary delivery system for the present device.

FIGS. 23-27 and 27A are perspective views of further embodiments of anchor launching mechanisms.

FIGS. 29-34 are perspective views of implant deployment mechanisms.

FIGS. 35-39 are perspective views illustrating the device in use in conjunction with an implantable device.

FIGS. 44-47 depict views of an exemplary embodiment used for implementing cinching.

FIGS. 57A, 57B, and 57C depict yet another embodiment of an anchor in a launching mechanism.

Figure 1:
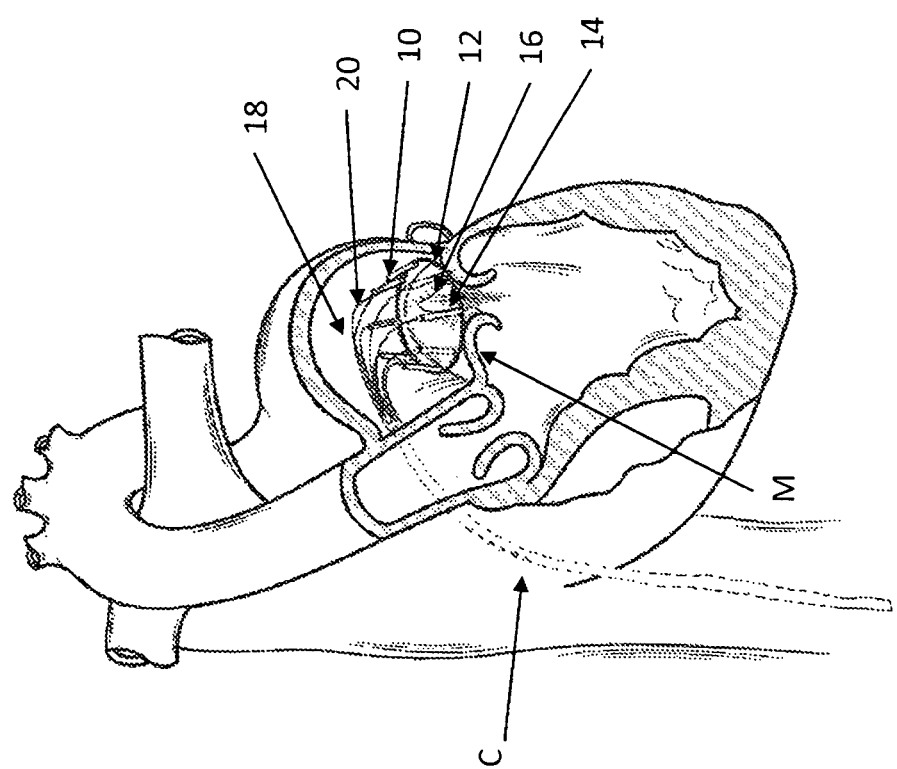
FIG. 1 is a front partial cut-away view of an embodiment of a heart valve repair device of the present invention.

The following description of preferred embodiments refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DESCRIPTION OF THE PREFERRED EMBODIMENTS

A heart valve repair device comprising an implant and delivery system is delivered into the heart in four sequential stages: In the first stage the implant and support scaffold are advanced in a collapsed configuration inside a capsule through the vascular system to the valve annulus (preferably the Mitral annulus but can be also the Tricuspid annulus). In the second stage after positioning the capsule close to the annulus a support scaffold is pushed outside of the capsule and the implant which is attached to the scaffold is spread into a round or D shape circumferential ring onto the valve annulus in 3 optional ways: 1) On the inflow side of the valve with attachment anchors pointing from the atrium side to the ventricle side; 2) On the inflow side of the valve with attachment anchors pointing from the ventricle side to the atrium side; and 3) On the outflow side of the valve with attachment anchors pointing from the ventricle side to the atrium side.

In the third stage after the implant is spread out, all the anchors are launched into the tissue at once or in a sequential manner and affix the implant to the tissue. The same action also separates the implant from the support scaffold and delivery system. In the fourth stage the scaffold is retracted and collapsed back into the delivery capsule and the delivery system is withdrawn out of the body.

It is important to note that in some embodiments the spread implant conforms at least partially to the valve annulus shape, and in some embodiments the spread implant does not conform at all to the valve annulus shape, but is just affixed to the valve leaflets and is retained there for a few minutes until a valve prosthesis is deployed into it as will be described later on.

After the implant is attached to the valve tissue it is possible to treat the valve insufficiency in 5 optional ways: 1) By direct annuloplasty which impose cinching of the implant attached to the valve annulus, hence reducing the annulus diameter and improving valve leaflets coaptation; 2) By restricting annulus dilatation over time due to the constant perimeter of the implant which is attached to the valve annulus and gets embedded into the tissue over time through tissue growth; 3) By facilitating a support ring for valve prosthesis to be implanted at a later procedure after the implant which is attached to the valve annulus gets embedded into the tissue over time through tissue growth; 4) By performing annuloplasty at a later stage in a different procedure weeks or months later after the implant which is attached to the valve annulus gets embedded into the tissue over time through tissue growth; and 5) By facilitating a support ring for valve prosthesis that can be implanted into the ring during the same procedure right after the ring is attached to the valve leaflets.

Illustrative embodiments of the invention are described below. In the interest of clarity, not all features/components of an actual implementation are necessarily described.

FIG. 1 shows an embodiment of a mitral valve adjustment/repair implant 10 of the present invention, implanted onto a bio-valve, exemplified by mitral valve M of the heart. Implant 10 comprises: a tissue engaging member 12, comprising a loop 14 of wire and a plurality of tissue anchors 16 associated with the loop and having and an elongated slot 17 (FIG. 5); a scaffold or implant positioning device 18, in this embodiment comprising plurality of support arms 20; and an anchor launching mechanism 22 (FIGS. 2-7). Implant 10 is typically positioned in proximity of the mitral valve M via a delivery catheter C. The loop 14 of wire is preferably made of metal wire, but in alternative embodiments the wire may be a non-metallic material. Note that as used herein, "wire" includes metal and/or non-metallic materials. In alternative embodiments the loop of wire may be replaced by a different loop of material such as a tube, strip, chain, braid, etc. Optionally, a wire may be disposed within the different loop of material.

Figure 2:
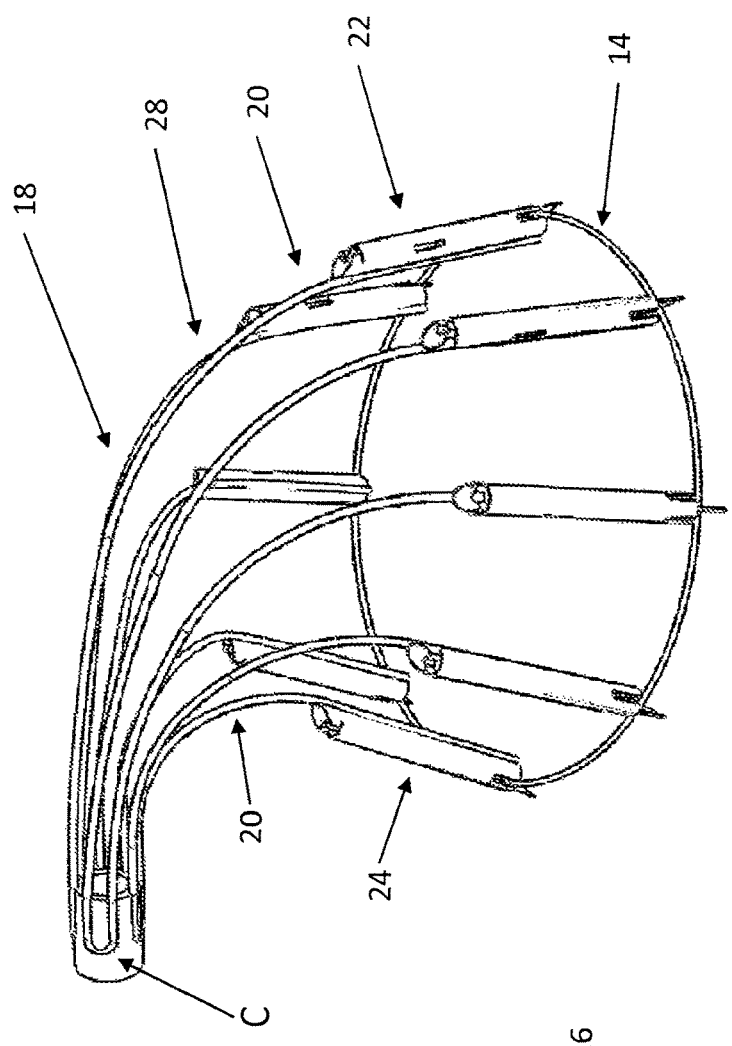
FIG. 2 is an enlarged perspective view of the device of FIG. 1.
Figure 3:
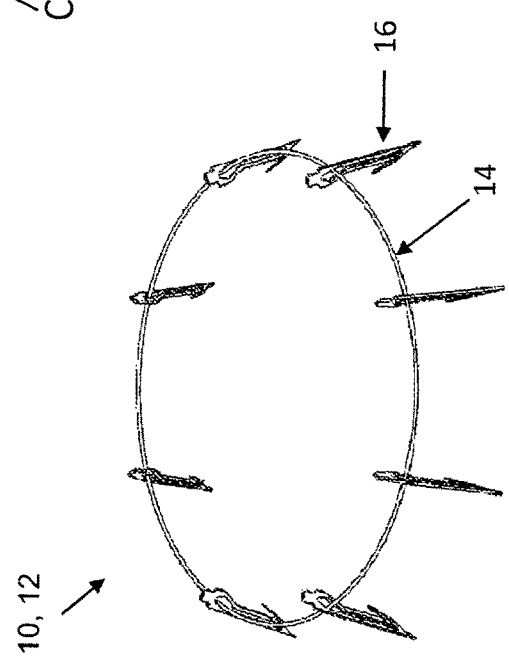
FIG. 3 is a perspective view of an implant or tissue engaging member of the present device.

FIG. 2 shows an enlarged view of the device in FIG. 1 illustrating anchor launching mechanism 22 in a ready for deployment (launching) and deployed state, respectively; Elongated slot 17 of anchors 16 allow loop 14 to be retained by (operably attached to) the anchors—which will be explained further herein below. FIG. 3 shows an embodiment of implant 10 in its configuration when implanted, as will be discussed further below.

Figure 5:
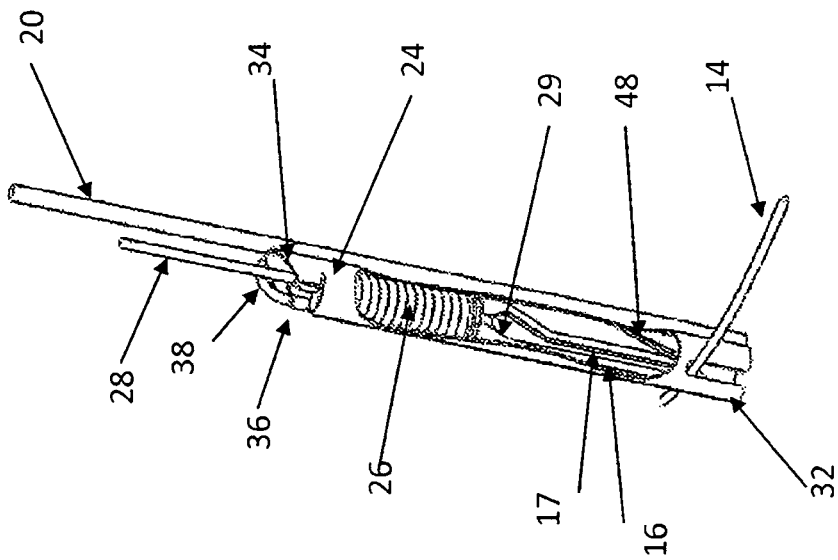
FIGS. 4-6 are perspective views of an anchor launching mechanism of the device of FIG. 1.
Figure 4:
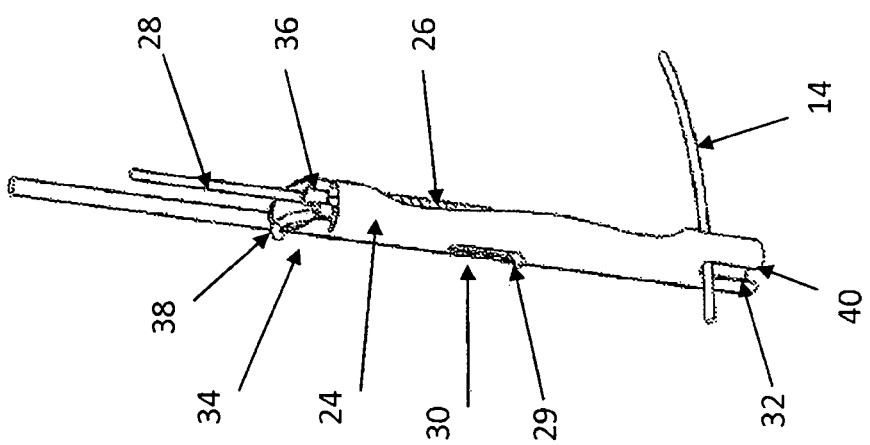
Figure 6:
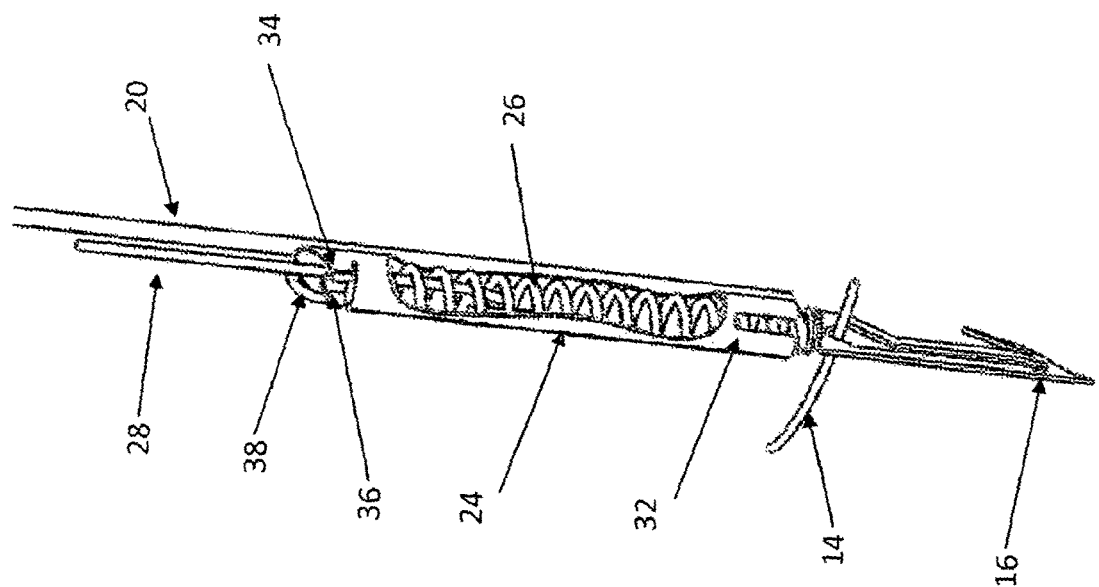

FIGS. 4-6 show details of anchor launching mechanism 22, which comprises a housing 24, typically cylindrical; an anchor launching biasing mechanism, such as coil spring 26 disposed within the housing; and a spring actuator wire 28, having a bent distal end 29, passing through elongated slot 17 and protruding through an opening 30 of housing 24. Bent distal end 29 maintains spring 26 is a compressed configuration. Actuator wire 28 passes longitudinally/coaxially through coil spring 26. Implant support arms 20 are respectively attached to housings 24, for example by welding. It should be noted that actuator wire 28 can be made of any appropriate material and is not limited to metal.

Housing 24 has an open end 32 and a spring retention end 34, which in some embodiments comprises a crimped portion 36 or other such spring retention mechanism, to provide a launching base for spring 26. In some embodiments, to prevent spring 26 from being ejected from (falling out of) housing 24, spring has a hooked proximal end 38 adapted to hook at retention end 34 of the housing. As can be seen, loop 14 is threaded through each elongated slot 17 of tissue anchors 16. As best seen in FIG. 4, in some embodiments, housing 24 has a pair of elongated recesses 40 at open end 32 whereby loop 14 can pass. FIGS. 4 and 5 show anchors 16 in a pre-launch state where spring 26 is compressed, and FIG. 6 shows the anchors in a launched state with the spring in its normally expanded configuration.

As shown, tissue anchors 16 are typically spaced apart all along loop 14 and loop 14 is threaded through elongated slot 17, allowing the tissue anchor to move (be launched), typically more or less perpendicular (although in some embodiments at an angle) with respect to the loop. It should be noted that loop 14 can be made of any appropriate material and is not limited to metal. Note that while eight anchors are depicted in all the illustrated embodiments, the number of anchors can be varied. Preferably at least six anchors are used.

Figure 7A:
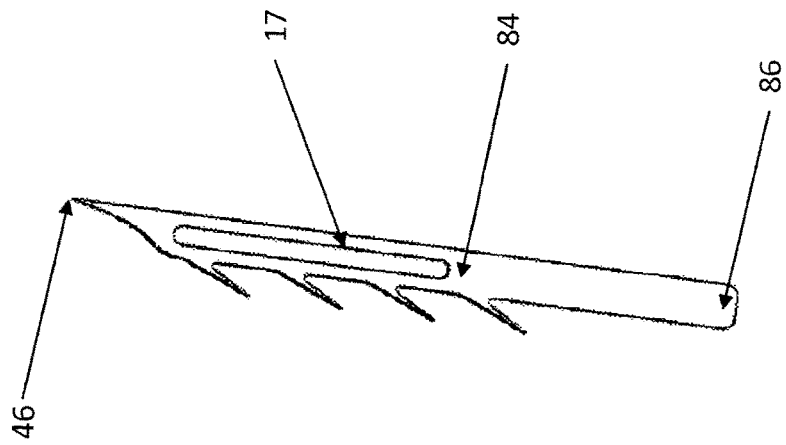
FIGS. 7 and 7A are perspective views of anchors of the present device.
Figure 7:
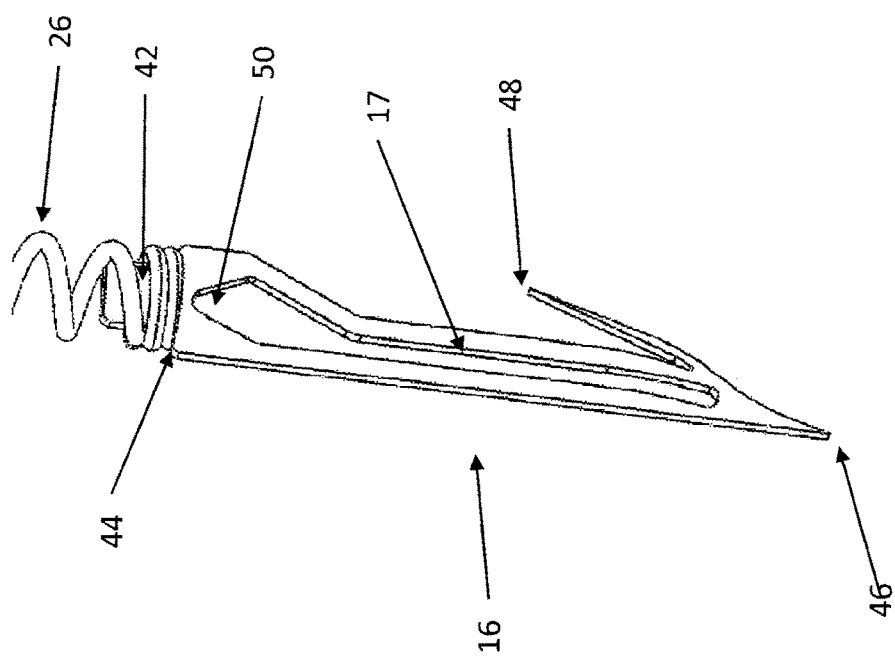

With reference to FIG. 7, in some embodiments, each anchor 16 has a proximal portion 42 including a spring interfacing portion exemplified by a pair of flat shoulders 44. Anchors 16 also have a pointy front end 46, typically with one or more barbs 48. After an anchor is implanted in the forward direction, the barbs 48 resist extraction of the anchor 16 in a backwards direction. In some embodiments, elongated slot 17 has a relatively large or bulbous open portion or eyelet 50 adjacent proximal portion 42, which can be useful to provide additional space for bent distal end 29 to pass through the elongated slot along with loop 14.

Figure 8:
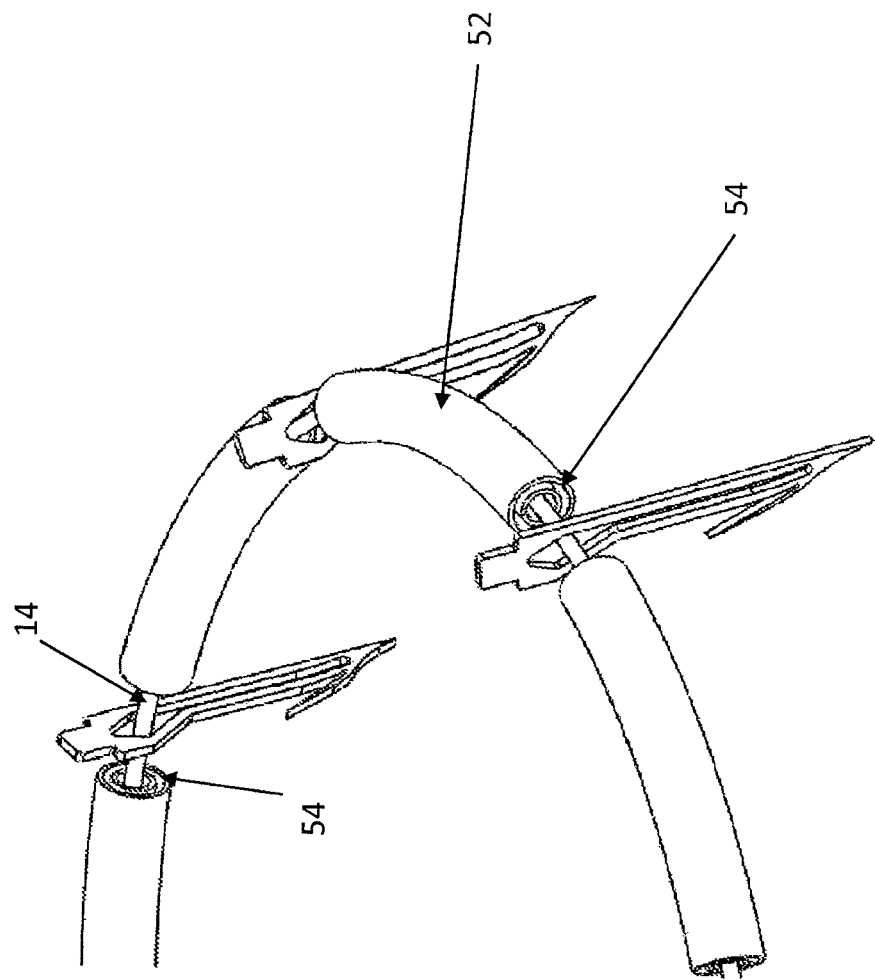
FIGS. 8-10 are perspective views of another embodiment of the tissue engaging member.
Figure 9:
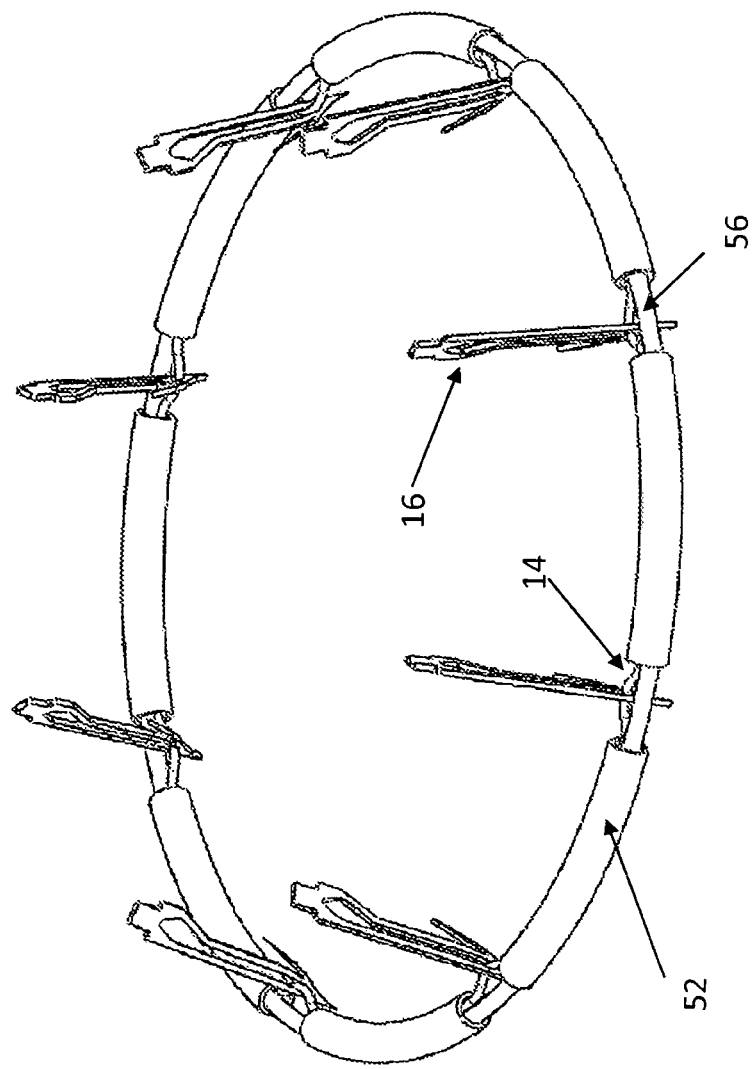
Figure 10:
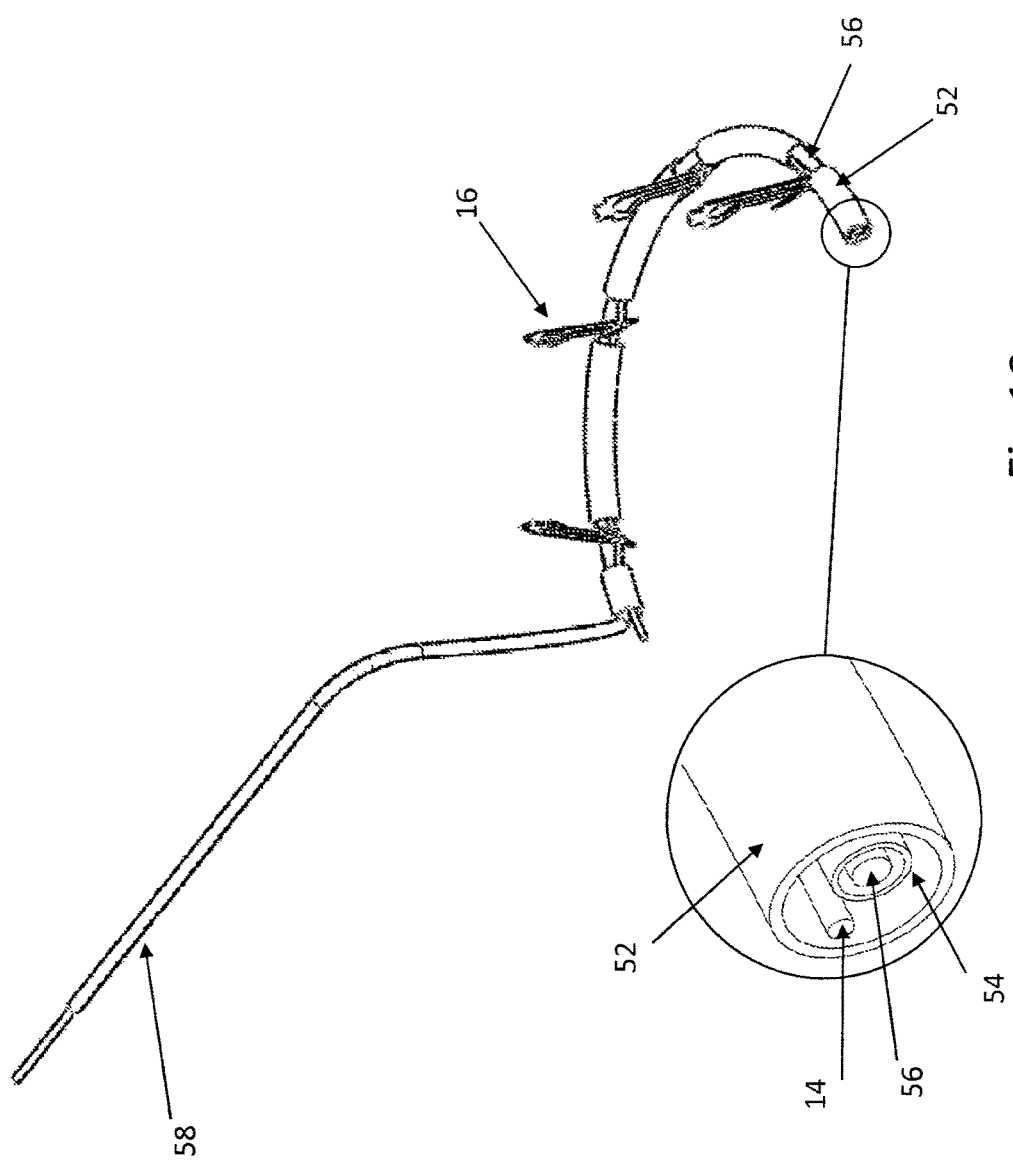

FIGS. 8-10 shows a modification of the implant wherein loop 14 has a plurality of tissue growth-promotion tubes 52 coaxially surrounding the loop 14 between anchor positions. In some embodiments, tissue growth-promotion tubes 52 have respective tissue growth inhibiting liners or surfaces 54 (FIG. 10). Tissue growth-promotion tubes 52 are made of a material and/or substance adapted to promote and facilitate the growth of tissue thereon, for example an appropriate fabric or coating. If indeed in the form of liners, tissue growth inhibiting liners 54 are disposed tissue growth-promotion tubes 52, e.g. coaxially, and include tissue growth inhibiting material/substance.

FIGS. 9 and 10 additionally show another embodiment wherein there are two loops, the aforementioned loop 14 and a relatively sturdy auxiliary loop 56 to provide additional robustness to the implant if so desired. FIG. 10 shows a modification wherein auxiliary loop further includes a proximal portion 58 that can be used to position the implant 10, in addition to or in place of the above mentioned implant positioning device 18.

Operation: implant 10 is deployed to a position adjacent the bio-valve (e.g. Mitral valve M) via/through delivery catheter C (see FIGS. 11 and 12; and also FIGS. 1 and 2). When implant 10 is appropriately located, using support arms 20 and\or auxiliary loop 56 with its proximal portion 58, actuator wire 28 of each anchor launching mechanism 22 is retracted thereby withdrawing their bent distal ends 29 from respective openings 30 of housings 24. As a result, springs 26 are released from their compressed state to their expanded state thereby launching tissue anchors 16 into the bio-valve tissue. Typically, pointy end 46 of each anchor 16 enters the tissue, and barbs 48 help to prevent inadvertent detachment of the anchors.

Figure 13:
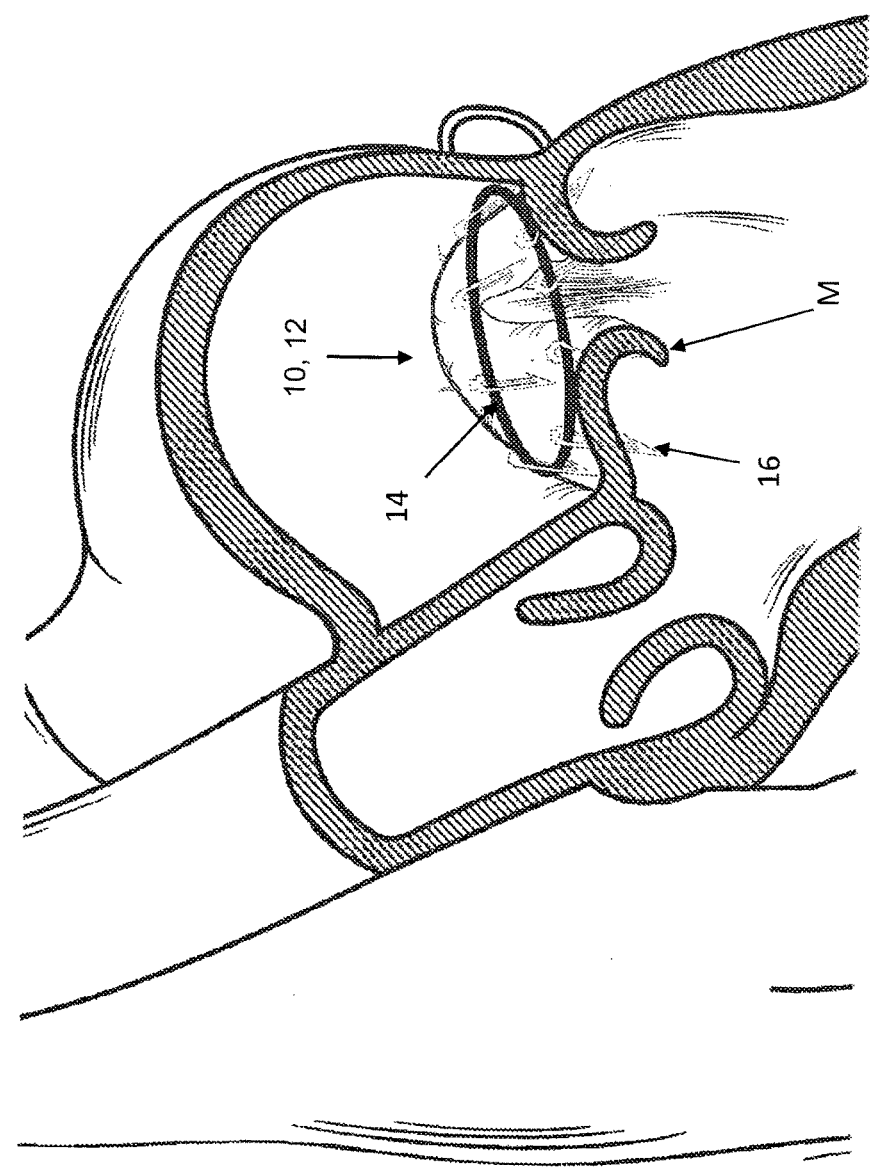
FIG. 13 is a front partially cut-away view of a heart with the implant affixed to a mitral valve from above the valve.

FIG. 13 illustrates implant 10 connected to the tissue of mitral valve M of the heart after the launching of tissue anchors 16 into the tissue. Implant 10 is positioned on the top of the mitral valve M, as a result of being inserted into the heart in a manner such as shown in FIG. 1, and anchors 16 face generally downward. After the implantation natural tissue growth start to occur all around the parts of implant 10 that are within the tissue notably the anchors, and later on tissue growth will cover also parts of the implant at close proximity to the tissue surface. When tissue growth fills the anchors slot 17 they become mechanically locked within the tissue, and over time the entire implant 10 will get embedded in the valve annulus tissue. Since the implant is largely comprised of loop 14 which is made of non-elastic substance, further annulus dilatation over time due to progression of the valve regurgitation disease is prevented.

Figure 14:
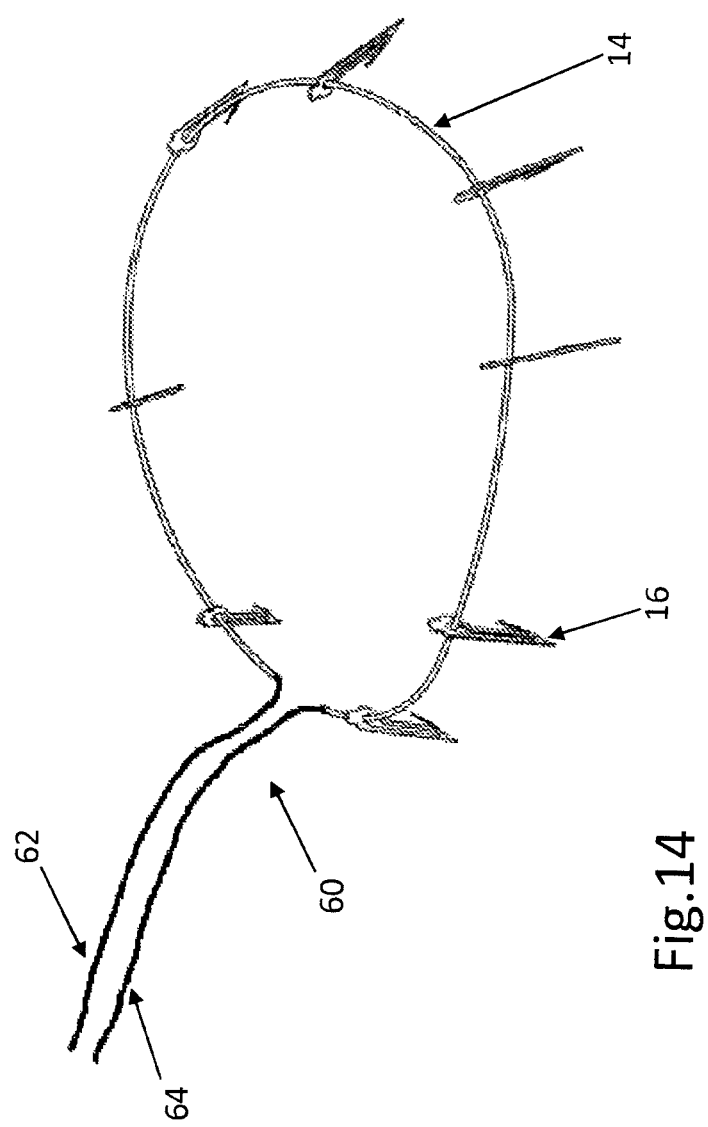
FIG. 14 is a perspective view of a cinching mechanism of the device.

With reference to FIG. 14, in some embodiments, the implant further comprises a cinching mechanism 60, for example wherein loop 14 is not in a closed loop configuration rather has generally adjacent free ends 62 and 64. The ring-like portion of loop 14 passes through elongated slots 17 of anchors 16 (and in suitable embodiments, through tissue growth-promotion tubes 52), as before. After sufficient tissue grows on implant 10, which typically takes one week to several months, depending on the tissue growth rate, the implant may be cinched via pulling on one or both of the free ends 62 and/or 64 to reduce the diameter of tissue engaging member 12, (however, in some implementations of the operation, cinching action is not required, and could be excluded from procedure). Free ends 62 and 64 may extend outside the patient's body or remain under the skin at the upper portion of the chest, much like pace maker leads. The tissue growth causes implant 10 to be embedded and integrated to the valve annulus. In addition, tissue growth within elongated slot 17 helps secure anchors 16 and prevents the implant from being dislodged from the valve annulus.

FIG. 14 further illustrates a D-shaped loop 14, in contrast to the circular or oval shaped loops illustrated in the aforementioned figures. D-shaped loop 14 is particularly suited for use with a human mitral heart valve. In this regard, it should be understood that loop 14 can be configured by choice or design to appropriately correspond to the particular bio-valve for which repair is required.

Figure 15:
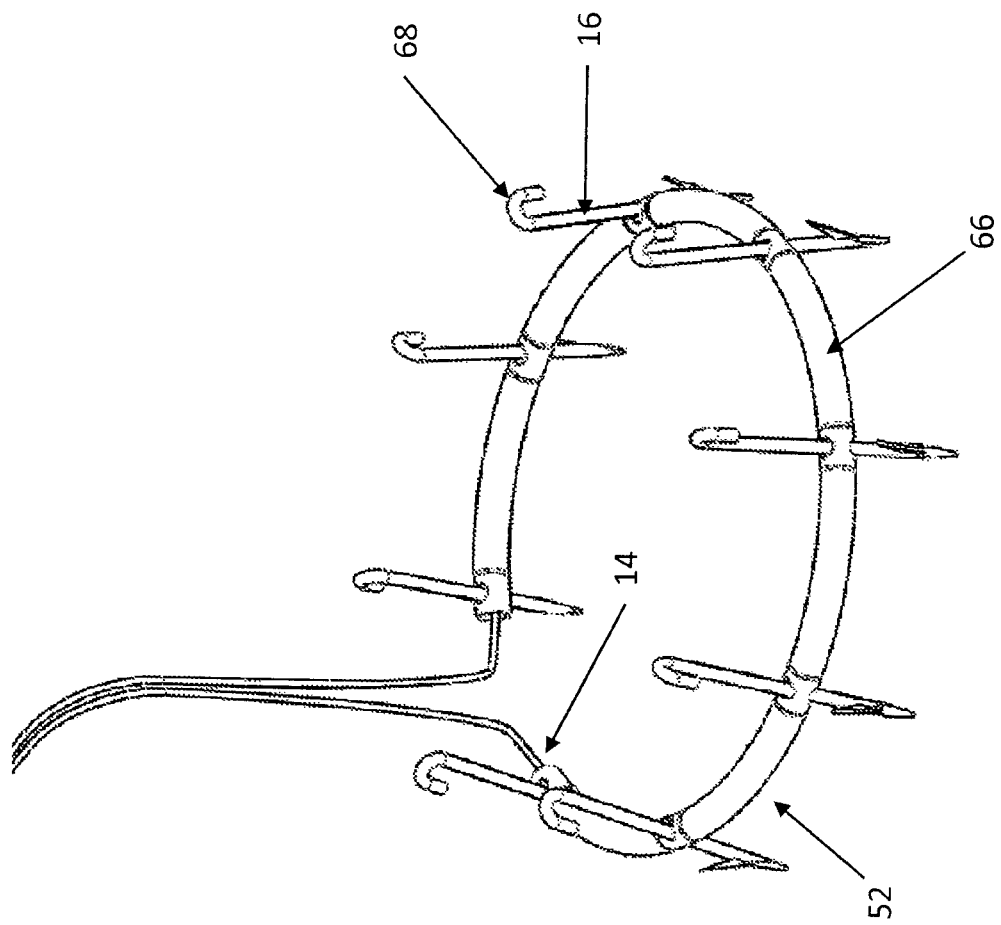
FIGS. 15-17 are perspective views of additional embodiments of anchors.

FIG. 15 shows another embodiment wherein instead of anchors 16 engaging loop 14 via elongated slot 17, the anchors pass thru a coaxial tube 66 coaxially surrounding the loop—the tube could be, for example a tissue growth promotion tube such as tissue growth-promotion tubes 52. Retention of anchors 16 with coaxial tube 66 is aided by a retention hook 68 at the proximal end of the anchors.

Figure 17:
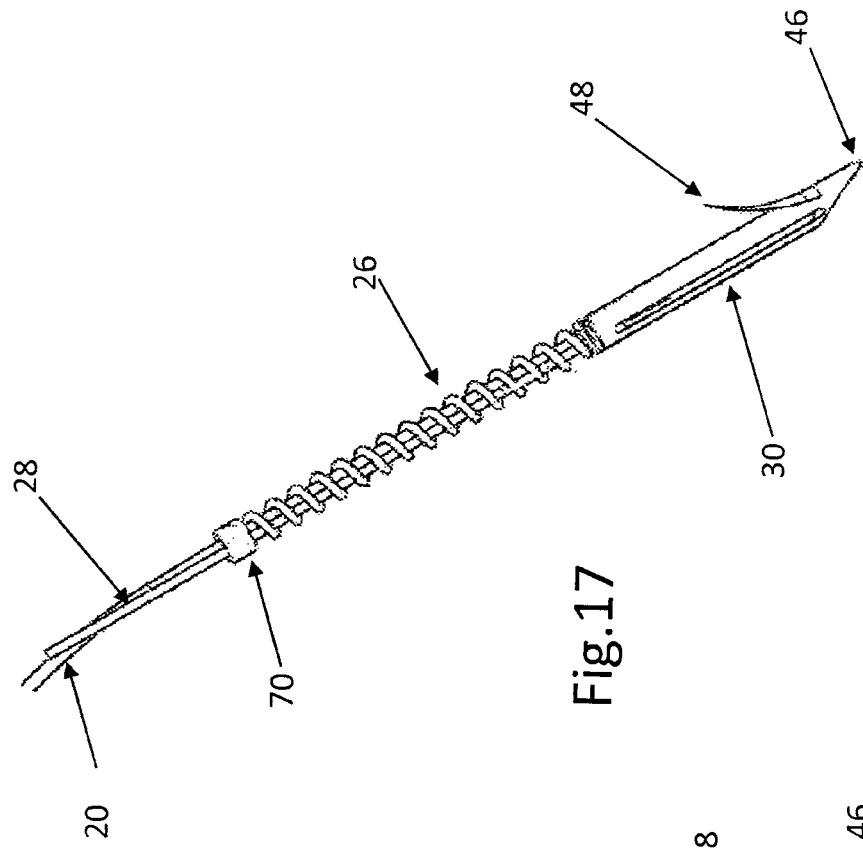
Figure 16:
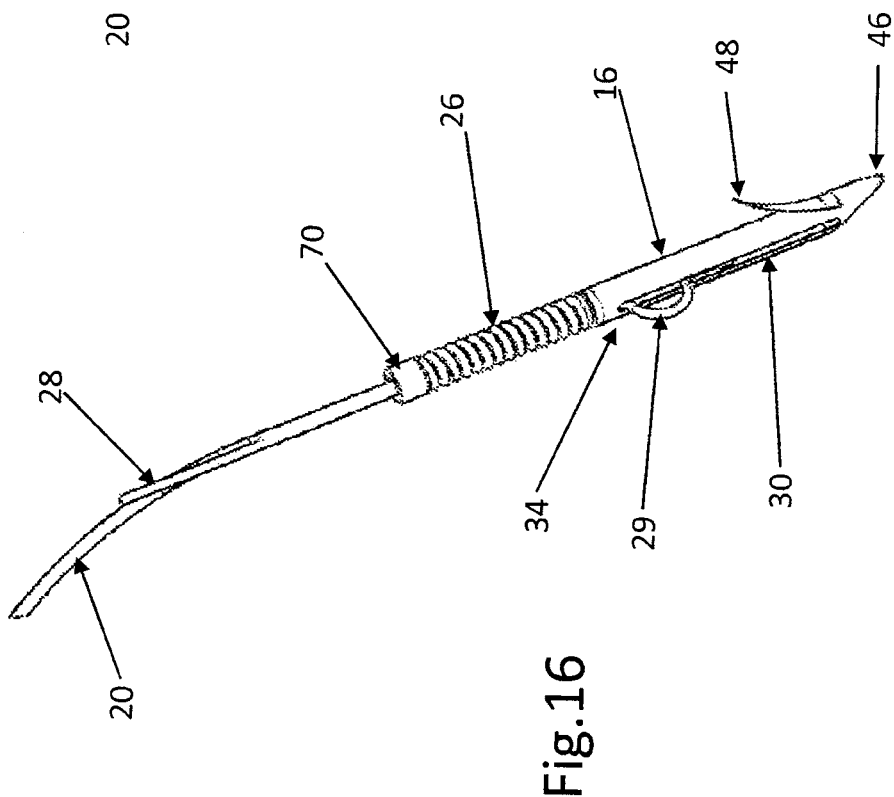

FIGS. 16 and 17 depict an embodiment where anchor 16 has a cylindrical shape, similar to housing 24 and no such housing is required. In this case spring 26 is held in compression between end 34 of cylindrical anchor 16 and a spring launching base, exemplified by a launching base ring 70, attached to implant support arms 20. End 34 now provides the function of the aforementioned flat shoulders 44; and launching base ring provides the function of the aforementioned crimped portion 36. When actuator wire 28 is retracted, its bent distal end 29 (here, illustrated in the form of a half-loop) is retracted from opening 30 thereby releasing cylindrical anchor 16 so that spring 26 expands to launch the anchor.

Figure 19:
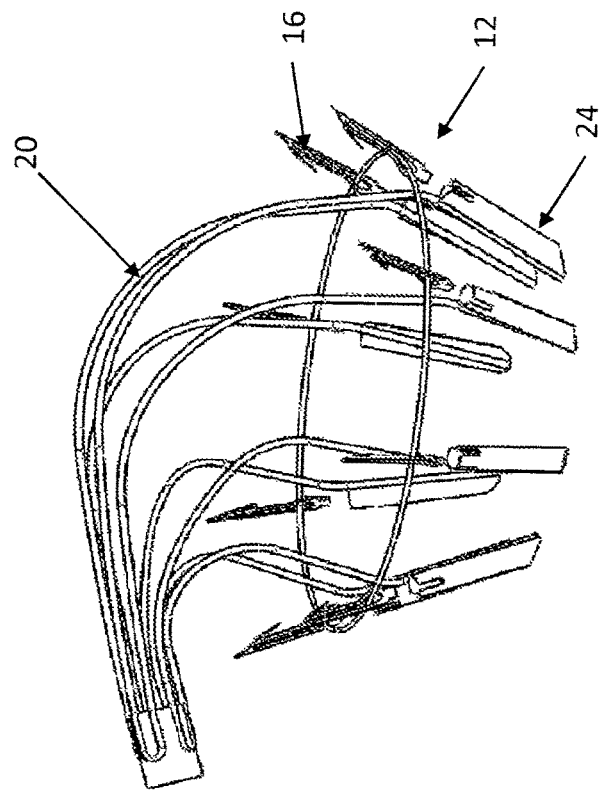
FIGS. 18 and 19 are perspective views of embodiments of anchor launching mechanisms.
Figure 18:
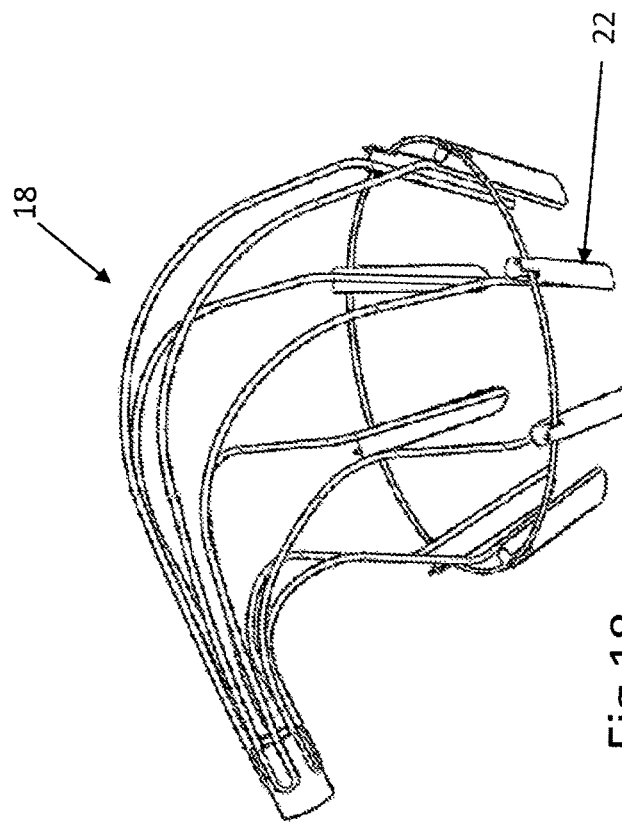

FIGS. 18 and 19 shows implant positioning device 18 configured, mutatis mutandis, wherein anchor launching mechanism 22 is adapted to launch anchors 16 into the tissue in a generally upward direction (i.e. from the ventricle side to the atrium side). This embodiment is particularly useful in the case where the tissue engaging member 12 serves as a support to prevent dislodgement of a valve prosthesis that can be expanded into it right after the tissue engaging member 12 has been deployed.

Figure 20:
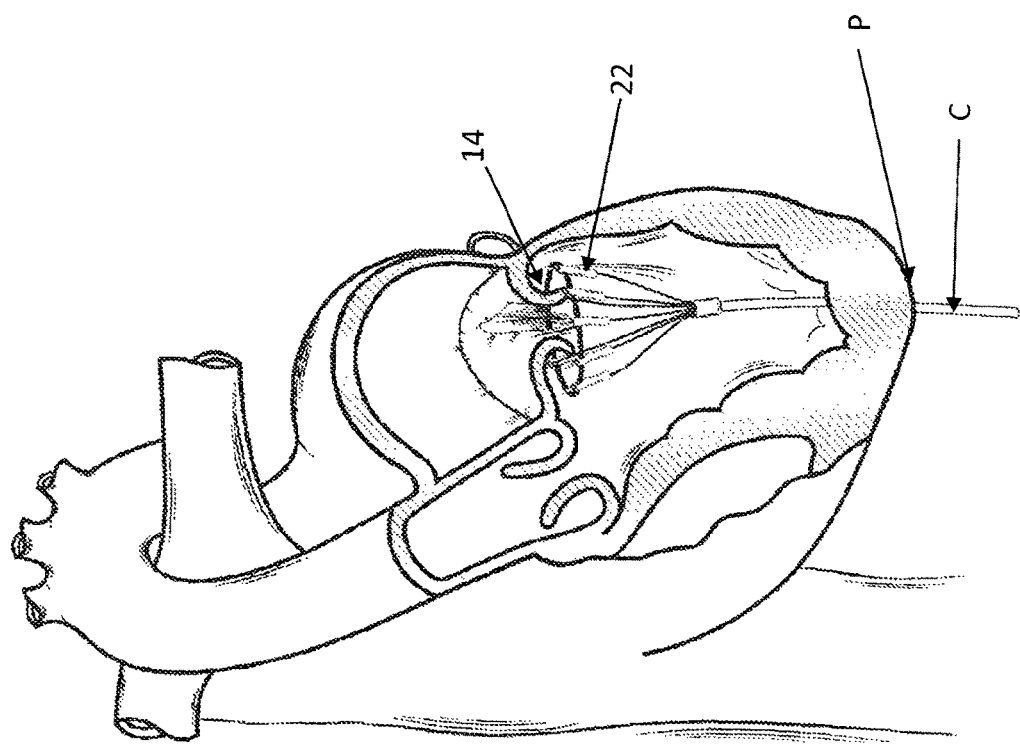
FIGS. 20-22 are front partially cut-away views of a heart with the implant affixed to a mitral valve from below the valve.
Figure 21:
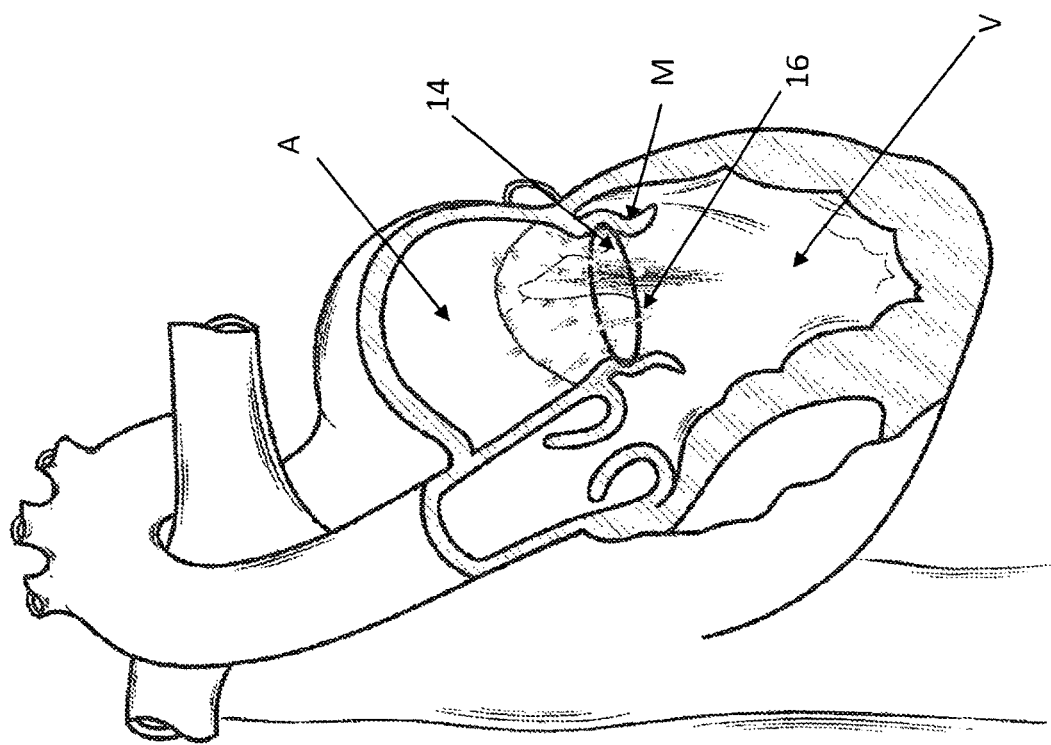
Figure 22:
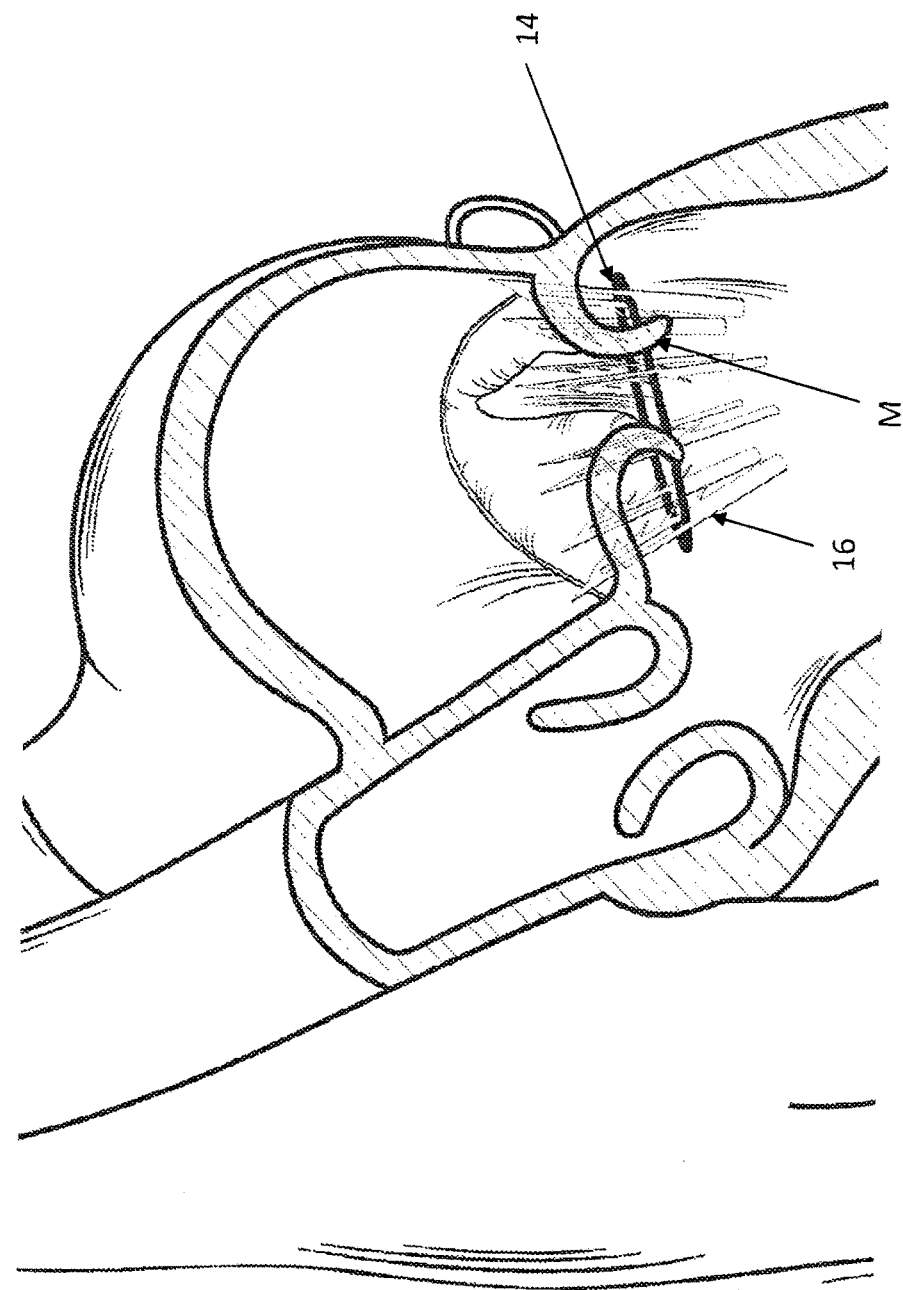

FIGS. 20-24 illustrate embodiments adapted for situations where launching anchors 16 upwardly may also be used in cases where access to the insufficient valve is from below, for example via the Apex (see FIG. 20), is preferable rather than from above. FIGS. 20 and 22 show loop 14 disposed under the Mitral valve leaflets and FIG. 21 shows loop 14 disposed onto the Mitral valve leaflets M as the anchors 16 penetrates through the leaflets pointing from the ventricle side to the atrium side.

Figure 23:
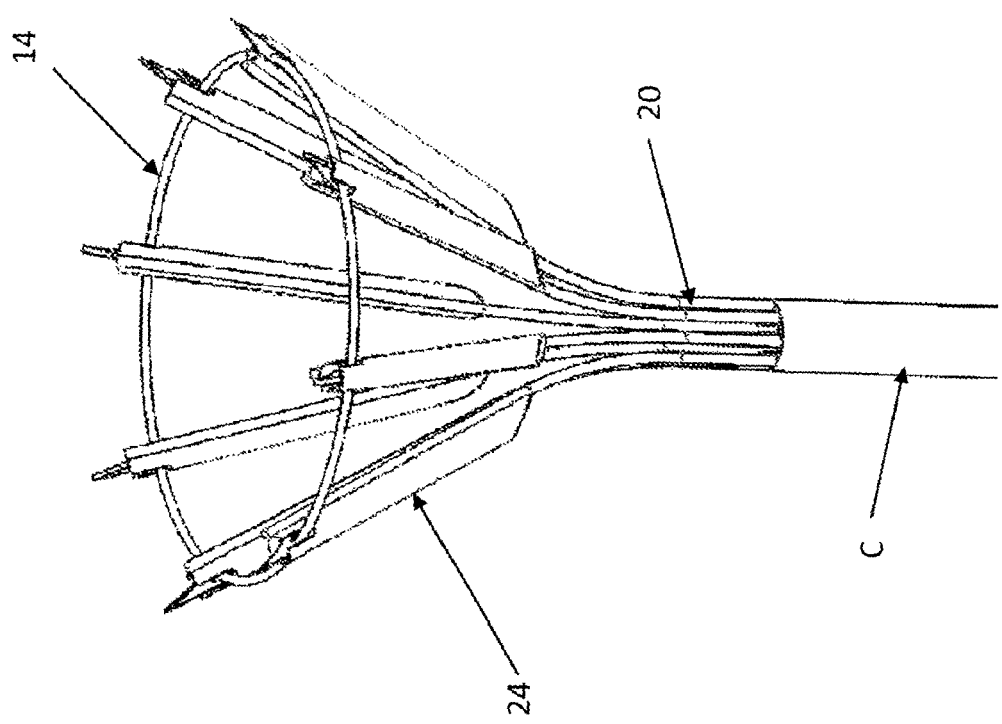
Figure 24:
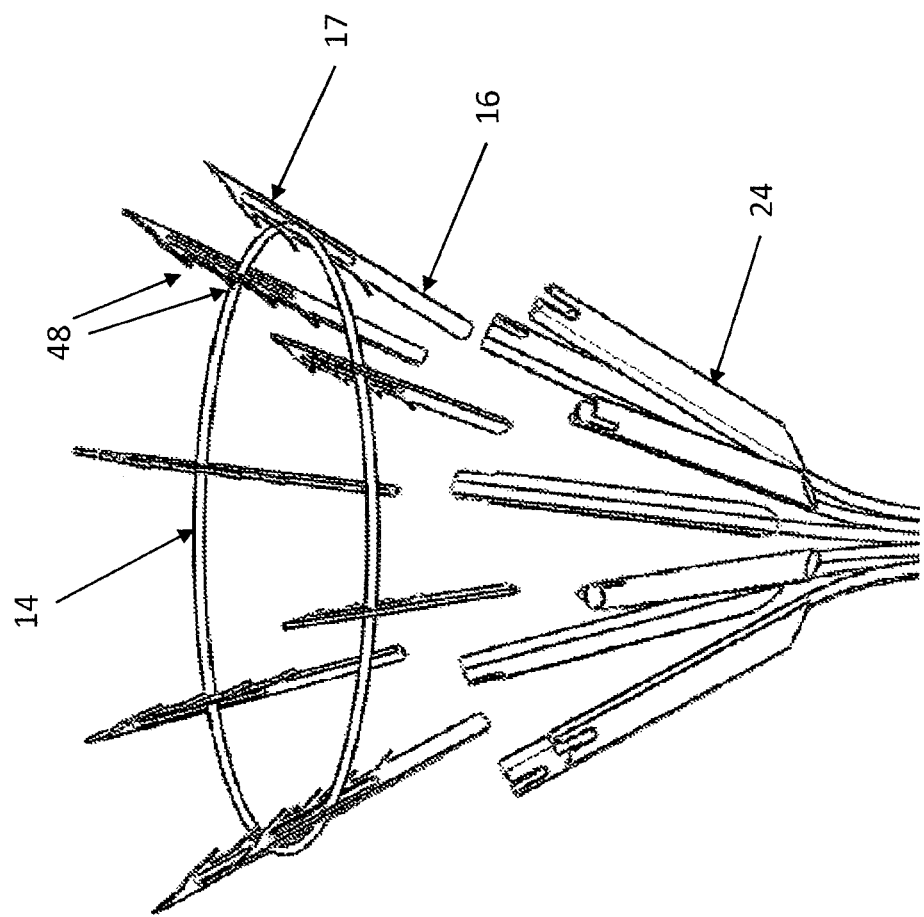

FIGS. 23 and 24 show the pre-launch and launch situations for upward launching of anchors 16. FIG. 23 further illustrates that catheter C can be used to help orient the angle of housings 24, and thus the launch angle of anchors 16. If the distance between catheter C and loop 14 is relatively small, anchors 16 tends to be positioned and launched at a greater angle (relative to being launched perpendicular to loop 14, as was shown in FIGS. 2 and 3, for example). Adjustment of the launch angle, i.e. pivoting of anchors angle, is made possible by the shape of the support arms 20 to which the housing 24 is attached. FIG. 24 also illustrates another modification wherein anchors 16 comprise multiple barbs 48 and wherein elongated slot 17 extends about half-way within the length of the anchors, as seen in FIG. 7A.

FIGS. 25-27 and 27A illustrate particular embodiments wherein anchor launching mechanism 22 is adapted to be used with tissue anchors 16 that are launched in a generally upward direction; and can be actuated by a direct pull, or by a mechanism removed from the valve area. Anchor launching mechanism 22 comprises actuation wire 28 and housing 24, however the mechanism does not include spring 26 disposed in the housing. Regardless, for rapid actuation purposes (anchor launch), anchor launch mechanism 22 may further include an external launch actuator device, typically including a spring (not shown), for example, at the proximal end of catheter C, to pull on actuation wire 28. When the catheter approaches from the inflow side of the valve, and routes the anchors so that they are below the valve with the tip directed from the ventricle side to the atrium side, this configuration and approach to the valve permits pull wires to be used.

Figure 26:
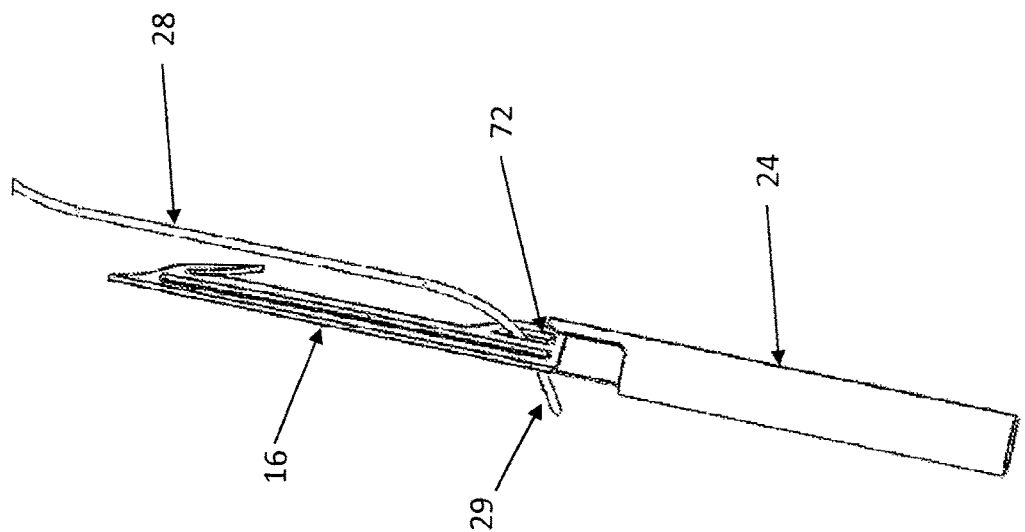
Figure 25:
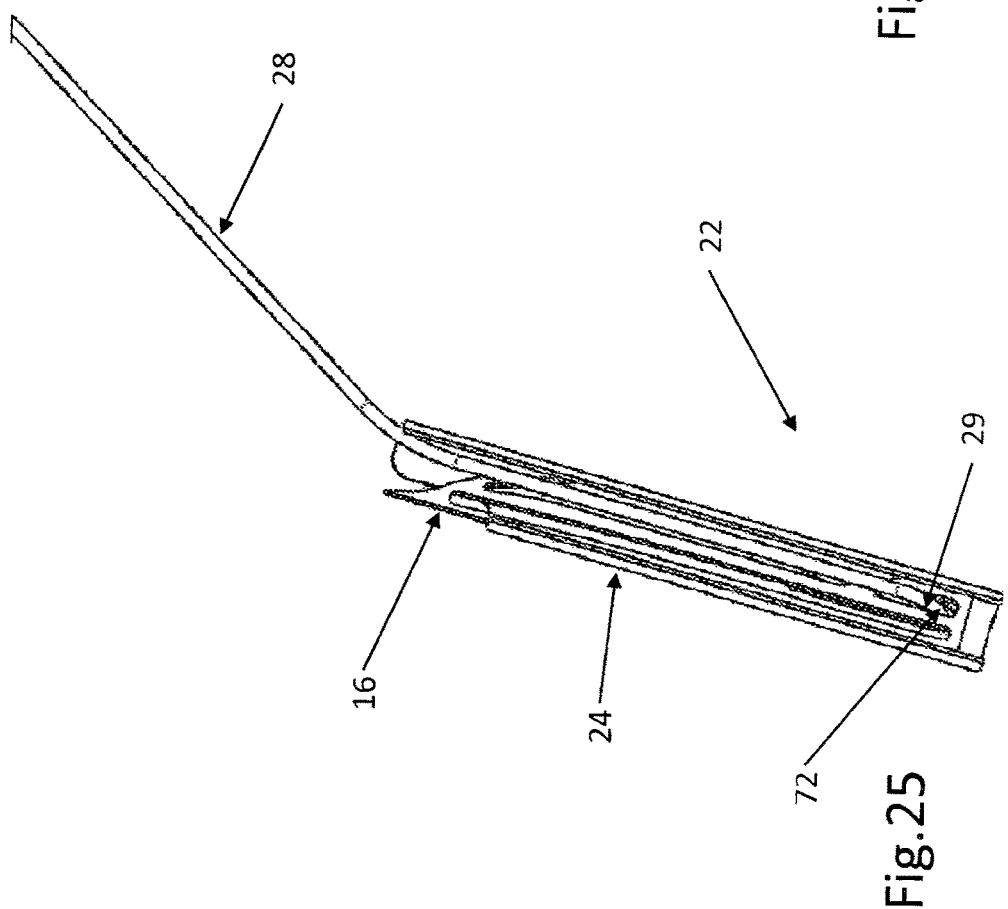

For the purposes of these embodiments, anchor 16 may be modified to further comprise an actuation wire eyelet 72 where-through actuation wire 28. Distal end 29 of actuation wire 28 is threaded through eyelet 72 and typically has a hook-like configuration while disposed within housing 24 (FIGS. 25 and 27). Pulling on actuator wire 28 proximal end to pull (launch) anchor 16 as a result of pulling at eyelet 72 (FIG. 26). In such embodiments, housing 24 need not include an opening such as opening 30, nor does not need a crimped portion 36 or other such spring retention mechanism, as there is no spring in the housing. FIGS. 27 and 27A illustrates a modification wherein instead of eyelet 72; each anchor 16 has an actuator-wire distal-end receiving portion such as recess 74, which operates to launch anchors 16 in the same fashion as noted above.

Figure 28:
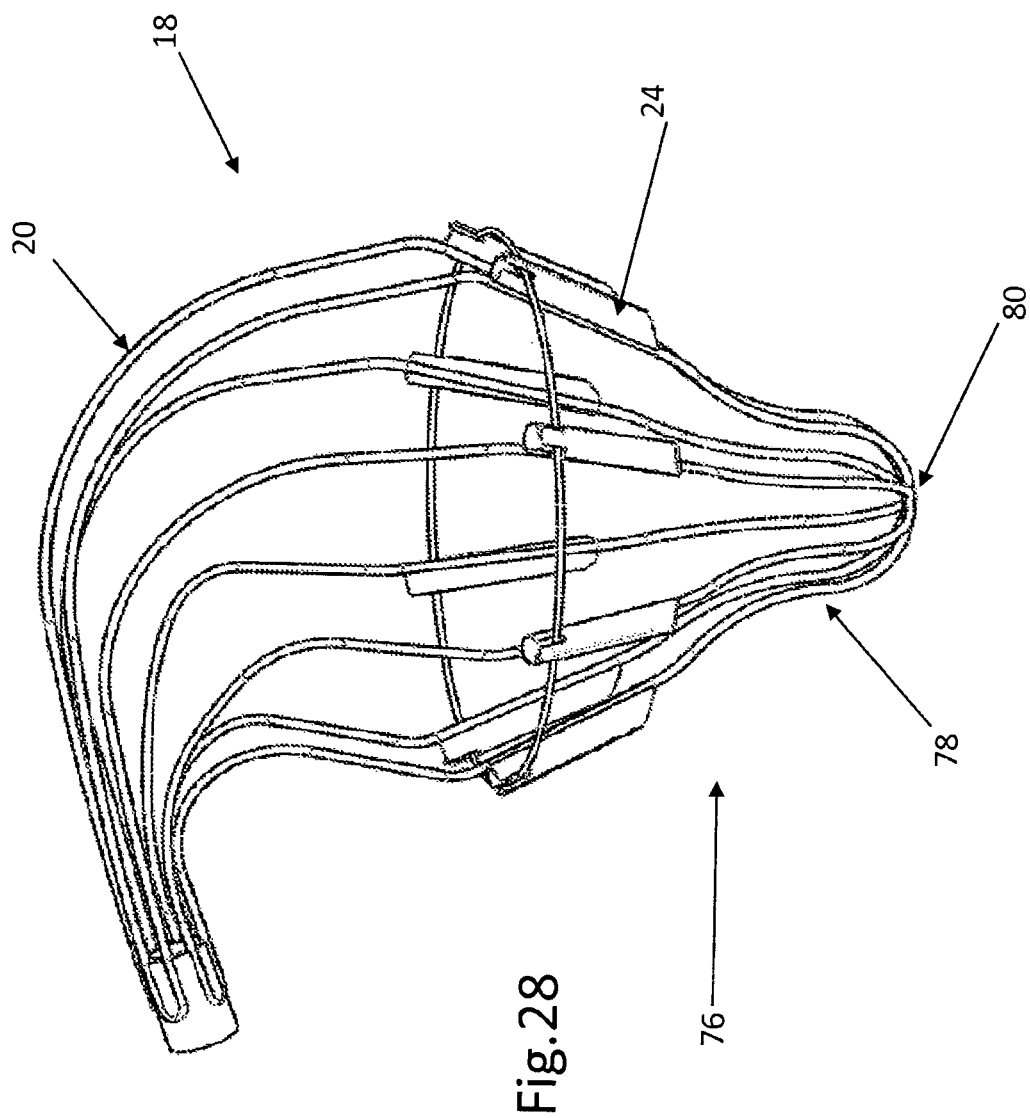
Figure 29:
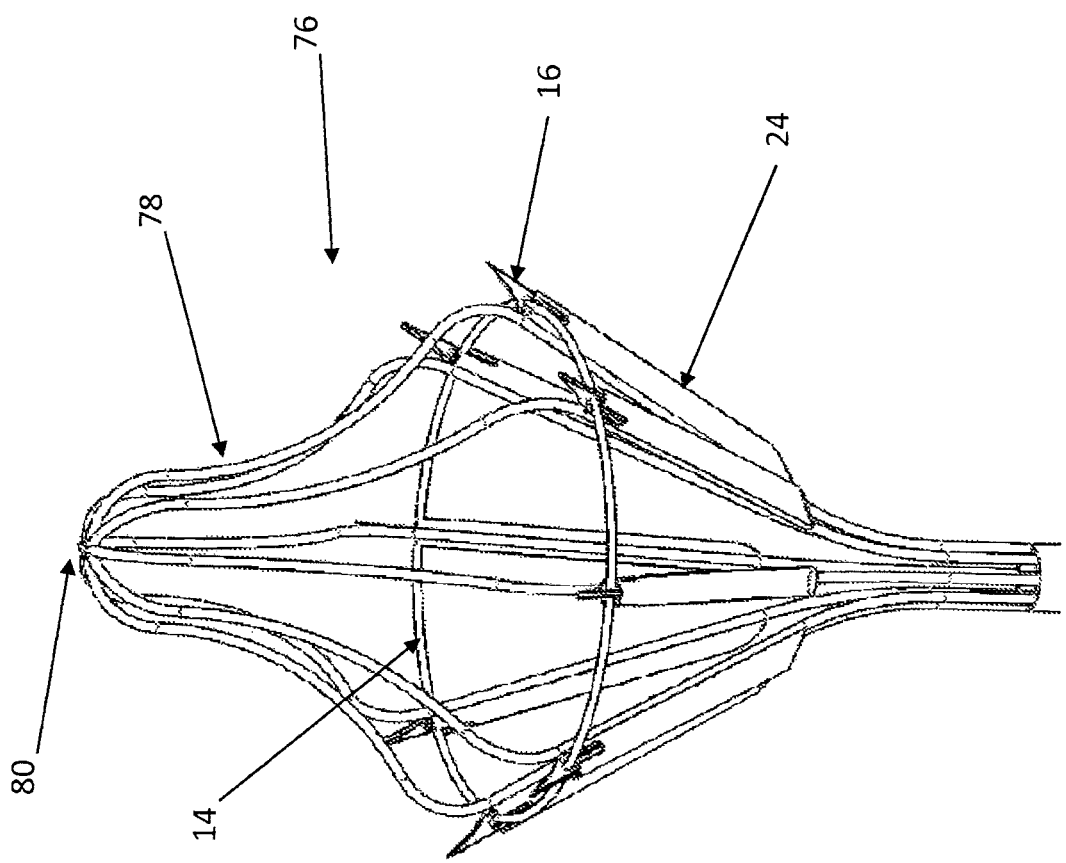
Figure 30:
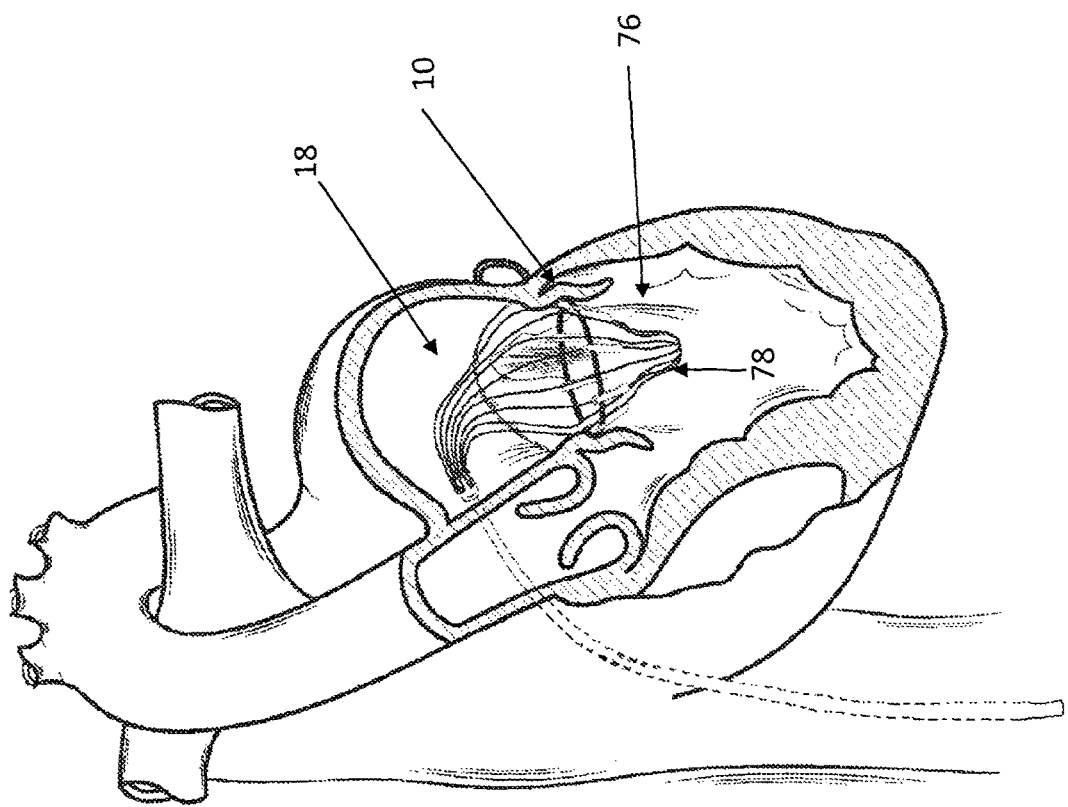

FIGS. 28-30 show embodiments, wherein implant 10 further comprises a loop-arrangement/anchor-orientation mechanism 76 useful for arranging the position and/or shape of loop 14 and/or for orienting the angle of housings 24, and thereby orienting the launch angle of tissue anchors 16. Anchor orientation mechanism 76 includes a plurality of curved arrangement leads 78 respectively attached to at least some of housings 24, for example by welding. Leads 78 may be an extension of implant support arms 20 and may be arranged to cross at a singular intersection point 80. Leads 78 are attached (e.g. by welding) to housing 24. Thus, leads 78 of orientate mechanism 76 are movable to arrange loop 14 in a desired location and depending on the shape of the leads, the angle of housings 24, and thus anchors 16, can be determined.

Regarding the launch angle of anchors 16, in some embodiments, leads 78 can be attached "ad hoc" prior to insertion into a patient, whereby, depending on the attachment location, arrangement leads 78 also be used to orient anchors 16 i.e. control the angle at which the anchors enter the tissue (i.e. changing the length or shape of one or more leads 78 will thus change the angle of the anchors, e.g. shortening the that length will cause the anchors to point outward, whereas increasing that length will bring intersection point 80 farther from loop 14 and thus angle the anchors more parallel to each other (less outward). In such case, leads 78 will not be welded to housings 24, rather there will be included an "ad hoc" connection or fastening arrangement (not shown), whereby the leads and housings are connected at more than one location along the leads. Arrangement/orientation mechanism 76 can be useful for arranging the shape of loop 14 as well as positioning the loop and orienting the anchor angle. In alternative embodiments, loop-arrangement/anchor-orientation mechanism 76 either has a predetermined shape, such as a nipple shape (FIGS. 29 and 30) or is adapted to allow its shape to be changed; i.e. leads 78 can be bent.

Figure 31:
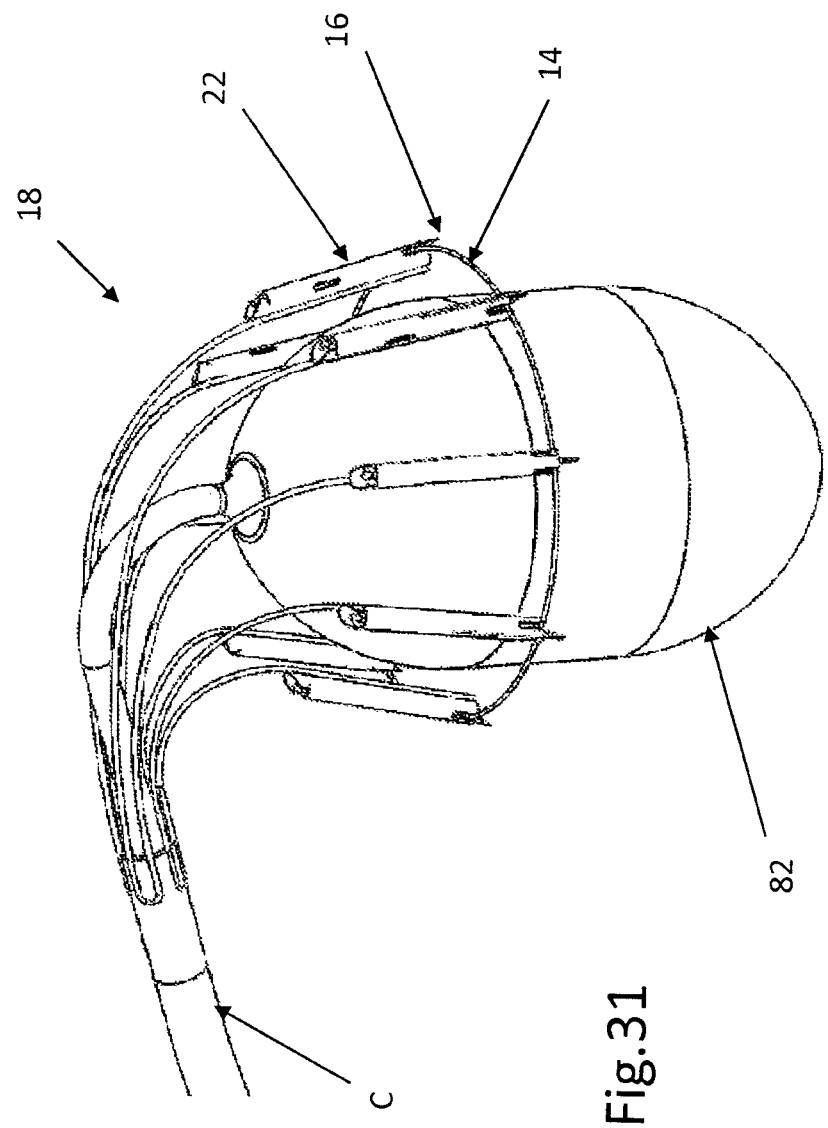

FIGS. 31-34 show embodiments wherein loop arrangement and/or implant positioning device 18 comprises an inflatable balloon 82. The figures show exemplary balloons 82 useful for a) making sure support arms 20 are fully expanded before deploying implant 10, b) make sure that loop 14 is concentric with the valve annulus prior to implantation, and c) facilitating an interference step or backing against which to press to be used for pressing implant positioning device 18 and implant 10 onto the valve annulus before implantation as illustrated in FIG. 34. FIG. 31 illustrates an oval balloon 82; FIGS. 32-34 illustrate a droplet-shaped or bulbous balloon 82.

As seen in FIG. 34, as well as being useful to orient loop 14 relative to the valve annulus, the balloon can be used to secure the implant positioning device 18 and implant 10 in place during launching of anchors 16. FIGS. 32 and 33 also illustrate that balloon 82 can be positioned proximally or distally with respect to loop 14 and implant positioning device 18. Since the balloon can be positioned inside the ventricle and be inflated to a diameter bigger than the diameter. of biological valve annulus, it can serve as a backing against which to press positioning device 18 and implant 10 onto the valve annulus before implantation. This will ensure good contact between each of the anchor launching mechanisms 22 and the valve annulus and will create optimal penetration conditions of anchor 16 into the tissue upon launching. Furthermore, the launch angle of anchors 16 (i.e. insertion into the tissue) can be controlled by inflating/deflating balloon 82, with consideration to the size of the biological valve.

Figure 35:
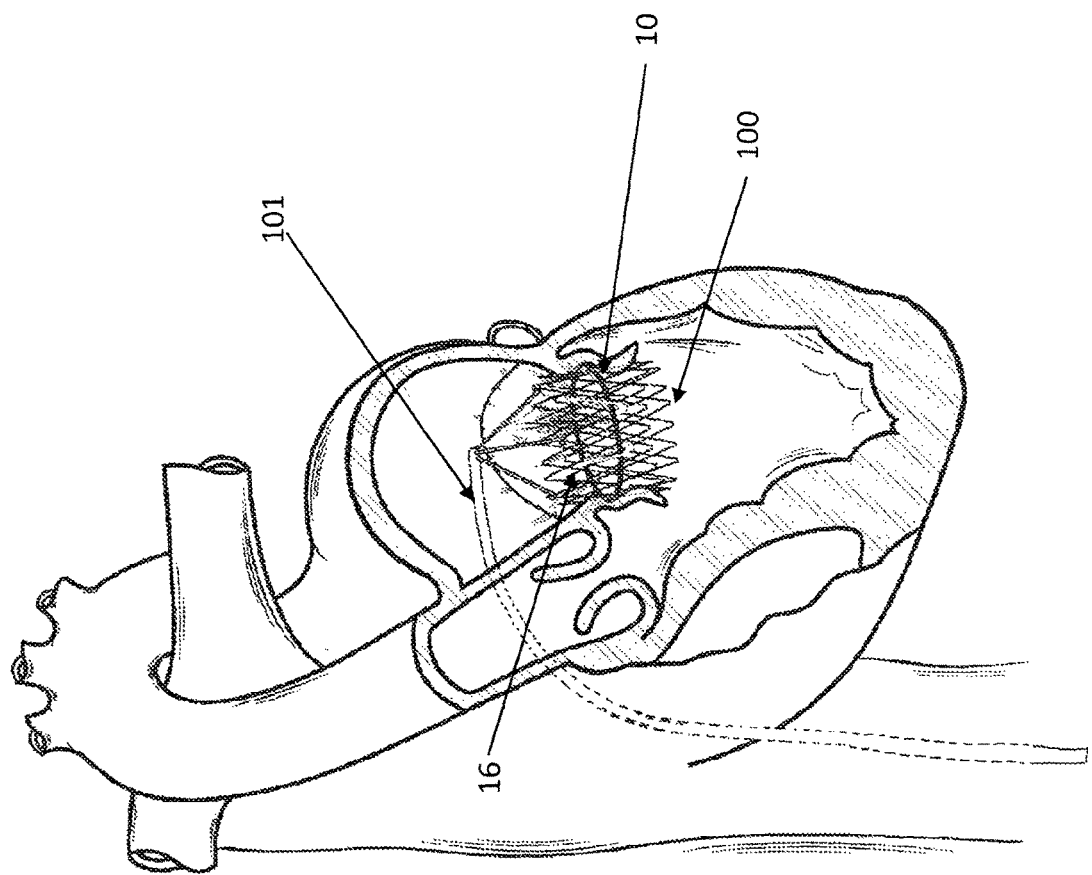
Figure 36:
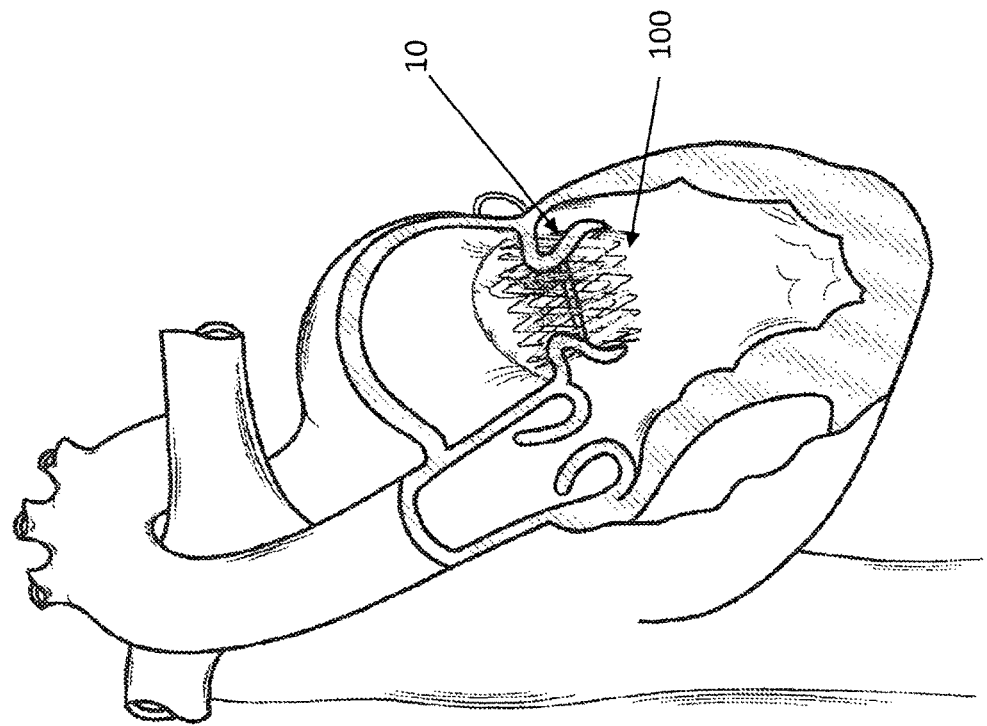
Figure 37:
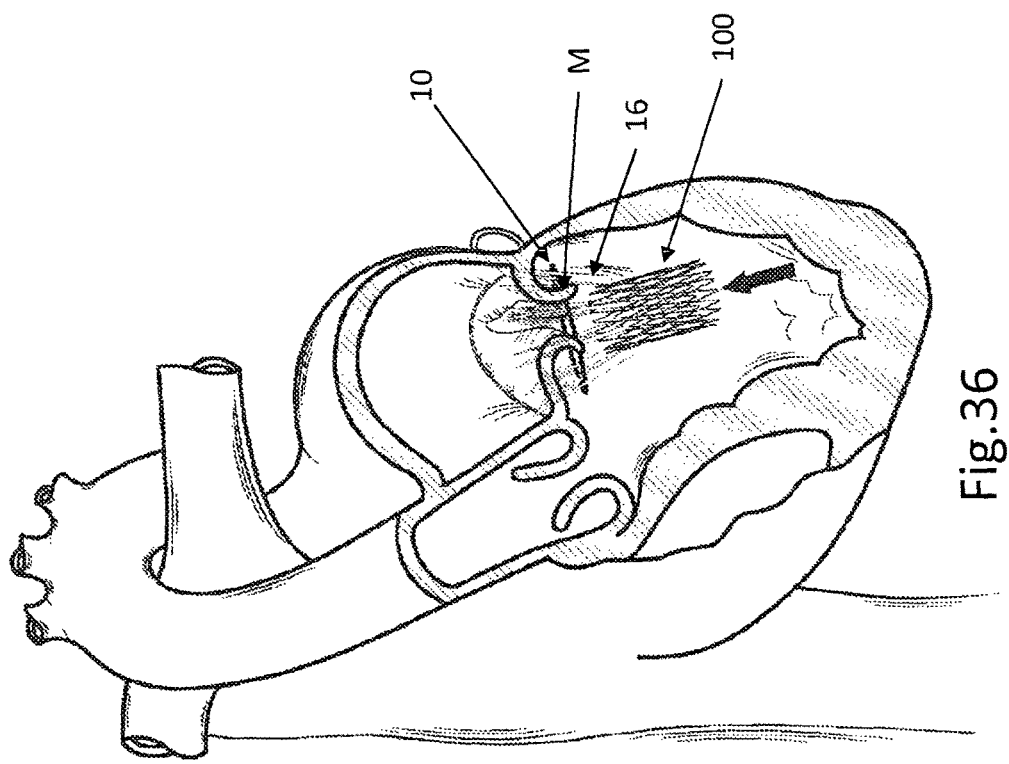

FIGS. 35-37 illustrate how a device 100 (e.g., a replacement valve) can be fixed to a native valve annulus or leaflets like the mitral valve M or tricuspid valve. In this embodiment, implant 10 is first implanted and secured with anchors 16 that penetrate the valve leaflets pointing from the ventricle V side toward the atrium A side (hereinafter upwards) as in FIG. 21 and/or FIG. 22. Then, when device 100 is expanded into implant 10, the friction between anchors 16 and the device 100 secures device 100 in place. Since anchors 16 are directed generally upward, the high pressure in ventricle V helps to further enhance the anchoring of implant 10 to the valve leaflets.

Device 100 in the illustrating figures represents any suitable commercial expandable heart valve prosthesis that can be tracked in a collapsed configuration through the vascular system and delivered to the heart. It can be a self-expanding prosthesis or a balloon expanding prosthesis or any other type of expanding heart valve prosthesis. FIG. 35 further illustrates an exemplary delivery system 101 that can deliver device 100 to the heart.

FIGS. 36 and 37 illustrate how implant 10 can be associated with device 100 for fixing the device to a mitral valve M (or tricuspid valve) leaflets. In this embodiment, implant 10 and device 100 are implanted via the heart's apex P, preferably, in a minimally invasive surgery as illustrated in FIG. 20. As in FIG. 22, implant 10 is first located at the proper location with respect to the bio-valve (mitral in this case) and then secured with anchors 16 facing upward, in accordance with any appropriate embodiment as described herein. After implant 10 is attached to the valve leaflets, device 100 is advanced, as shown in FIG. 36. Through a delivery catheter (not shown), and expanded into implant 10 as seen in FIG. 37. Since anchors 16 are directed generally upward, the high pressure in the ventricle V helps to further enhance the anchoring of the implant 10 and device 100 to the valve leaflets. However, for the purpose of this embodiment, wherein implant 10 is configured to be particularly suited to securing a device in place such as device 100, each anchor 16 has a relatively shorter slot 17, typically extending only about half-way along the longitudinal dimension of each anchor, from about half-way along the anchor to relatively close to the anchors' pointy front end 46, as seen in FIG. 7A.

With reference to FIGS. 38 and 39, when device 100 is disposed in the appropriate heart (or other biological) valve and expanded, the contact and sliding motion between the device and anchor 16 changes the angle of the anchors from typically approximately 45 degrees (FIG. 38), although, depending on the angle of support arms 20, to an angle wherein the anchors are more parallel to each other, typically substantially parallel. The movement of anchors 16 is illustrated by arc A-B in FIG. 38. In other words, anchors 16 pivots at the end of slot 17, as in FIG. 7A which is generally at mid-point 84 of the anchors. This angle change provides increased friction between anchors 16 and device 100 thereby securing the device in place.

To further explain, device 100 is expanded in the bio-valve until the device presses on a non-slotted portion 86 of anchors 16. As a result of pressing on non-slotted portion 86, that portion is forced outward, and thus the tip of the anchors 46 is moved inward, as the anchors pivot around loop 14. Since anchor tips 46 are locked within the tissue of the valve leaflet, the inward motion of the tips pulls the leaflets closer to device 100 and presses the leaflets against the device, thereby enhancing the sealing and prevent blood flow between the native valve leaflet and the device. It should be understood that device 100 is appropriately sized for the above-described positioning.

Figure 40:
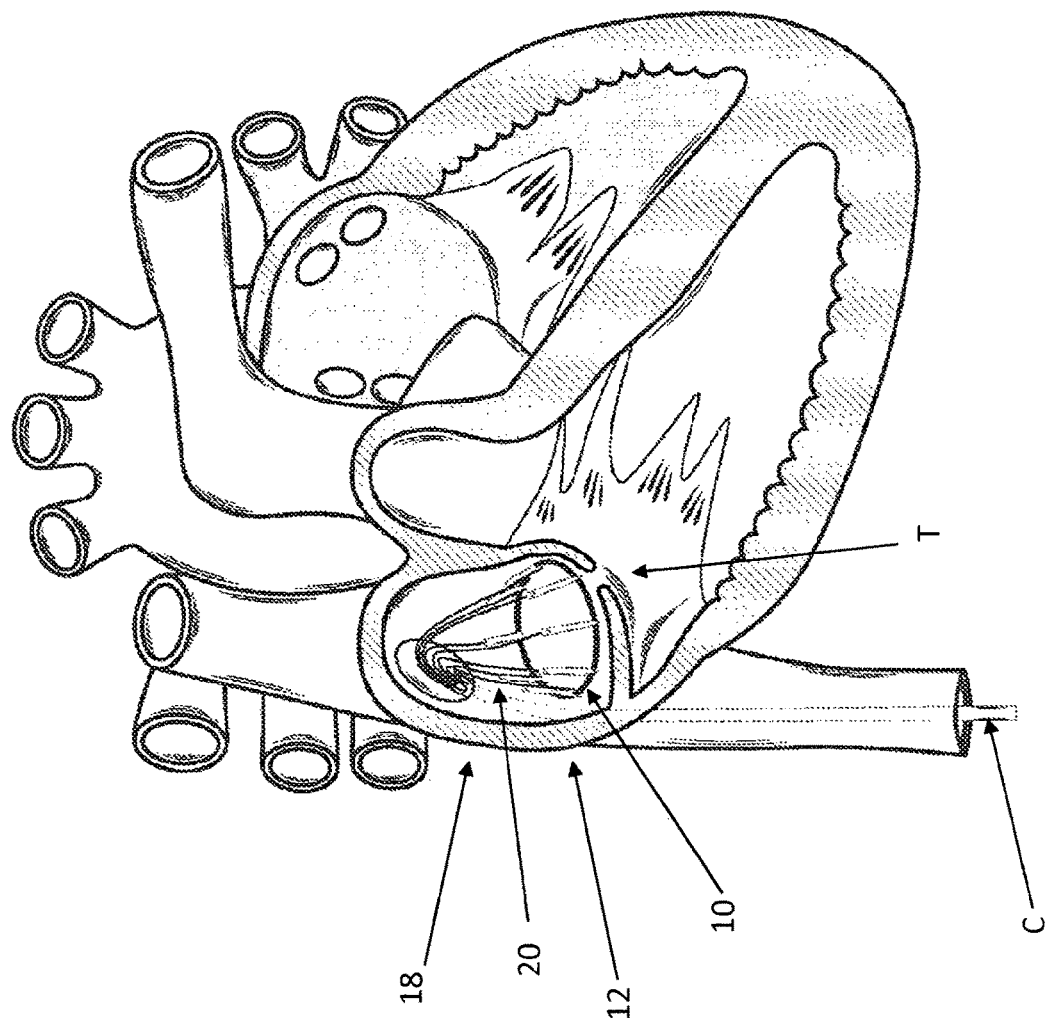
FIG. 40 is a perspective partially cut-away view of the heart with the implant deployed for use on a tricuspid valve.

FIG. 40 illustrates deployment of implant 10 in the tricuspid heart valve T and it should be understood that all the features and functions of the implant and delivery system as illustrated in FIGS. 1 to 39 are applicable to the tricuspid valve.

Figure 41:
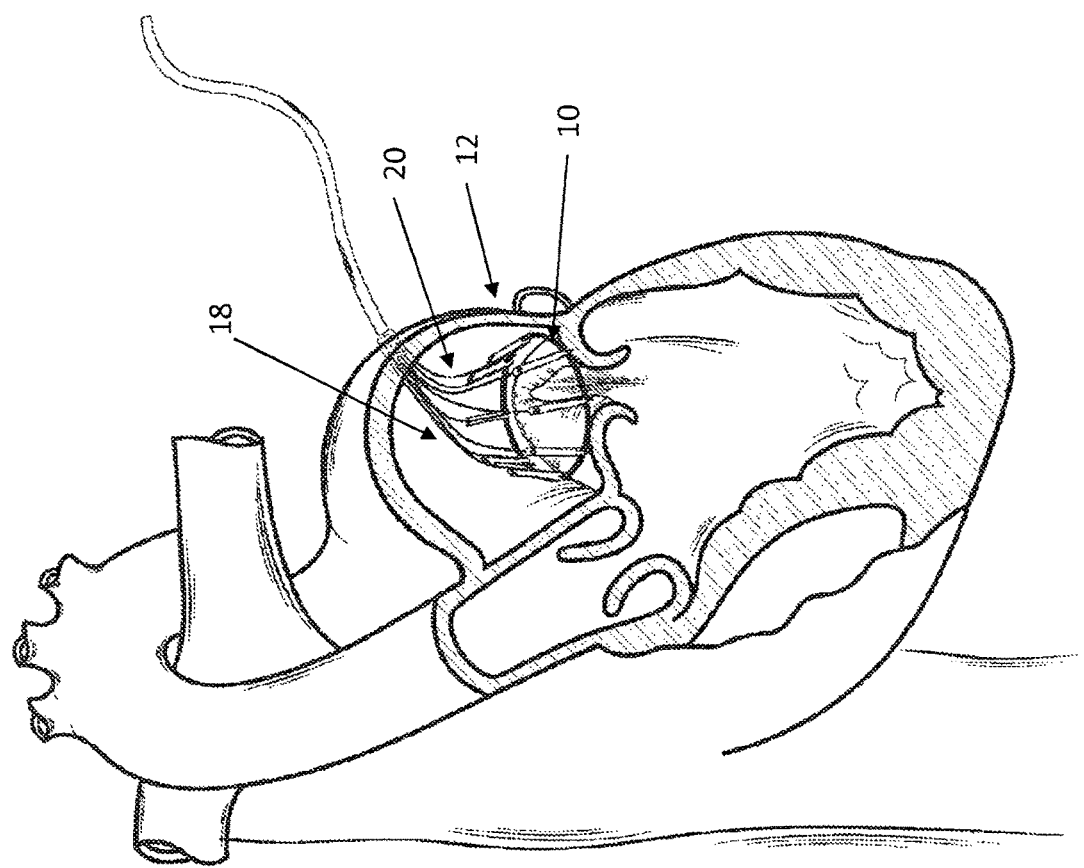
FIG. 41 is a perspective partially cut-away view of the heart with the implant deployed via the left atrium wall.

FIG. 41 illustrates deployment of implant 10 through the left atrium wall rather than tracking in through the vascular system, or deploying the implant through the apex of the heart. Again, it should be understood that all the features and functions of the implant and delivery system illustrated in FIGS. 1 to 39 are applicable to deployment through the atrium wall.

Figure 42:
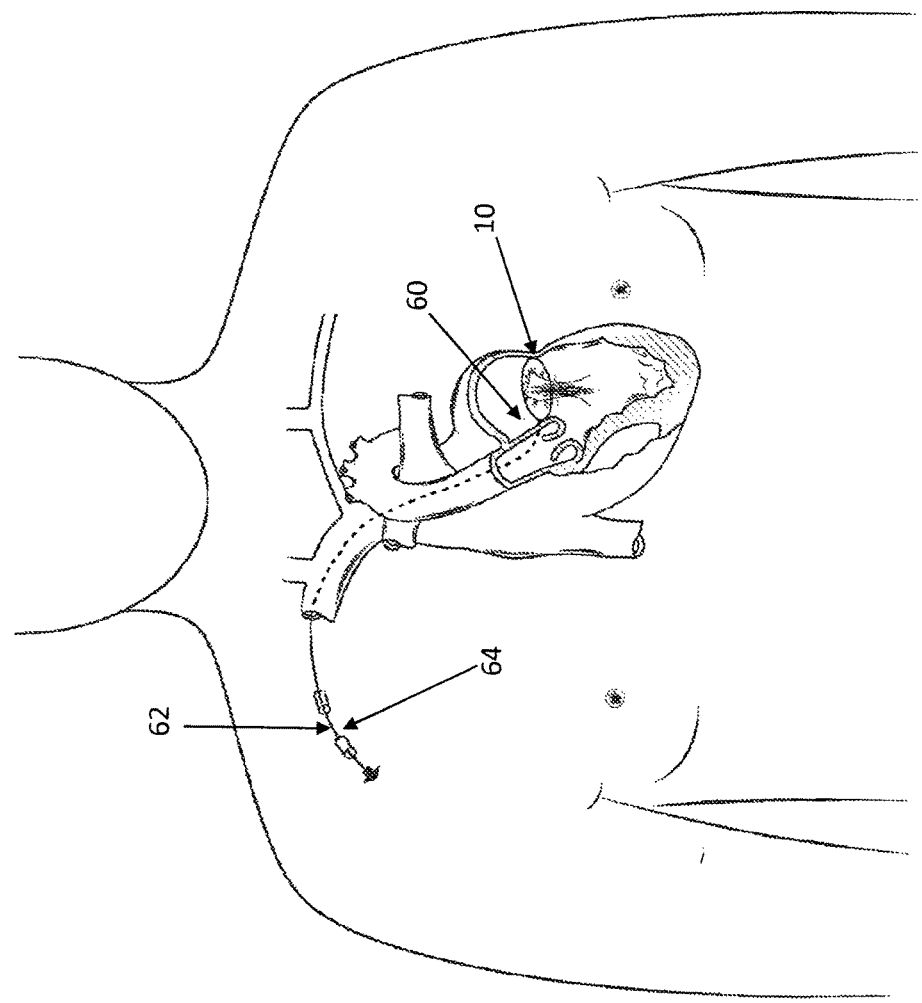
FIG. 42 is a view illustrating manual cinching of the device after tissue healing.

FIG. 42 illustrates manual cinching of the device in a later procedure after tissue healing has occurred as described above with reference to FIG. 14.

Figure 43:
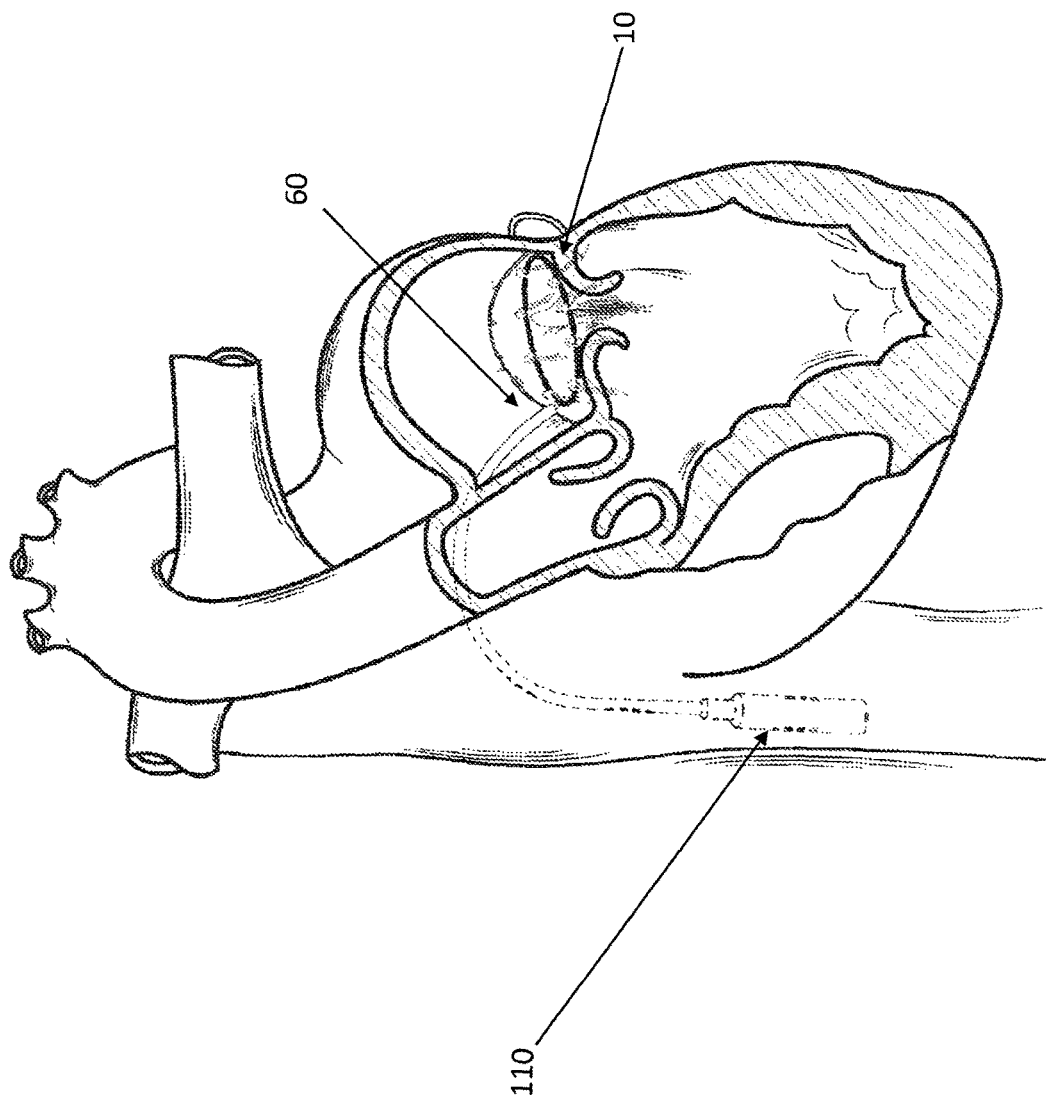
FIG. 43 is a perspective partially cut-away view of the heart illustrating mechanical cinching of the device after tissue healing.
Figure 44:
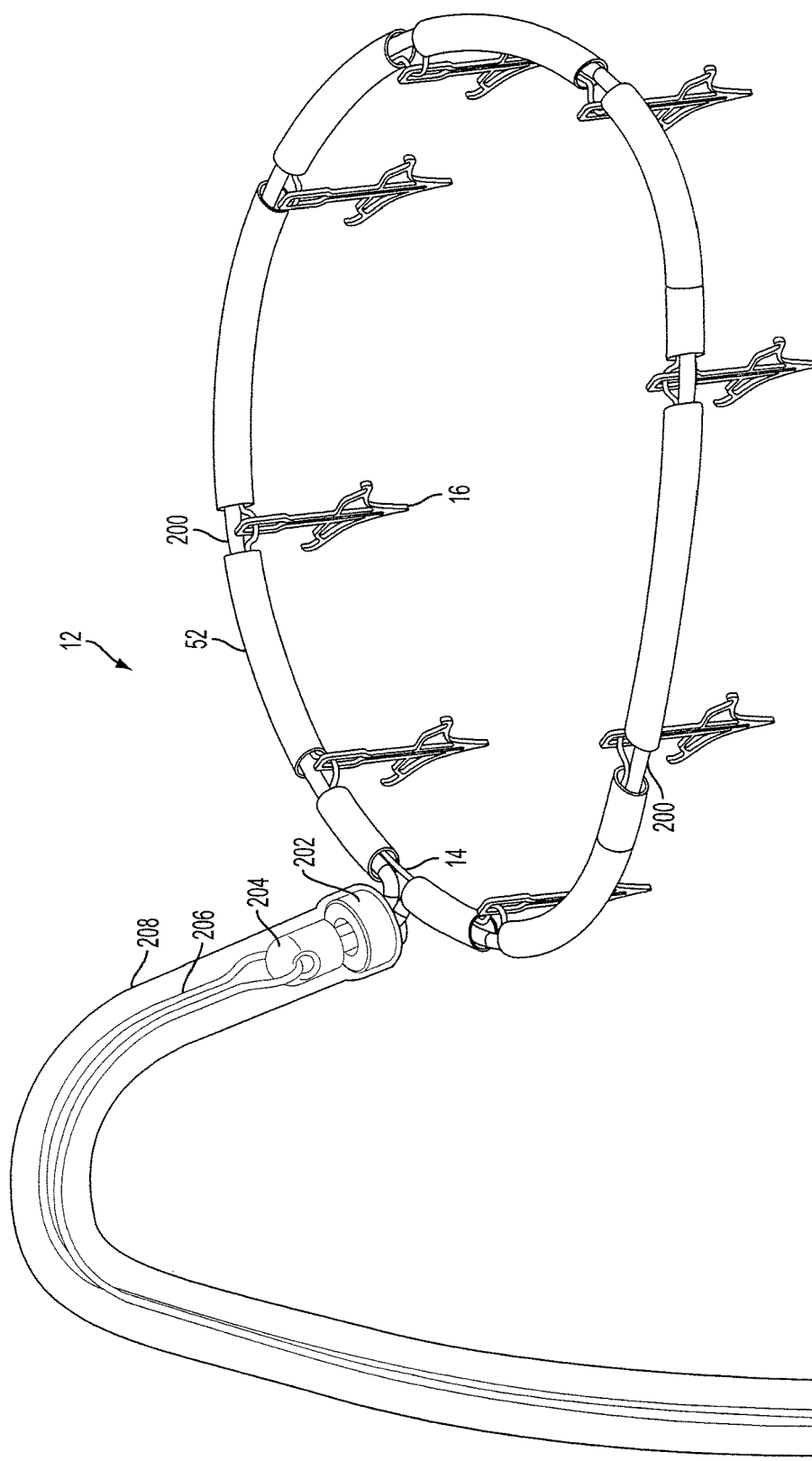

FIG. 43 illustrates cinching of the device in a later procedure after tissue healing has occurred as described above with reference to FIG. 14. Using a mechanical actuator 110 that is implanted during procedure. The mechanical actuator can be actuated and operated magnetically, electrically or by any other appropriate mechanism from outside of the body.

FIGS. 44-47 depict one exemplary embodiment for implementing cinching. In this embodiment, the implant has a tissue engaging member 12 that includes a loop of wire 14 and a plurality of tissue growth-promotion tubes 52 coaxially arranged about the loop of wire. The tissue growth-promotion tubes 52 are made of a material that promotes ingrowth of tissue, such as a fabric segments, optionally coated with a tissue growth promoting substance. Taken together, the loop of wire 14 and the plurality of tissue growth-promotion tubes 52 collectively form a loop of material.

The tissue engaging member 12 also includes a plurality of tissue anchors 16 that are arranged with respect to the loop of wire. In the illustrated embodiment, the anchors 16 are spaced apart all along the loop of wire 14 and the loop of wire is threaded through slots in the anchors 16. Preferably at least six anchors are used. Note that although the anchors depicted in FIGS. 44-47 most closely resemble the configuration of anchors shown in FIG. 52B, any alternative anchor style many be used in place of that configuration for the anchor. In alternative embodiments, the anchors may be attached to the wire using linking members like those shown in FIGS. 56A and 56B. The anchors 16 may be launched using any of the approaches described herein.

This embodiment also includes a cinching cable 200, which is preferably covered with a slippery coating such as PTFE or the like. Cinching cable 200 has two ends that are threaded through a cinching collar 202 and are attached to a cinching member 204 that has a cinching aperture or eyelet. A cinching lead 206 is threaded through cinching aperture and the lead's free ends may extend outside the patient's body or remain under the skin at the upper portion of the chest, much like pace maker leads. After sufficient tissue grows on the implant, which typically takes one week to several months, depending on the tissue growth rate, the implant may be cinched by pulling on one or both of the free ends of cinching lead 206 to thereby pull on cinching cable 200 and reduce the diameter of tissue engaging member 12.

Figure 45:
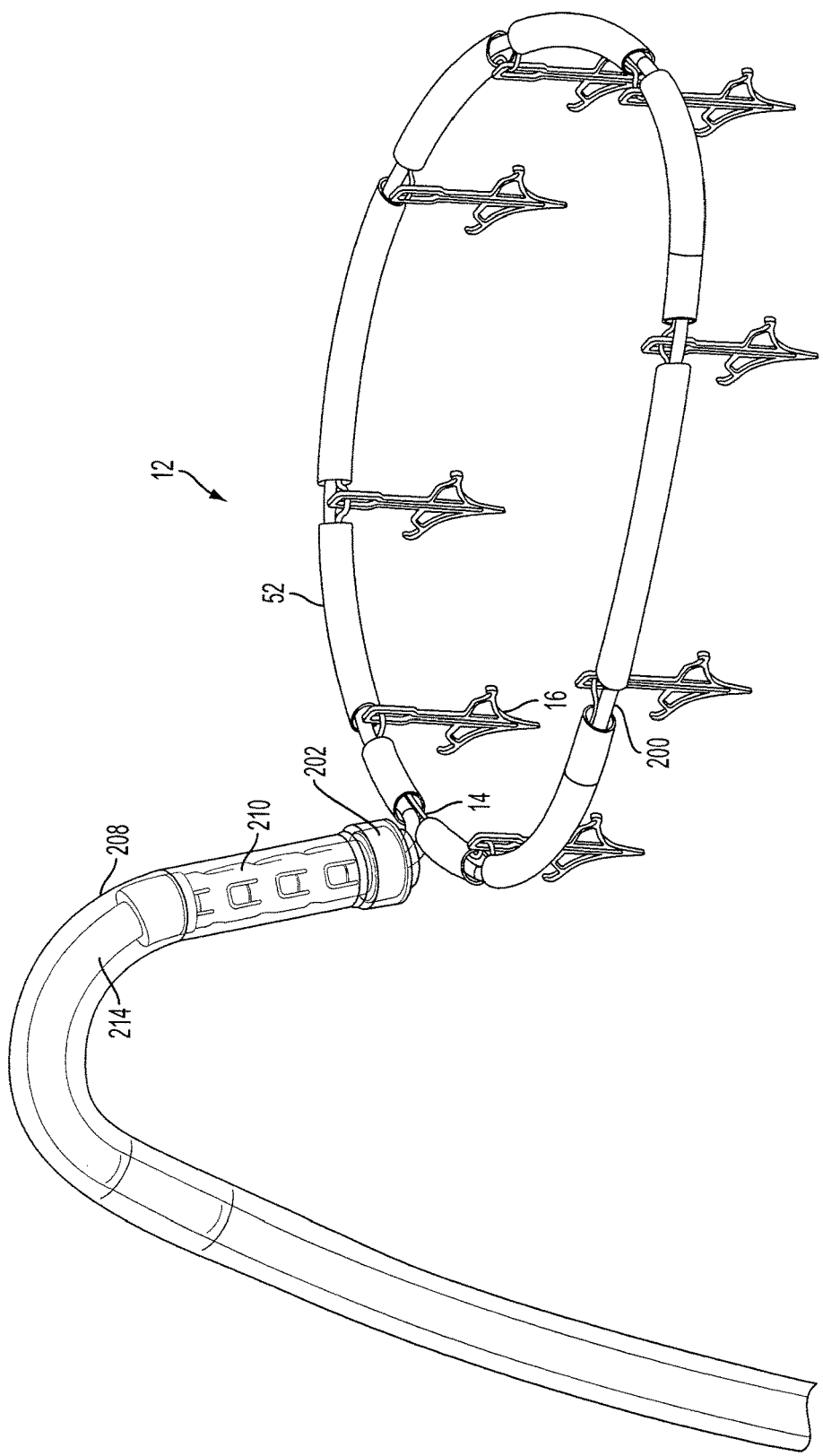

To effect cinching, a cinching sleeve 208 is pushed along over the cinching lead 206 until the distal end of the cinching sleeve 208 bottoms out at the cinching collar 202. Then, a cinching tube 210 is pushed through cinching sleeve 208 by a pushing member 214 until the cinching tube 210 reaches cinching collar 202, as seen in FIG. 45. After this, by pulling on both ends of the cinching lead 206, cinching eyelet member 204 is retracted into cinching tube 210, as seen in FIG. 46. In the illustrated embodiment, cinching tube 210 has a plurality of one way flaps or steps 216 spaced apart along the length of the tube for holding cinching member 204 in place as the cinching member 204 retracts in the cinching tube 210, thereby controlling the ultimate length/diameter of cinching cable 200 so as to constrict the annulus of the bio-valve. Alternative approaches for implementing one-way motion of the cinching member 204 will be apparent to persons skilled in the relevant arts.

After the cinching cable 200 has been cinched to the appropriate length/diameter, one end of cinching lead 206 may be pulled to remove the cinching lead, the pushing member 214 may be removed, and the cinching sleeve 208 may also be removed. The resultant implant would then appear as is seen in FIG. 47. In alternative embodiments, some or all of these components 206, 208, 214 may remain behind as part of the implant e.g., for implementing additional cinching at a later point in time.

Figures 48A, 48B:
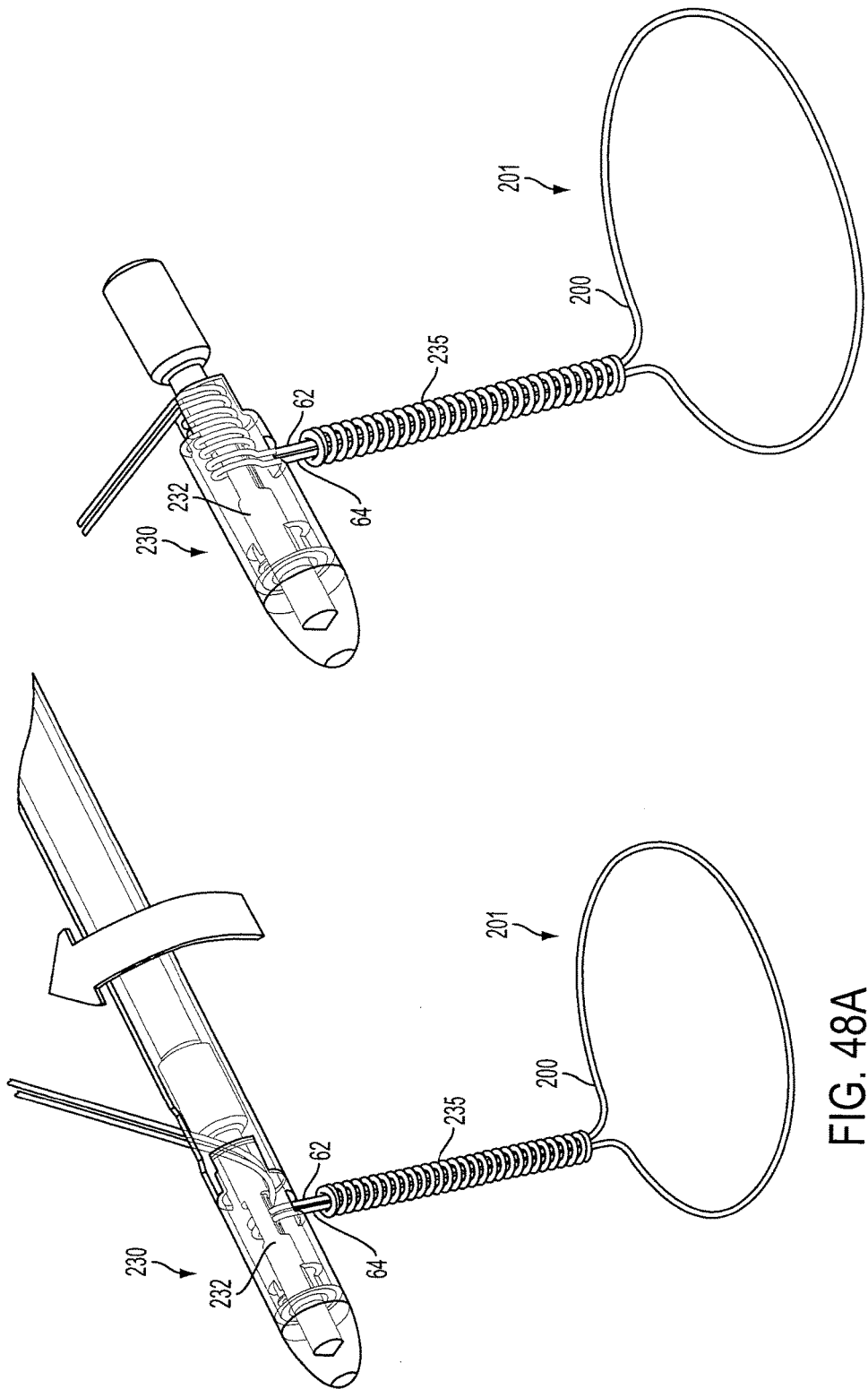
FIGS. 48A and 48B depict an alternative spindle-based embodiment for implementing cinching.

FIGS. 48A and 48B depict an alternative cinching mechanism in which the ends of the cinching cable 200 are pulled by rotating a spindle 232 in a mechanism 230 that is preferably implanted in the patient's body. In some embodiments, the rotation may be implemented by a motor that is powered by a battery (not show) and controlled remotely from outside the patient's body. In the illustrated embodiment, the loop 201 is biased against a spring element 235. When the spring element 235 is initially implanted, it will be flexible. But after implantation, tissue ingrowth will cause the spring to become rigid and capable of sustaining a compression load. Rotation of the spindle is preferably delayed until after such tissue ingrowth has occurred. The rotating mechanism preferably includes a ratchet that permits rotation in only one direction. Rotation of the spindle 232 will wind up the ends of the cinching cable 200 from the state depicted in FIG. 48A to the state depicted in FIG. 48B, which pulls the main loop 201 of the cinching cable 200 against the bottom of the spring element 235, thereby tightening the main loop 201.

FIGS. 49-52 illustrate a variety of alternative anchors that may be used in place of the anchors 16 shown in FIG. 7.

Figure 49A:
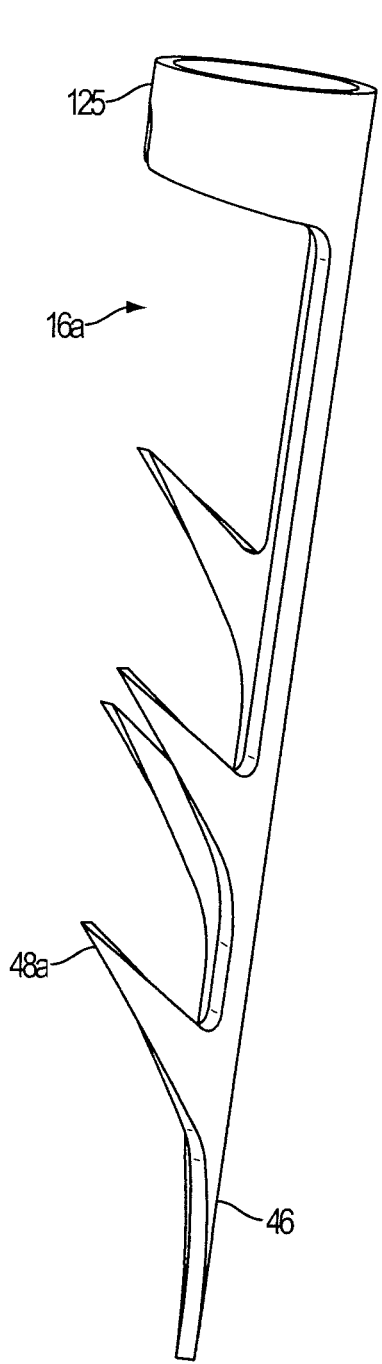
FIGS. 49A and 49B depict an embodiment of a cylindrically shaped anchor.
Figure 49B:
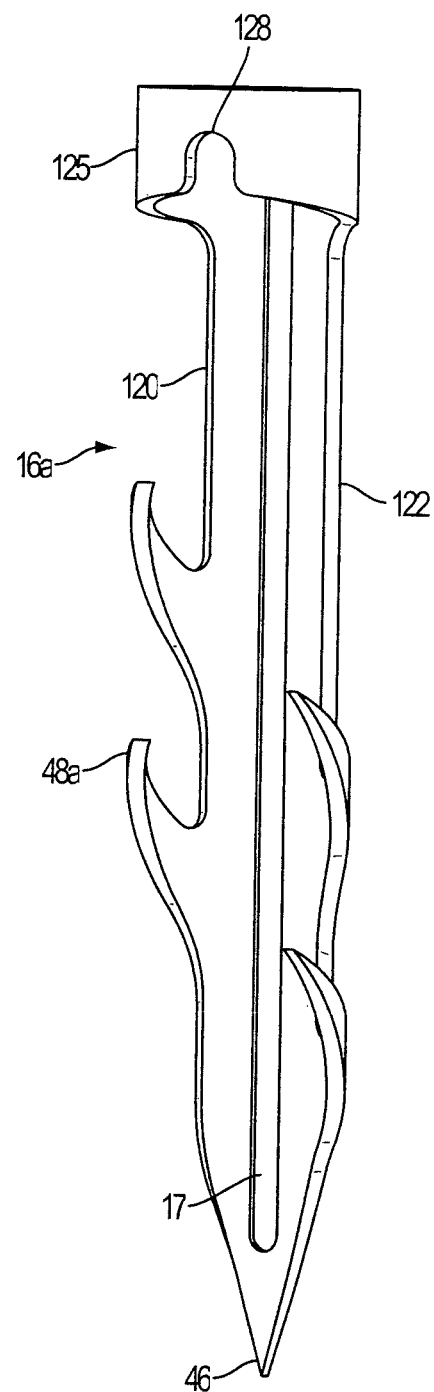

FIGS. 49A and 49B depict one such anchor 16a that is partially tubular or cylindrical in shape. This anchor has a first panel of material 120 that has a cylindrically curved outer surface and a second panel of material 122 that also has a cylindrically curved outer surface. A slot 17 runs in a front-to-back direction disposed between the first panel of material and the second panel of material. The pointy front end 46 of the anchor is configured for implantation into the annulus or the leaflets in a forward direction. There are also a plurality of barbs 48a that are configured so that subsequent to implantation, the barbs resist extraction of the anchor from the annulus or the leaflets in a backwards direction. Preferably, this anchor 16a also has a ring-shaped portion 125 disposed at a back end of the anchor that connects the first panel of material 120 to the second panel of material 122.

Preferably, a front surface of the ring-shaped portion has a notch 128, and the slot 17 and the notch 128 are disposed on opposite sides of the ring-shaped portion 125. In some embodiments, the outer surface of the barbs 48a is curved so as to follow the cylindrical curve of the outer surface of the panel of material to which it is attached (i.e., panels 120 and 122). This type of anchor 16a can be advantageously produced by cutting it out from a tube of material. Preferred materials for this anchor 16a include metals (e.g., steel alloys, stainless steel, nitinol), biocompatible plastics, and ceramics. The overall length of the anchor 16a is preferably between 3 and 30 mm, and more preferably between 5-10 mm. The diameter of the ring 125 is preferably between 0.5 and 5 mm, and more preferably between 1 and 2 mm.

Figure 50A:
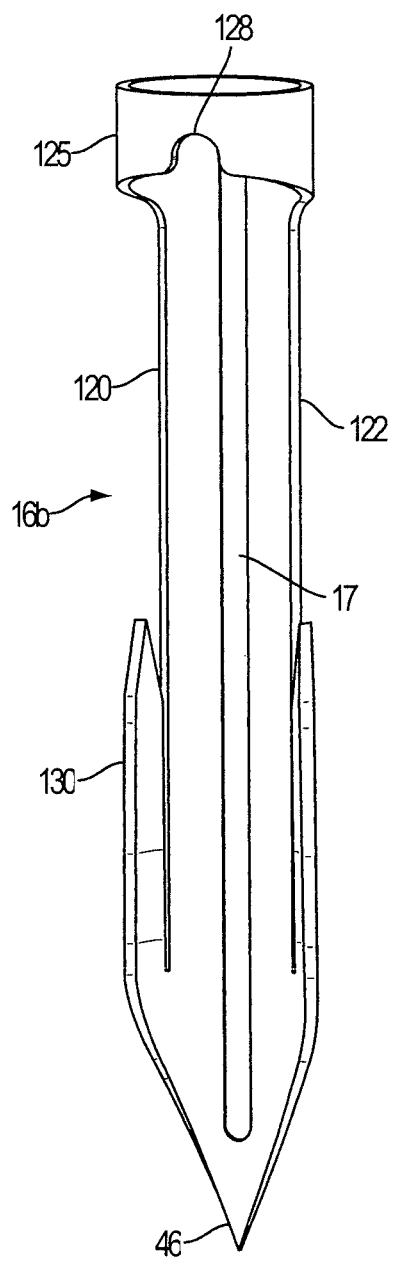
FIGS. 50A and 50B depict another embodiment of a cylindrically shaped anchor.
Figure 50B:
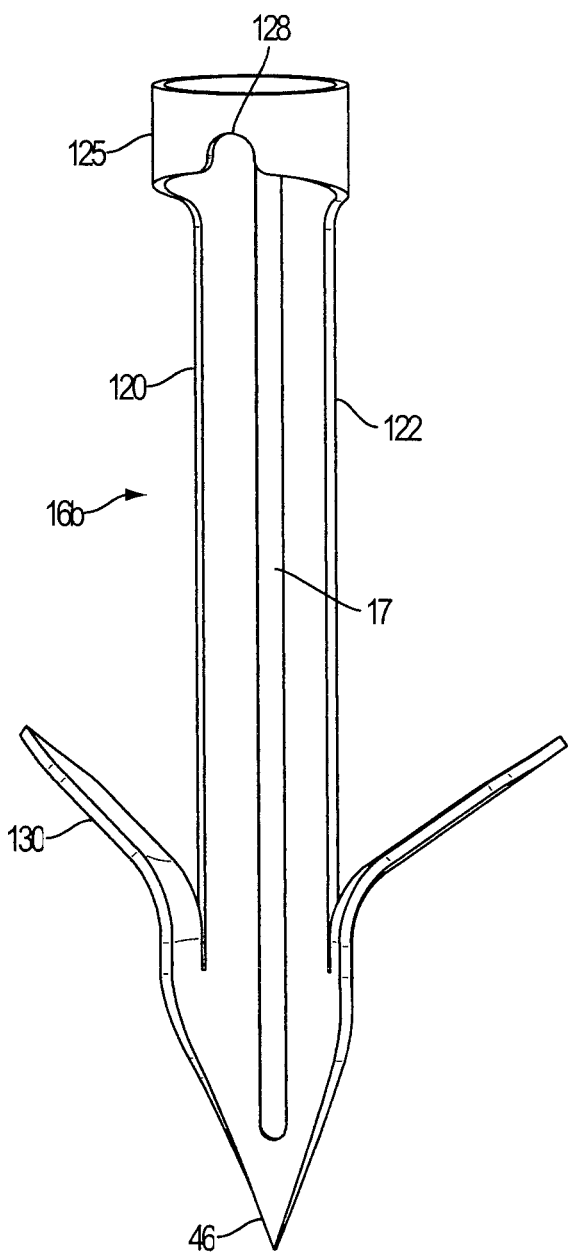

FIGS. 50A and 50B depict another anchor 16b that is partially tubular or cylindrical in shape. This anchor 16b also has a first panel of material 120 that has a cylindrically curved outer surface and a second panel of material 122 that also has a cylindrically curved outer surface. A slot 17 runs in a front-to-back direction disposed between the first panel of material and the second panel of material. The pointy front end 46 of the anchor is configured for implantation into the annulus or the leaflets in a forward direction. This anchor 16b has at least one tab 130 that is configured to automatically spring outward after being implanted, so that after the tab has sprung outward (as seen in FIG. 50B), the tab causes the anchor to resist extraction from the annulus or the leaflets in a backwards direction. Note that prior to implantation, the tabs 130 remain in the collapsed state depicted in FIG. 50A and do not spring outward because they are restrained from doing so by a housing (such as the housing 24 shown in FIGS. 4, 5, and 54A).

As in the FIG. 49 embodiment, this anchor 16b also preferably has a ring-shaped portion 125 disposed at a back end of the anchor that connects the first panel of material 120 to the second panel of material 122. Preferably, a front surface of the ring-shaped portion has a notch 128, and wherein the slot 17 and the notch 128 are disposed on opposite sides of the ring-shaped portion 125. This type of anchor 16b can also be advantageously produced by cutting it out from a tube of material. The spring-out tabs 130 may be implemented using spring material or using a shape memory alloy. The preferred materials and dimensions for this embodiment are similar to those for the embodiment described above in connection with FIGS. 49A and 49B.

Figure 51A:
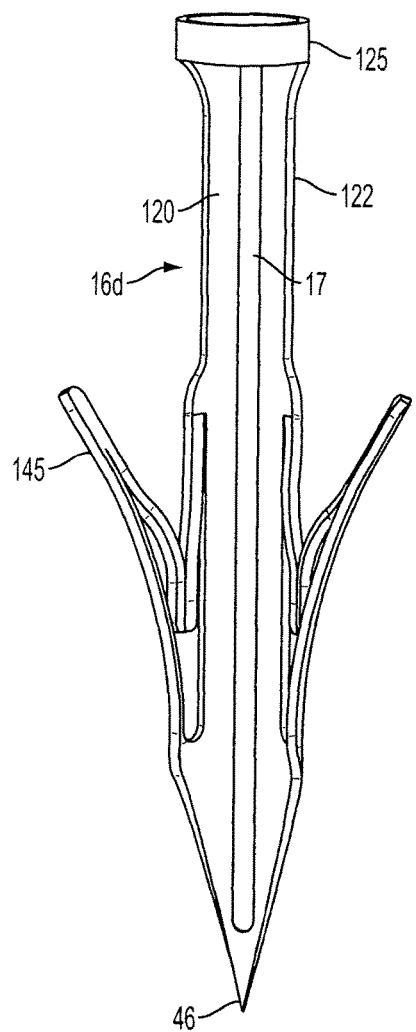
FIGS. 51A and 51B depict another embodiment of a cylindrically shaped anchor.
Figure 51B:
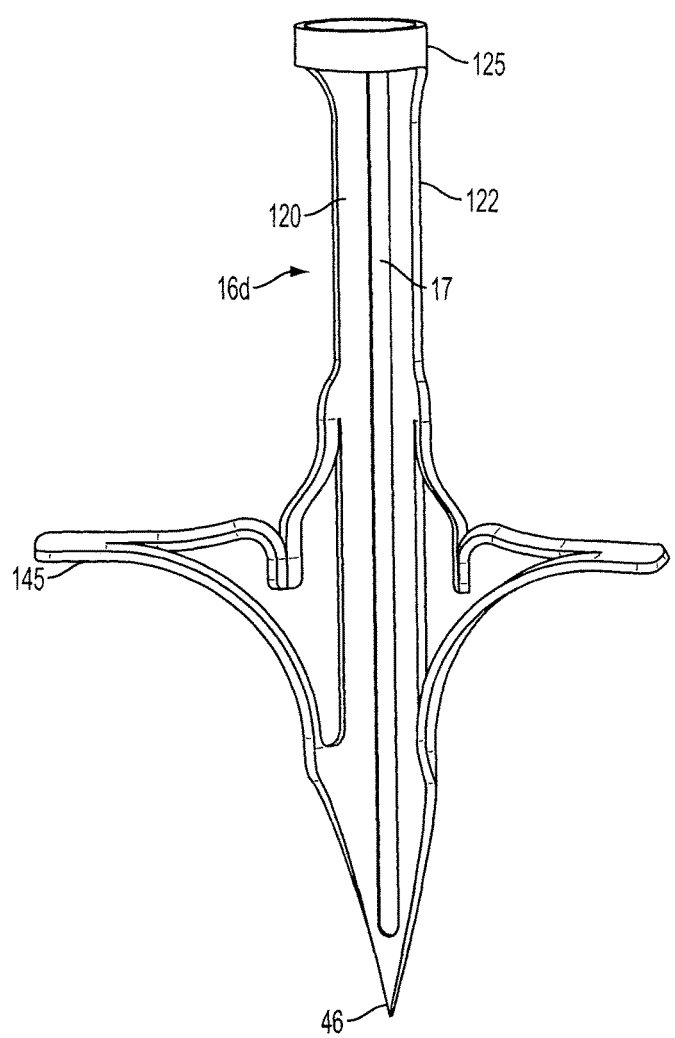
Figure 54A:
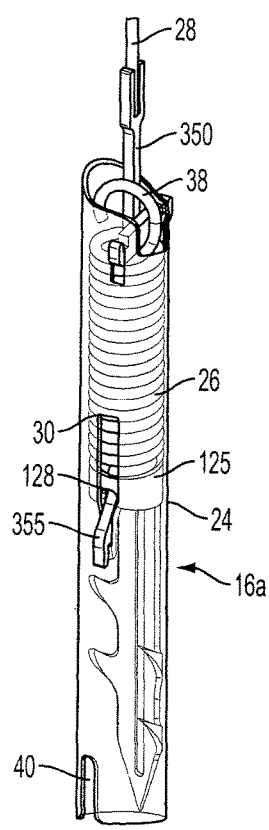
FIGS. 54A, 54B, and 54C depict an embodiment of an anchor launching mechanism.

FIGS. 51A and 51B depict another anchor 16c that is partially tubular or cylindrical in shape. This anchor 16c is similar to the anchor 16b depicted in FIGS. 50A and 50B, but instead of the tabs that are configured to automatically spring outward after being implanted, this anchor 16c uses one or more arms 145 formed from a shape-memory alloy (SMA) material. These arms are configured to automatically spring outward after being implanted by operation of the SMA material, so that after the arm has sprung outward (as seen in FIG. 51B), the arm causes the anchor to resist extraction from the annulus or the leaflets in a backwards direction. Note that prior to implantation, the arms 145 remain in the collapsed state depicted in FIG. 51A and do not spring outward because they are restrained from doing so by a housing (such as the housing 24 shown in. FIGS. 4, 5, and 54A). This type of anchor 16c can also be advantageously produced by cutting it out from a tube of material. The preferred materials and dimensions for this embodiment are also similar to those for the embodiment described above in connection with FIGS. 49A and 49B.

Figure 52A:
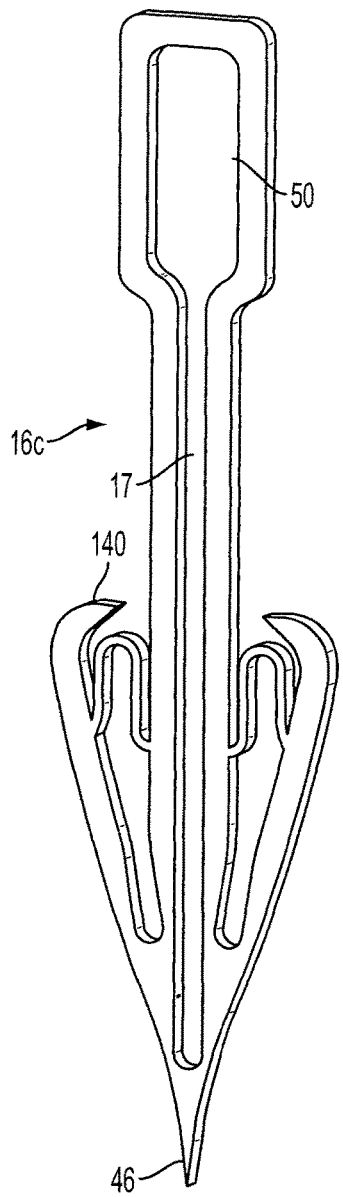
FIGS. 52A and 52B depict an embodiment of an expandable anchor.
Figure 52B:
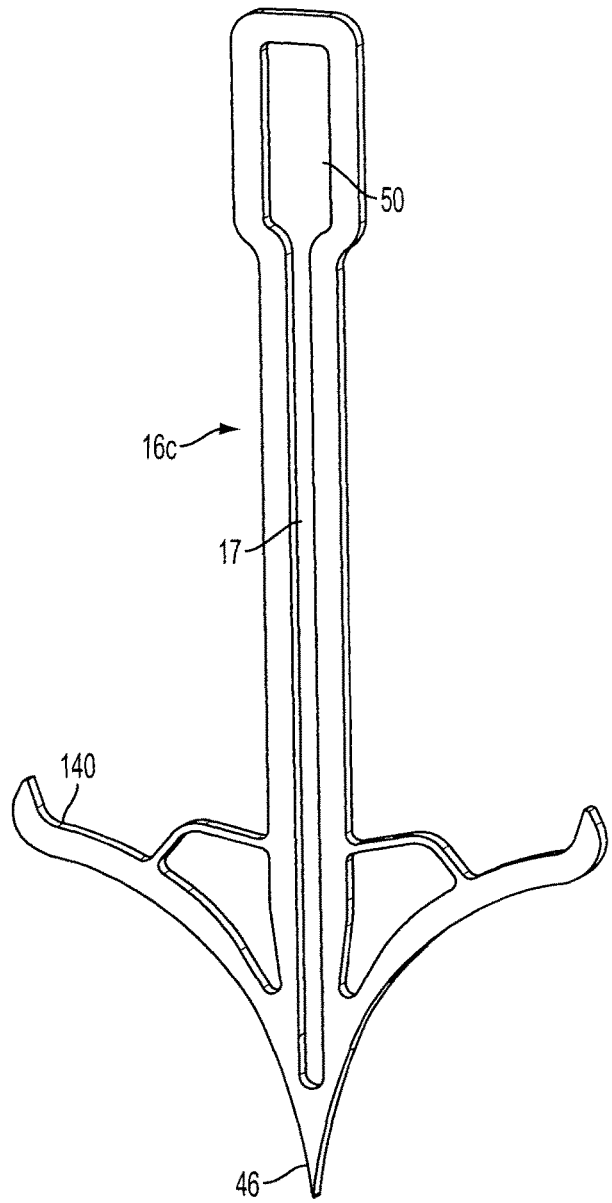

FIGS. 52A and 52 B depict yet another anchor 16d that may be used in place of the anchors 16 shown in FIG. 7. This anchor 16d is similar to the anchor 16 depicted in FIG. 7, but instead of the barb depicted in FIG. 7, this anchor 16d uses one or more arms 140 formed from a shape-memory alloy (SMA) material. These arms are configured to automatically spring outward after being implanted by operation of the SMA material, so that after the arms 140 have sprung outward (as seen in FIG. 52B), the arms cause the anchor to resist extraction from the annulus or the leaflets in a backwards direction. Note that prior to implantation, the arms 140 remain in the collapsed state depicted in FIG. 52A and do not spring outward because they are restrained from doing so by a housing (such as the housing 24 shown in FIGS. 4, 5, and 54A). The preferred materials for this embodiment are similar to those for the embodiment described above in connection with FIGS. 49A and 49B. The length of the anchor 16d is preferably between 3 and 30 mm, more preferably between 5 and 10 mm. The thickness of the material is preferably between 0.1 and 1.5 mm, more preferably between 0.2 and 0.6 mm.

Figure 53:
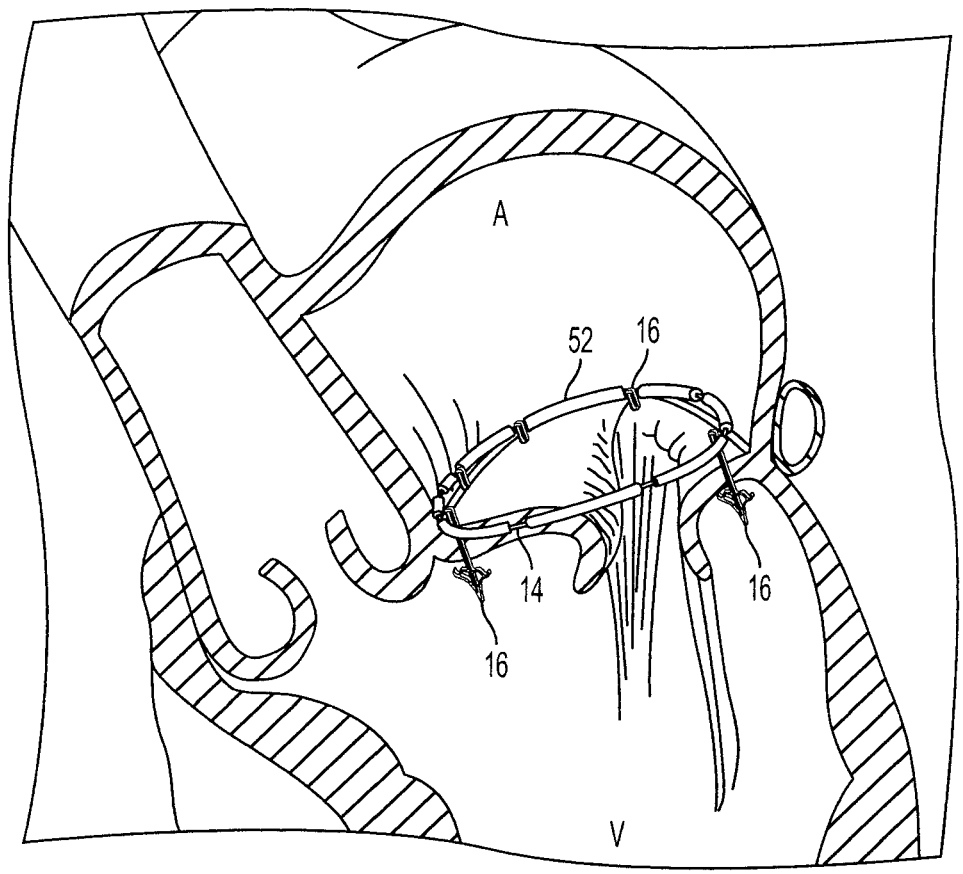
FIG. 53 depicts a tissue engaging member that uses an expandable anchor.

FIG. 53 depicts a tissue engaging member that includes a loop of wire 14, a set of anchors 16 of the type depicted in FIG. 52B that have been implanted into a mitral valve annulus, with a plurality of tissue growth-promotion tubes 52 that are coaxially arranged about the loop of wire. Taken together, the loop of wire 14 and the plurality of tissue growth-promotion tubes 52 collectively form a loop of material. The usage and operation of this tissue engaging member is similar to the tissue engaging member discussed above in connection with FIG. 8, and differs mainly because a different type of anchor is used. Of course, any of alternative anchors described herein may be used in place of the anchor depicted in FIG. 53.

Figure 54B:
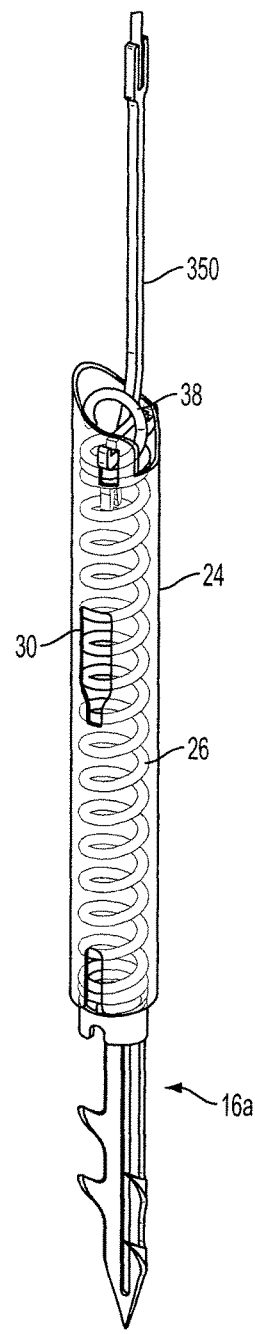

FIGS. 54A and 54B illustrate an embodiment of anchor launching mechanism for launching anchors 16 into the biovalve tissue, e.g. the Mitral valve annulus or leaflets. The anchor launching mechanism in includes a housing 24 that has an open front end. The housing has a cylindrical interior void that includes a first front section and a second rear section. An anchor 16 (e.g., any of the anchors described above) is disposed in the front section of the void in the housing, and an anchor launching spring 26 is disposed in the rear portion of the void in the housing 24 in a compressed state. The spring 26 is preferably a coil spring. In the illustrated embodiment, the back end (i.e., the proximal end) of the spring 26 is retained in housing 24 by a spring retention loop or hook 38. Of course, alternative configurations may be used for preventing the spring 26 from exiting the housing 24.

The anchor launching mechanism includes an actuator configured to (a) prevent the spring from expanding from the compressed state prior to being actuated and (b) permit the spring to expand from the compressed state upon being actuated. The actuator is preferably implemented using an actuator 350 that initially passes coaxially through the anchor launching spring 26. Preferred materials for the actuator 350 include metals (e.g., steel alloys, stainless steel, nitinol), biocompatible plastics, and ceramics. The thickness of the actuator 350 is preferably between 0.05 and 1.0 mm, more preferably between 0.1 and 0.3 mm.

Figure 54C:
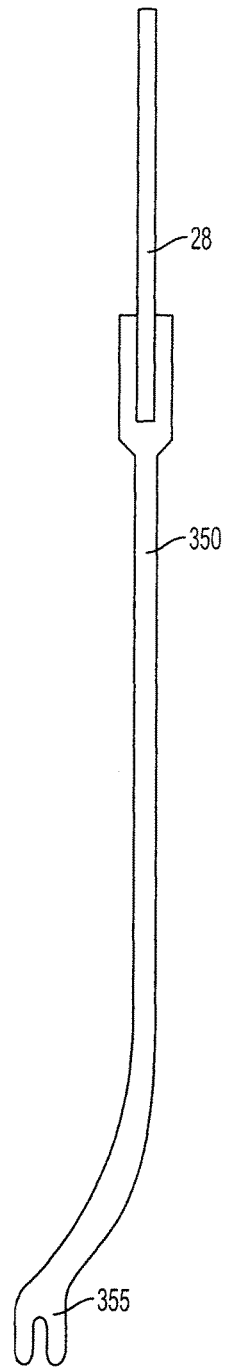

In the initial state (i.e., prior to actuation) depicted in FIG. 54A, the distal portion 355 of actuator 350 passes through and/or interfaces with an opening 30 in the housing. Optionally, the distal portion 355 may be forked (as best seen in FIG. 54C) to engage the opening 30 more securely. The front end (i.e., the distal end) of the spring 26 presses against the back end of the anchor 16. In the illustrated embodiment, the back end of the anchor is the ring 125 located at the back of the anchor 16. Prior to actuation, the actuator 350 passes through the notch 128 in the ring 125 at the back of the anchor 16 and also passes through the opening 30 of the housing 24. The presence of the distal portion 355 of the actuator 350 in this position, engaged with the opening 30, prevents the spring 26 from expanding, thereby keeping the anchor launching spring 26 in a compressed state. In some embodiments, distal portion 355 includes a fork-like tip for engaging the opening 30 of the housing 24 more securely.

The passage of the distal portion 355 through the notch 128 and the opening 30 also operates to align the notch 128 with the opening 30. Preferably, there is an elongated recess 40 at the open end of the housing 24, located directly in front of the opening 30 in the axial direction. Because the notch 128 is aligned with the opening 30, and the elongated recess 40 is directly in front of the opening 30, and the slot 17 is opposite from the notch 128, the anchor 16 will be oriented so that the slot 17 in the anchor 16 is opposite from elongated recess 40. This is advantageous because when the elongated recess 40 is opposite from the slot 17, those features 40, 17 will align so that a loop of wire 14 can pass easily through all the elongated recesses 40 and all the slots 17 in each of the anchor launchers and anchors, which makes it easier to launch the anchors into the target tissue.

An actuation wire 28 (i.e., the "pull wire") is attached to the proximal portion of the actuator 350 using any suitable attachment approach (e.g., welding, crimping, etc.). The actuator 350 then can be pulled in a proximal direction by pulling on the pull wire 28. When this occurs, the distal portion 355 of actuator 350 is pulled inwardly through the opening 30 and is withdrawn from the opening 30. At this point, the spring 26 will expand into the front section of the housing 24 and push the anchor 16 forward such that at least a portion of the anchor 16 exits the front end of housing. The spring 26 pushes the anchor 16 with sufficient force to implant the anchor into the tissue.

Note that in alternative embodiments (not shown), instead of using a discrete actuator 350 that is connected to the end of the actuation wire 28, the discrete actuator can be eliminated, and the distal end of the actuation wire 28 itself can serve as the actuator. In either case, it is preferable to pull the wire 28 in the proximal direction with a jerk (i.e., with rapid acceleration), because it makes the launching more reliable and prevents the tissue engaging member from lifting away from the surface of the tissue prior to implantation.

Figure 55:
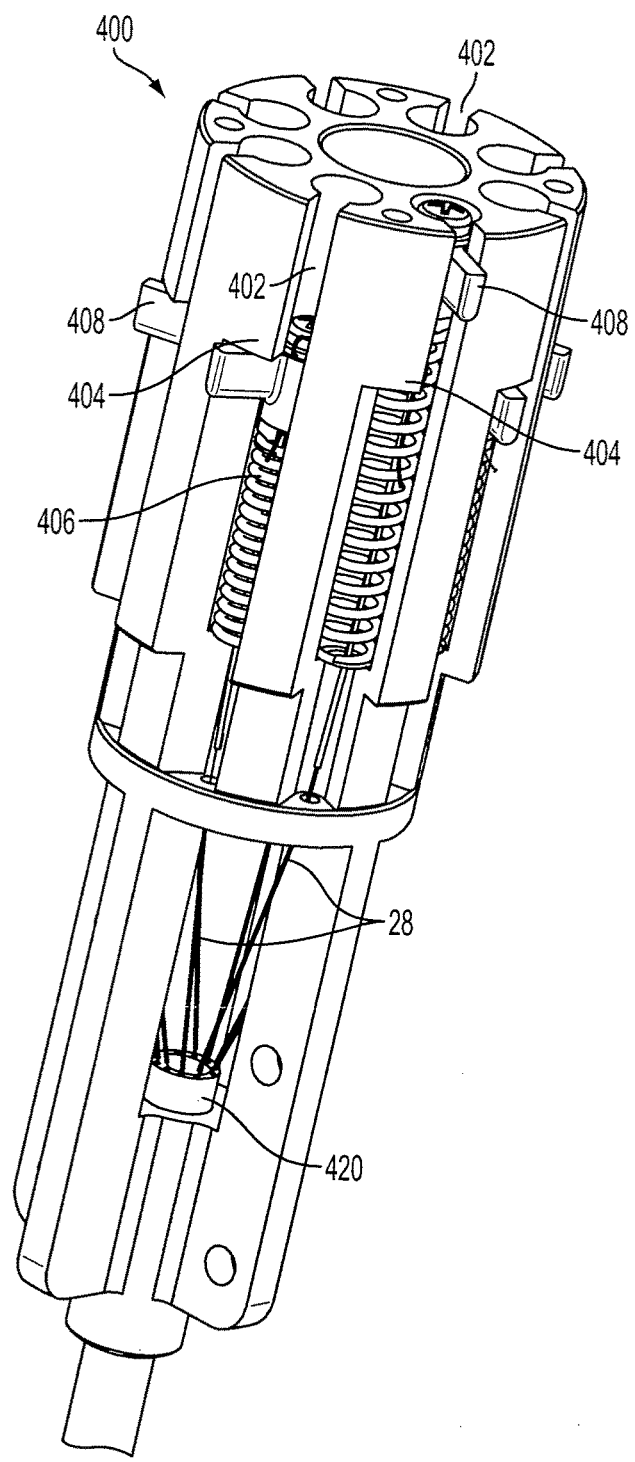
FIG. 55 depicts an apparatus for pulling the wire to trigger the anchor launching mechanism of FIG. 54.

FIG. 55 depicts a suitable apparatus for pulling the wires 28 in the proximal direction in this manner, to trigger the anchor launchers shown in FIGS. 54A and 54B. The pulling apparatus has a plurality of actuators housed in a housing 400. Each of these actuators is housed in a channel 402 that runs through the housing 400 in a proximal-to-distal direction. Preferably, the housing 400 is cylindrical, and the channels 402 are distributed within the cylindrical housing close to the circumference of the cylinder.

Each actuator has a shoulder 404 disposed adjacent to the channel 402. A compressed spring 406 is disposed in a distal portion of the channel. The distal end of the spring 406 is preferably fixed, and the proximal end is preferably movable. The channel 402 is configured to permit expansion of the spring 406 in a proximal direction.

Each actuator also has a tab 408 that is affixed to the proximal end of the spring 406 using any suitable attachment system (e.g., screws, crimping, etc.). In the embodiments where the housing is cylindrical, it is preferable to have the tabs 408 extend radially outward from the channels 402 beyond the circumference of the cylindrical housing 400. The tab may be affixed directly to the spring 406, or the tab may be connected through intermediate members. The tab 408 is configured to be movable between (1) a first position in which movement of the tab 408 in a proximal direction is blocked by the shoulder 404, and (2) a second position in which movement of the tab 408 in a proximal direction is not blocked by the shoulder 404. As soon as the tab 408 is moved from the first position to the second position, the spring 406 will expand within the channel and move from its compressed state to its released state, with the proximal end of the spring moving in a proximal direction.

The proximal end of the pull wire 28 is attached (either directly or indirectly) to the spring 406 or the tab 408 and a distal portion of the pull wire 28 extends to the anchor launcher. When the proximal end of the spring 406 moves in the proximal direction, the pull wire 28 is pulled in the proximal direction with the preferred jerking motion. Optionally, the pull wires may be threaded though individual corresponding apertures to avoid tangling. For such purpose, a pull wire distribution collar 420 with respective distribution holes (not shown) disposed therein may be provided at the distal end of the housing 400.

A rotatable cap (not shown) may be is used to push the tabs from the first position to the second position. In some embodiments, the interior surface of the cap has a cylindrical void configured to surround the cylindrical housing 400, and the interior surface has a single protrusion configured to sequentially push each of the tabs from the first position to the second position when the cap is rotated. In this case, the anchors will launch sequentially. In alternative embodiments, the interior surface has a plurality of protrusions configured to simultaneously push a plurality of the tabs from the first position to the second position when the cap is rotated. In this case, a plurality of anchors will launch simultaneously.

Figure 56A:
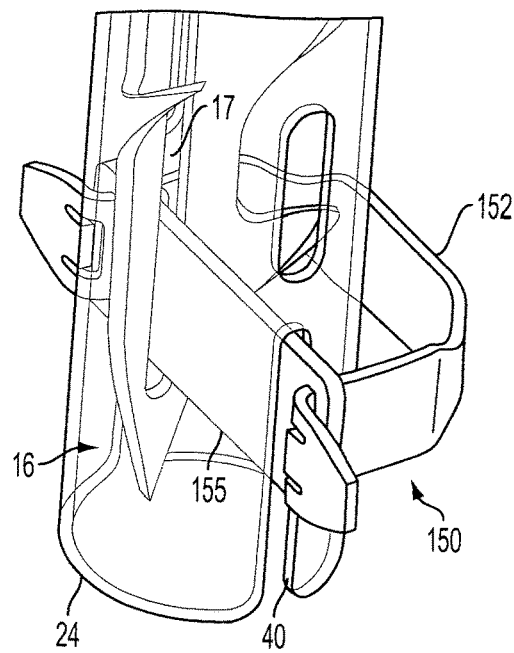
FIGS. 56A and 56B depict an alternative approach for implementing a tissue engaging member.
Figure 56B:
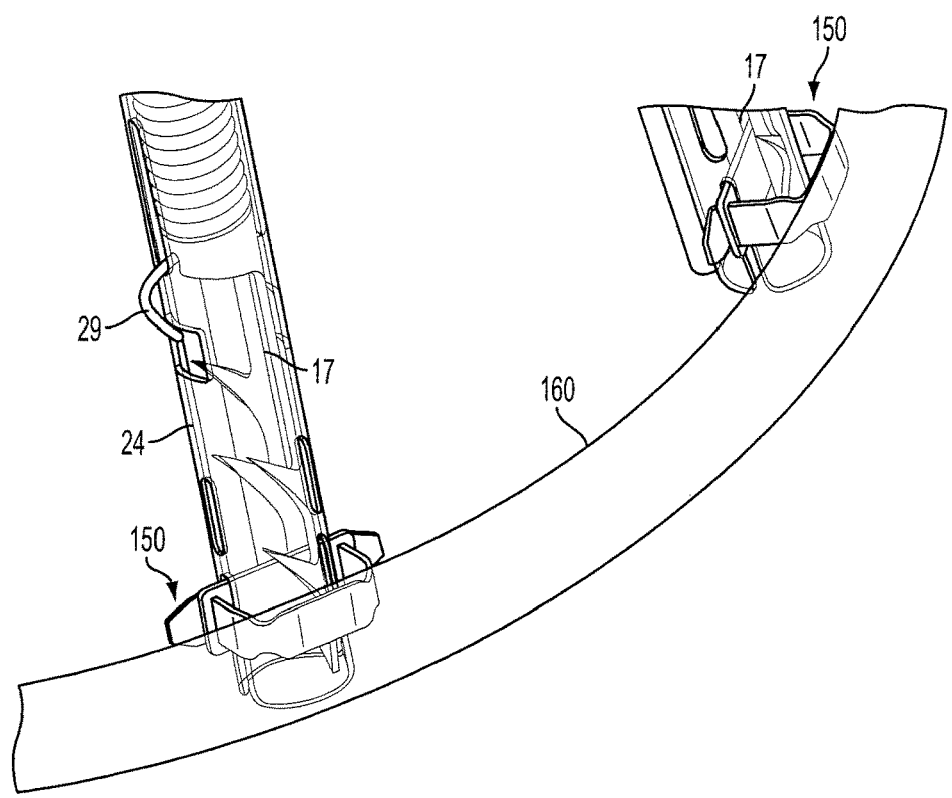

FIGS. 56A and 56B depict an alternative approach for implementing the tissue engaging member. In this embodiment, the tissue engaging member includes three sets of parts. The first set is a loop of material 160 configured to contact at least a portion of the annulus or the leaflets when the loop of material is deployed. This loop of material can be a wire, or in alternative embodiments the loop may be a different loop of material such as a tube, strip, chain, braid, etc., or a combination of multiple materials.

The second set is a plurality of anchors 16, each of which has a pointy front end and a back end. Each of the anchors also has a slot 17 that runs in a front-to-back direction. The front ends of the anchors 16 are configured for implantation into the annulus or the leaflets in a forward direction. The anchors are configured so that subsequent to implantation, the anchors resist extraction from the annulus or the leaflets in a backwards direction. The anchor embodiments described above can be used for this purpose. The anchors are arranged with respect to the loop of material so that when the loop of material is deployed the anchors are distributed about the loop of material with the front ends of the anchors facing the annulus or the leaflets.

The third set is a plurality of linking members 150 that are affixed to the loop of material 160. At least a portion of each of the linking members 150 passes through the slot in a respective anchor, and each of the linking members is configured to slide with respect to the slot in the respective anchor in the front-to-back direction. In some embodiments, the linking members include a strip of material 155 that passes through the slot in the respective anchor. This strip of material 155 may be connected to the loop of material 160 through at least one intermediate member 152. For example, if the loop of material 160 is a hollow tube, the intermediate member 152 could be a C-shaped bracket that connects the loop of material 160 to the strip of material 155. In alternative embodiments (not shown), the strip of material 155 may be directly connected to the loop of material 160. Preferred materials for the linking members 150 include metals (e.g., steel alloys, stainless steel, nitinol), biocompatible plastics, and ceramics. The width is preferably between 0.2 and 3 mm, more preferably between 0.5 and 1.5 mm. The thickness of the material is preferably between 0.05 and 1.0 mm, more preferably between 0.1 and 0.3 mm.

In the embodiment illustrated in FIG. 56B, the anchors and the linking members are disposed inside the loop at the inner circumference of the loop. In alternative embodiments (not shown), the anchors and the linking members may be disposed outside the loop at the outer circumference of the loop.

Prior to launching, the loop of material 160 is delivered to its desired location in contact with the annulus or leaflets, in a manner similar to the embodiments described above. The anchors 16 are then launched (e.g., using any of the launching mechanisms described above). When the anchors are launched, the anchors will move forward while the strips 155 of the linking members 150 remain stationary. This will implant the tissue engaging member in the desired location. As a result of the movement of the anchors, the linking members 150 will have shifted (with respect to the slot 17) from the front of the slot 17 towards the back of the slot 17.

Note that the embodiment depicted in FIG. 56B differs from the FIG. 3 embodiment because in the FIG. 56B embodiment the loop of material 160 is connected to the slot 17 in the anchor via the linking members 150. In contrast, the loop of wire 14 passes directly through the slot in the anchor 16 in the FIG. 3 embodiment.

Figure 57C:
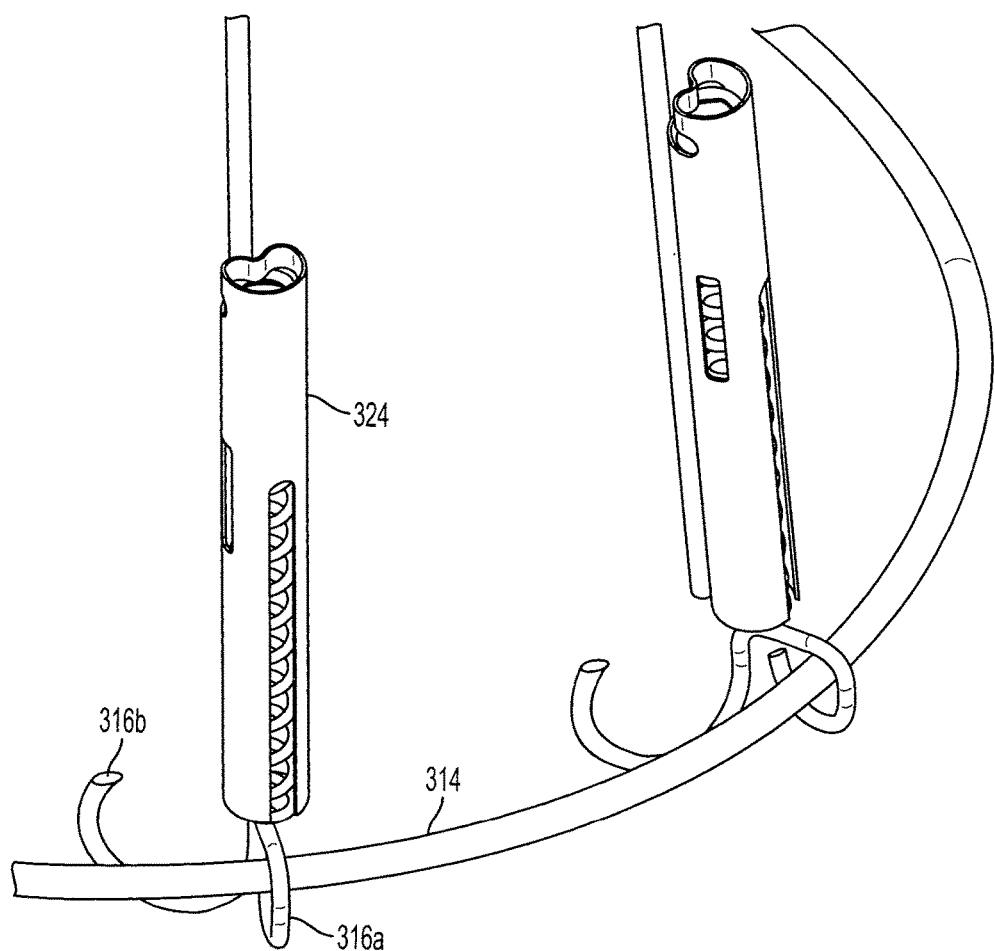

FIGS. 57A, 57B, and 57C show yet another embodiment of an anchor, which relies on a component 316 that normally has the curled configuration shown in FIG. 57B. However, when the anchor 316 is still disposed in the launch mechanism housing 324, the anchor 316 is deformed and takes on a generally elongated shape shown in FIG. 57A. Housing 324 is preferably generally cylindrical in shape. A spring 326 is dispose in the proximal end of the housing 324, and the spring is configured to push the anchor 316 out of the housing 324 when it is triggered. The trigger mechanisms described above in connection with other embodiments may be used for this embodiment.

Upon being launched, the anchor 316 is pushed out of the distal end of the housing 324 and will immediately spring back to its original curled configuration shown in FIG. 57B. In some embodiments, the return to the original shape may be accomplished by forming the anchor 316 from a shape memory alloy. The distal tip 316b of the anchor 316 is preferably sharp, and is configured to pierce the tissue upon exiting the housing 324. The distal tip 316b will then curl around and engage the target tissue.

In this embodiment, anchor 316 preferably has a top portion 316a that forms a loop engaging eyelet, through which the loop of wire 314 is threaded, as seen in FIG. 57C. In such an embodiment, eyelet can also surround any tissue growth-promotion tubes (not shown) that may coaxially surround the loop 314. When the distal tip 316b is engaged with the tissue, the eyelet of the top portion 316a will hold the loop next to the tissue. Note that unlike the embodiments described above, the loop 314 in this embodiment is not positioned in contact with the tissue prior to launching. Instead, the loop 314 travels down to its final destination together with the eyelet of the top portion 316a during the implantation procedure. Note also that the delivery of the launch mechanism housings 324 to their intended locations prior to launching for this embodiment may be implemented in similar ways to the other embodiments described herein.

Figure 58:
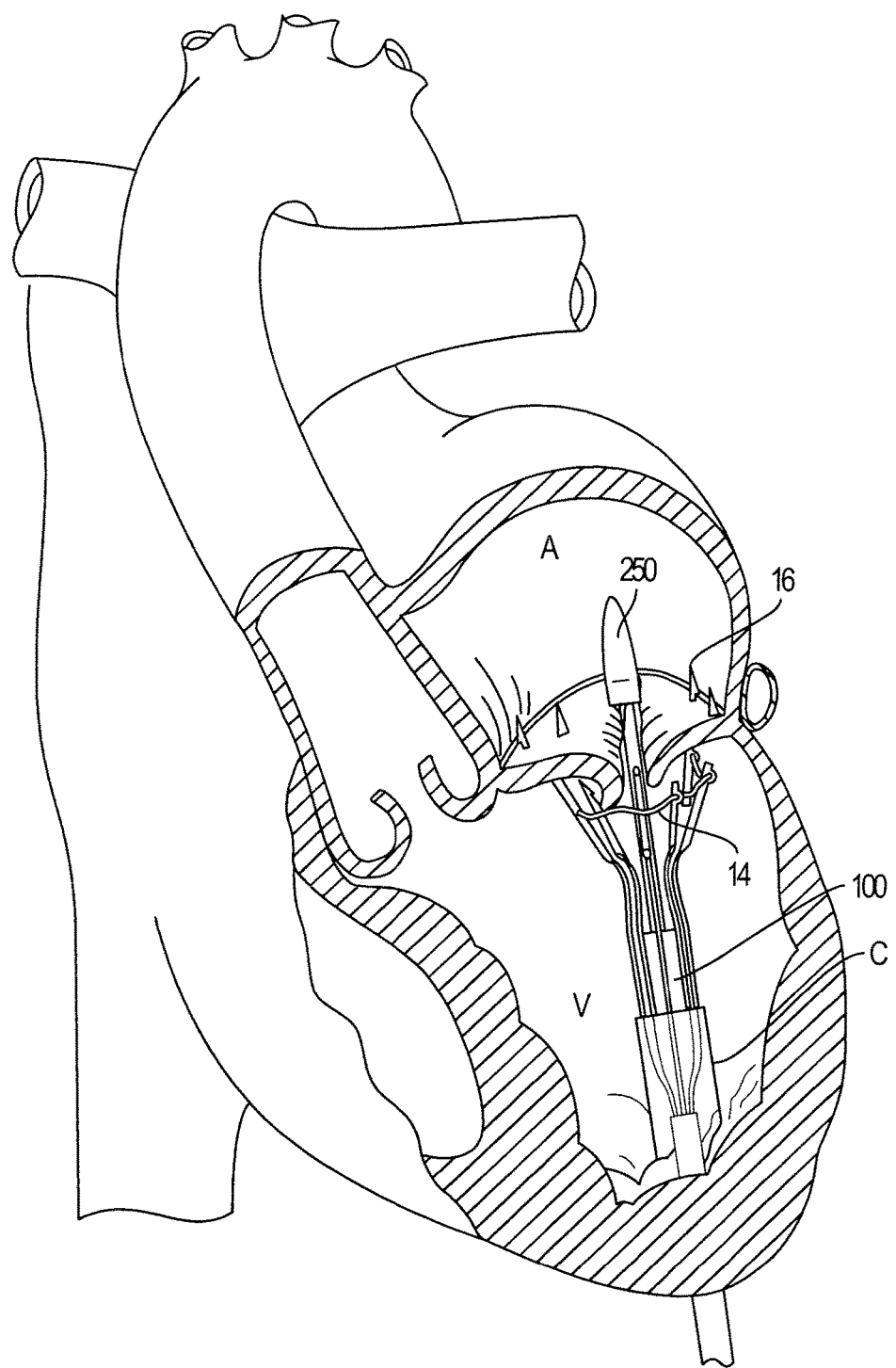
FIG. 58 depicts an embodiment for implanting a ring and a valve in a single procedure.

FIG. 58 illustrates an embodiment for implanting a ring and a valve in a single procedure. In this embodiment, a tissue engaging member that includes anchors 16 and a loop 14 is mounted on anchor positioning leads 260 that extend from a delivery catheter C. In the case of a Mitral valve repair, the tissue engaging member is preferably inserted via the heart's apex, via an insertion catheter or encapsulating cylinder, together with an expandable valve 100. Initially, the valve 100 is located between the anchor positioning leads 260 in a collapsed state. Optionally, a nose cone 250 may be used to help guide the tissue engaging member to the correct location. After the anchors 16 are inserted/launched, the valve 100 is advanced to a location within the loop 14 and expanded from its original collapsed state (depicted in FIG. 38) to its final expanded configuration (depicted in FIGS. 39 and 37). The insertion catheter and encapsulating cylinder 102 are then removed, leaving the tissue engaging member and the valve 100 behind.

Figure 60:
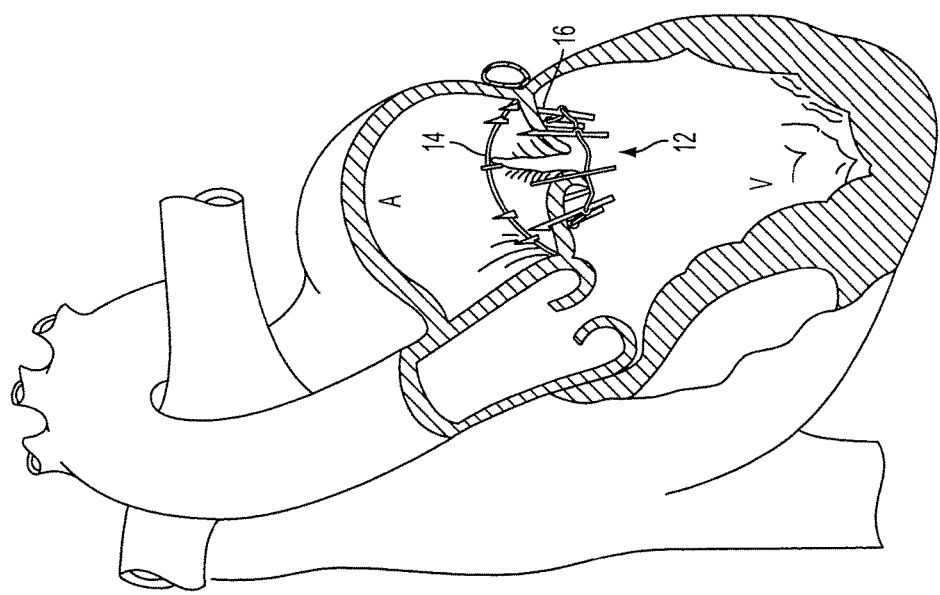
FIG. 60 depicts the end result of using the FIG. 59 embodiment.
Figure 59:
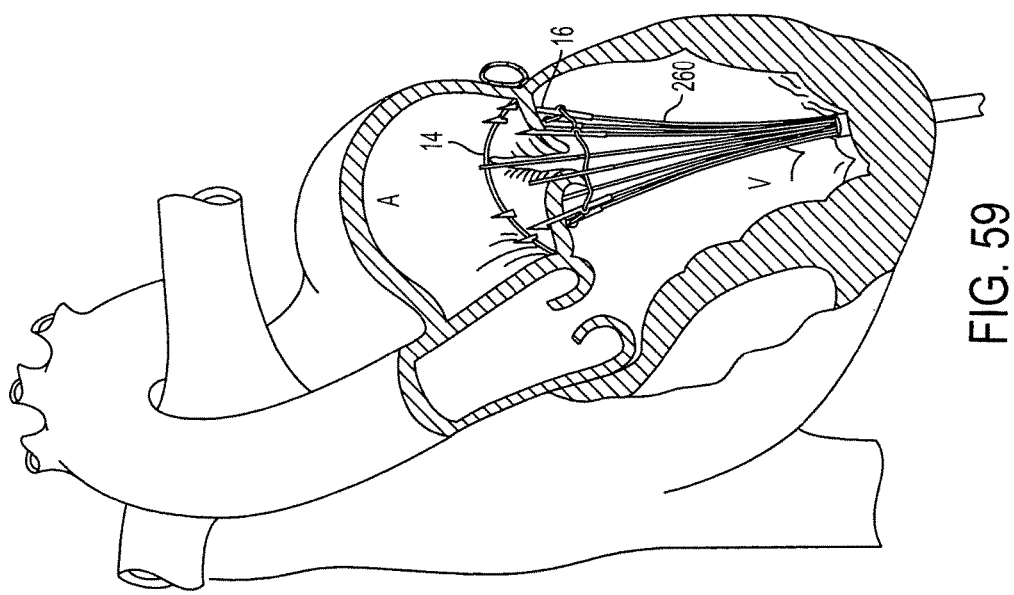
FIG. 59 depicts an embodiment in which anchor positioning is implemented using elongated needle-like members.

FIG. 59 shows an embodiment wherein the anchor positioning leads 260 are implemented in the form of elongated needle-like members. In some embodiments, the elongated needle-like anchor positioning leads are stiff enough so that they can press the anchors 16 directly into the bio-tissue, without relying on a spring-based anchor launching mechanism. FIG. 60 shows the situation after the anchor positioning leads 260 have been removed from the heart.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for performing a procedure on a heart valve, the heart valve having an annulus and leaflets, the apparatus comprising:
    a tissue engaging member including
    (a) a loop of material configured to contact at least a portion of the annulus or the leaflets when the loop of material is deployed,
    (b) a plurality of anchors, each of the plurality of anchors having a pointy front end and a back end, each of the plurality of anchors having An elongated slot, the elongated slot having a direction of elongation that runs in a front-to-back direction, wherein the front ends of the plurality of anchors are configured for implantation into the annulus or the leaflets in a forward direction and wherein the plurality of anchors are configured so that subsequent to implantation, the plurality of anchors resist extraction from the annulus or the leaflets in a backwards direction, wherein the plurality of anchors are arranged with respect to the loop of material so that when the loop of material is deployed the plurality of anchors are distributed about the loop of material with the front ends of the plurality of anchors facing the annulus or the leaflets, and
    (c) a plurality of linking members that are affixed to the loop of material, at least a portion of each of the linking members passing through the slot in a respective anchor, wherein each of the linking members is configured to slide with respect to the slot in the respective anchor in the front-to-back direction.

2. The apparatus of claim 1, wherein each of the linking members comprises a strip of material that passes through the slot in the respective anchor.

3. The apparatus of claim 2, wherein the strip of material is connected to the loop of material through at least one intermediate member.

4. The apparatus of claim 1, wherein the linking members are disposed inside the loop.

5. The apparatus of claim 1, wherein the linking members are disposed outside the loop.

6. The apparatus of claim 1, wherein the loop of material comprises a closed loop.

7. The apparatus of claim 1, further comprising means for implanting the plurality of anchors into the annulus or the leaflets so that the tissue engaging member becomes affixed to the annulus or the leaflets.

8. The apparatus of claim 1, further comprising a plurality of compressed springs configured to, respectively, implant the plurality of anchors into the annulus or the leaflets so that the tissue engaging member becomes affixed to the annulus or the leaflets.

9. The apparatus of claim 1, further comprising a plurality of pull wires configured to, respectively, implant the plurality of anchors into the annulus or the leaflets so that the tissue engaging member becomes affixed to the annulus or the leaflets.

10. The apparatus of claim 1, further comprising a plurality of anchor launchers configured to, respectively, implant the plurality of anchors into the annulus or the leaflets so that the tissue engaging member becomes affixed to the annulus or the leaflets.

11. The apparatus of claim 1, further comprising a plurality of springs, wherein each spring is arranged with respect to a respective one of the plurality of anchors so that when the spring expands from a compressed state to an expanded state, the spring drives the respective anchor into the annulus or the leaflets.

12. The apparatus of claim 11, further comprising a plurality of actuators, wherein each of the actuators is movable between (a) a first position in which the actuator holds a respective spring in the compressed state and (b) a second position in which the actuator permits the respective spring to expand to the expanded state.

* * * * *

UNITED STATES PATENT AND TRADEMARK OFFICE
CERTIFICATE OF CORRECTION

PATENT NO.        : 10,206,776 B2
APPLICATION NO.   : 14/895711
DATED             : February 19, 2019
INVENTOR(S)       : David Alon Page 1 of 1

It is certified that error appears in the above-identified patent and that said Letters Patent is hereby corrected as shown below:

On the Title Page

Item (71) Applicant: please replace "David Alon, Zichron Yaacov (IL)" with -- Cardiac Implants LLC, Tarrytown, NY (US) --.

Signed and Sealed this
Twenty-third Day of April, 2019

Andrei Iancu
*Director of the United States Patent and Trademark Office*